(12) United States Patent
Ferro, Jr. et al.

(10) Patent No.: US 11,894,138 B2
(45) Date of Patent: *Feb. 6, 2024

(54) REMOTE DIAGNOSTIC TESTING AND TREATMENT

(71) Applicant: EMED LABS, LLC, Miami, FL (US)

(72) Inventors: Michael W. Ferro, Jr., Palm Beach, FL (US); Sam Miller, Hollywood, FL (US); Colman Thomas Bryant, Fort Lauderdale, FL (US); Zachary Carl Nienstedt, Wilton Manors, FL (US); Marco Magistri, Miami, FL (US); Adam Charles Carlson, Miami, FL (US); Igor Javier Rodriguez, Miami, FL (US); James Thomas Heising, Richland, WA (US); John Ray Permenter, Miami, FL (US)

(73) Assignee: EMED LABS, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/171,149

(22) Filed: Feb. 17, 2023

(65) Prior Publication Data

US 2023/0207118 A1    Jun. 29, 2023

Related U.S. Application Data

(63) Continuation of application No. 17/700,141, filed on Mar. 21, 2022, now Pat. No. 11,615,888.
(Continued)

(51) Int. Cl.
*G16H 40/67* (2018.01)
*G16H 20/10* (2018.01)
(Continued)

(52) U.S. Cl.
CPC .......... *G16H 40/67* (2018.01); *G06T 19/006* (2013.01); *G16H 10/60* (2018.01); *G16H 20/10* (2018.01);
(Continued)

(58) Field of Classification Search
CPC .................. G16H 40/67; G06Q 50/20–26
See application file for complete search history.

(56) References Cited

U.S. PATENT DOCUMENTS 5,999,525 A    12/1999   Krishnaswamy
7,110,525 B1    9/2006   Heller et al.
(Continued)

FOREIGN PATENT DOCUMENTS

CN    103153248    6/2013
CN    105266897    1/2016
(Continued)

OTHER PUBLICATIONS

Abbott, Dec. 2020, Binaxnow™ covid-19 Ag card home test and Navica™app, https://web.archive.org/web/20201224151604/https://wwww.globalpointofcare/abbott, 3 pp.
(Continued)

*Primary Examiner* — Jason S Tiedeman
*Assistant Examiner* — Jessica Marie Webb
(74) *Attorney, Agent, or Firm* — Perkins Coie LLP

(57) ABSTRACT

A medical diagnostic kit are described. In one example, a medical diagnostic kit includes a container, and a plurality of medical diagnostic test kits located within the container. Each of the plurality of medical diagnostic test kits can include equipment necessary to perform a particular self-administered medical diagnostic test. The plurality of medical diagnostic test kits can include at least a first medical diagnostic kit adapted to facilitate user completion of a first medical diagnostic test and a second medical diagnostic kit
(Continued)

adapted to facilitate user completion of a second medical diagnostic test different from the first medical diagnostic test. The container can include a machine-readable code located on an external surface of the container.

14 Claims, 66 Drawing Sheets

Related U.S. Application Data

(60) Provisional application No. 63/266,233, filed on Dec. 30, 2021, provisional application No. 63/266,158, filed on Dec. 29, 2021, provisional application No. 63/202,723, filed on Jun. 22, 2021, provisional application No. 63/202,028, filed on May 24, 2021, provisional application No. 63/179,101, filed on Apr. 23, 2021, provisional application No. 63/164,669, filed on Mar. 23, 2021.

(51) Int. Cl.
  G16H 10/60     (2018.01)
  G16H 50/20     (2018.01)
  G06T 19/00     (2011.01)
  G06K 19/06     (2006.01)

(52) U.S. Cl.
  CPC ....... *G16H 50/20* (2018.01); *G06K 19/06028* (2013.01); *G06K 19/06037* (2013.01)

(56) References Cited

U.S. PATENT DOCUMENTS

| | | |
|---|---|---|
| 7,176,936 B2 | 2/2007 | Sauer et al. |
| 7,491,198 B2 | 2/2009 | Kockro |
| 7,662,113 B2 | 2/2010 | Pearl et al. |
| 8,108,190 B2 | 1/2012 | Riener et al. |
| 8,253,778 B2 | 8/2012 | Atsushi |
| 8,314,815 B2 | 11/2012 | Navab et al. |
| 8,485,038 B2 | 7/2013 | Sengupta et al. |
| 8,520,080 B2 | 8/2013 | Havens |
| 8,611,988 B2 | 12/2013 | Miyamoto |
| 8,713,130 B2 | 4/2014 | Logan et al. |
| 8,768,022 B2 | 7/2014 | Miga et al. |
| 8,814,691 B2 | 8/2014 | Haddick et al. |
| 8,911,358 B2 | 12/2014 | Koninckx |
| 8,948,935 B1 | 2/2015 | Peeters et al. |
| 8,982,156 B2 | 3/2015 | Maggiore |
| 9,030,446 B2 | 5/2015 | Mistry et al. |
| 9,082,319 B2 | 7/2015 | Shimada et al. |
| 9,111,383 B2 | 8/2015 | Fein et al. |
| 9,256,711 B2 | 2/2016 | Horseman |
| 9,262,743 B2 | 2/2016 | Heins et al. |
| 9,285,871 B2 | 3/2016 | Geisner et al. |
| 9,338,622 B2 | 5/2016 | Bjontegard |
| 9,345,957 B2 | 5/2016 | Geisner et al. |
| 9,380,177 B1 | 6/2016 | Rao et al. |
| 9,424,761 B2 | 8/2016 | Tuchschmid et al. |
| 9,498,132 B2 | 11/2016 | Maier-Hein et al. |
| 9,547,917 B2 | 1/2017 | Zamer |
| 9,563,266 B2 | 2/2017 | Banerjee et al. |
| 9,600,934 B2 | 3/2017 | Odessky et al. |
| 9,606,992 B2 | 3/2017 | Geisner et al. |
| 9,648,436 B2 | 5/2017 | Kraft |
| 9,788,714 B2 | 10/2017 | Krueger |
| 9,836,888 B2 | 12/2017 | Skidmore |
| 9,877,642 B2 | 1/2018 | Duret |
| 9,886,458 B2 | 2/2018 | Jung et al. |
| 9,892,561 B2 | 2/2018 | Choukroun et al. |
| 9,898,662 B2 | 2/2018 | Tsuda et al. |
| 9,916,002 B2 | 3/2018 | Petrovskaya et al. |
| 9,972,137 B2 | 5/2018 | Petrovskaya et al. |
| 10,013,896 B2 | 7/2018 | Feins et al. |
| 10,052,026 B1 | 8/2018 | Tran |
| 10,106,172 B2 | 10/2018 | Wingfield et al. |
| 10,108,266 B2 | 10/2018 | Banerjee et al. |
| 10,127,734 B2 | 11/2018 | Stroila |
| 10,156,900 B2 | 12/2018 | Publicover et al. |
| 10,197,803 B2 | 2/2019 | Badiali et al. |
| 10,216,957 B2 | 2/2019 | Jung et al. |
| 10,231,614 B2 | 3/2019 | Krueger |
| 10,244,198 B2 | 3/2019 | Cizerle |
| 10,295,815 B2 | 5/2019 | Romanowski et al. |
| 10,322,313 B2 | 6/2019 | McKirdy |
| 10,346,889 B1 | 7/2019 | Reiss et al. |
| 10,386,918 B2 | 8/2019 | Shin |
| 10,430,985 B2 | 10/2019 | Harrises et al. |
| 10,474,233 B2 | 11/2019 | Swaminathan et al. |
| 10,524,715 B2 | 1/2020 | Sahin |
| 10,535,202 B2 | 1/2020 | Schmirler et al. |
| 10,540,776 B2 | 1/2020 | Tran et al. |
| 10,559,117 B2 | 2/2020 | Kaeser et al. |
| 10,593,092 B2 | 3/2020 | Solomon |
| 10,643,210 B2 | 5/2020 | Smith et al. |
| 10,660,522 B2 | 5/2020 | Redei |
| 10,664,572 B2 | 5/2020 | Bitran et al. |
| 10,758,209 B2 | 9/2020 | Boctor et al. |
| 10,788,791 B2 | 9/2020 | Gelman et al. |
| 10,802,695 B2 | 10/2020 | Daniels et al. |
| 10,824,310 B2 | 11/2020 | Acharya et al. |
| 10,832,488 B2 | 11/2020 | Petrovskaya et al. |
| 10,849,688 B2 | 12/2020 | Rios et al. |
| 10,885,530 B2 | 1/2021 | Mercury et al. |
| 10,888,389 B2 | 1/2021 | Draelos et al. |
| 10,892,052 B2 | 1/2021 | Jordan et al. |
| 10,910,016 B2 | 2/2021 | Rothschild et al. |
| 10,932,705 B2 | 3/2021 | Muhsin et al. |
| 10,943,407 B1 | 3/2021 | Morgan et al. |
| 10,945,807 B2 | 3/2021 | Gibby et al. |
| 10,957,111 B2 | 3/2021 | Weisman et al. |
| 10,984,910 B2 | 4/2021 | Burkholz et al. |
| 10,991,190 B1 | 4/2021 | Luthra et al. |
| 10,991,461 B2 | 4/2021 | Divine et al. |
| 11,004,271 B2 | 5/2021 | Cvetko et al. |
| 11,017,694 B2 | 5/2021 | Buras et al. |
| 11,152,093 B1 | 10/2021 | Hopen, Sr. et al. |
| 11,194,995 B1 | 12/2021 | Profida Ferreira et al. |
| 11,257,572 B1 | 2/2022 | Narke et al. |
| 11,219,428 B2 | 3/2022 | Burkholz |
| 11,270,235 B1 | 3/2022 | Daianu et al. |
| 11,289,196 B1 | 3/2022 | Ferro, Jr. et al. |
| 11,315,053 B1 | 4/2022 | Powell et al. |
| 11,367,530 B1 | 6/2022 | Ferro, Jr. et al. |
| 11,369,454 B1 | 6/2022 | Ferro, Jr. et al. |
| 11,373,756 B1 | 6/2022 | Ferro, Jr. et al. |
| 11,393,586 B1 | 7/2022 | Ferro, Jr. et al. |
| 11,410,773 B2 | 8/2022 | Ferro |
| 11,623,114 B2 | 4/2023 | Mohieldin |
| 2005/0277872 A1 | 12/2005 | Colby et al. |
| 2007/0048723 A1 | 3/2007 | Brewer et al. |
| 2009/0004055 A1 | 1/2009 | Darrigrand et al. |
| 2009/0263775 A1 | 10/2009 | Ullrich |
| 2010/0121156 A1 | 5/2010 | Yoo |
| 2010/0159434 A1 | 6/2010 | Lampotang et al. |
| 2011/0164105 A1 | 7/2011 | Lee |
| 2011/0207108 A1 | 8/2011 | Dorman |
| 2011/0213619 A1 | 9/2011 | Henke |
| 2012/0053955 A1 | 3/2012 | Martin et al. |
| 2012/0125995 A1* | 5/2012 | Kim ............... G06F 16/9554 235/375 |
| 2012/0221960 A1 | 8/2012 | Robinson |
| 2013/0096937 A1 | 4/2013 | Campbell et al. |
| 2013/0253339 A1 | 9/2013 | Reyes |
| 2013/0328997 A1 | 12/2013 | Desai |
| 2013/0344470 A1 | 12/2013 | Morgan et al. |
| 2014/0160264 A1 | 6/2014 | Taylor et al. |
| 2014/0253590 A1 | 9/2014 | Needham et al. |
| 2014/0304335 A1 | 10/2014 | Fung et al. |
| 2015/0187048 A1 | 7/2015 | Johnson |
| 2016/0125765 A1 | 5/2016 | Meretei et al. |
| 2016/0189573 A1 | 6/2016 | Bush |
| 2016/0200462 A1 | 7/2016 | Kriheli |

(56) References Cited

U.S. PATENT DOCUMENTS

| | | |
|---|---|---|
| 2016/0259911 A1 | 9/2016 | Koester |
| 2016/0292378 A1 | 10/2016 | Saric |
| 2016/0371884 A1 | 12/2016 | Benko et al. |
| 2017/0011200 A1* | 1/2017 | Arshad ................ G16H 30/20 |
| 2017/0173262 A1 | 3/2017 | Veltz |
| 2017/0103440 A1 | 4/2017 | Xing et al. |
| 2017/0106239 A1 | 4/2017 | Sutton |
| 2017/0115742 A1 | 4/2017 | Xing et al. |
| 2017/0146801 A1 | 5/2017 | Stempora |
| 2017/0302880 A1 | 10/2017 | Cizerle |
| 2017/0323062 A1* | 11/2017 | Djajadiningrat .... G06F 16/3326 |
| 2018/0012176 A1 | 1/2018 | McHale |
| 2018/0039737 A1 | 2/2018 | Dempers et al. |
| 2018/0092595 A1 | 4/2018 | Chen et al. |
| 2018/0140362 A1 | 5/2018 | Cali et al. |
| 2018/0173913 A1 | 6/2018 | Pulitzer et al. |
| 2018/0190373 A1 | 7/2018 | Pulitzer et al. |
| 2018/0197624 A1 | 7/2018 | Robaina et al. |
| 2018/0225982 A1 | 8/2018 | Jaeh et al. |
| 2018/0253840 A1 | 9/2018 | Tran |
| 2018/0341919 A1 | 11/2018 | Luhman |
| 2018/0353073 A1 | 12/2018 | Boucher et al. |
| 2018/0365383 A1 | 12/2018 | Bates |
| 2019/0000564 A1 | 1/2019 | Navab et al. |
| 2019/0005195 A1 | 1/2019 | Peterson |
| 2019/0012176 A1 | 1/2019 | Stephens |
| 2019/0020651 A1 | 1/2019 | Soon-Shiong et al. |
| 2019/0025919 A1 | 1/2019 | Tadi et al. |
| 2019/0064520 A1 | 2/2019 | Christensen |
| 2019/0073110 A1 | 3/2019 | Bradley et al. |
| 2019/0087951 A1 | 3/2019 | Hanina |
| 2019/0088026 A1* | 3/2019 | Isaacson ................ G06F 3/014 |
| 2019/0115097 A1* | 4/2019 | Macoviak ............ G16H 40/67 |
| 2019/0139318 A1 | 5/2019 | Tierney et al. |
| 2019/0179584 A1 | 6/2019 | Masters |
| 2019/0206134 A1 | 7/2019 | Devam et al. |
| 2019/0216452 A1 | 7/2019 | Nawana et al. |
| 2019/0259483 A1 | 8/2019 | Potts |
| 2019/0261914 A1 | 8/2019 | Davis et al. |
| 2019/0266663 A1 | 8/2019 | Keeler et al. |
| 2019/0346429 A1 | 11/2019 | Harris |
| 2019/0378080 A1 | 12/2019 | Srinivasan et al. |
| 2019/0378624 A1* | 12/2019 | Pulitzer ................ G16H 50/20 |
| 2019/0380790 A1 | 12/2019 | Fuchs et al. |
| 2019/0391638 A1 | 12/2019 | Khaderi et al. |
| 2020/0000401 A1 | 1/2020 | Dullen |
| 2020/0020171 A1 | 1/2020 | Hendricks et al. |
| 2020/0020454 A1 | 1/2020 | McGarvey |
| 2020/0073143 A1 | 3/2020 | Macnamara et al. |
| 2020/0101367 A1 | 4/2020 | Tran et al. |
| 2020/0152339 A1* | 5/2020 | Pulitzer ................ G16H 50/70 |
| 2020/0174756 A1 | 6/2020 | Cerar et al. |
| 2020/0175769 A1 | 6/2020 | Mandala |
| 2020/0205913 A1 | 7/2020 | Carnes et al. |
| 2020/0207501 A1 | 7/2020 | Urquhart et al. |
| 2020/0211291 A1 | 7/2020 | Miller et al. |
| 2020/0226758 A1 | 7/2020 | Carnes et al. |
| 2020/0250389 A1 | 8/2020 | Pulitzer et al. |
| 2020/0303044 A1 | 9/2020 | Stephen |
| 2020/0312038 A1 | 10/2020 | Samec et al. |
| 2020/0312437 A1 | 10/2020 | Wendland |
| 2020/0337631 A1 | 10/2020 | Sahin |
| 2020/0342679 A1 | 10/2020 | Soon-Shiong |
| 2020/0359891 A1 | 11/2020 | Fried et al. |
| 2020/0405257 A1 | 12/2020 | Samec et al. |
| 2020/0409159 A1 | 12/2020 | Samec et al. |
| 2021/0015583 A1 | 1/2021 | Avisar |
| 2021/0022810 A1 | 1/2021 | Mahfouz |
| 2021/0058485 A1 | 2/2021 | Devam et al. |
| 2021/0082554 A1 | 3/2021 | Kalia |
| 2021/0086989 A1 | 3/2021 | Luxford |
| 2021/0118029 A1 | 4/2021 | Koritala |
| 2021/0183507 A1 | 6/2021 | Shaya |
| 2021/0326474 A1 | 10/2021 | Sparks et al. |
| 2021/0327304 A1 | 11/2021 | Buras |
| 2021/0350883 A1 | 11/2021 | Li et al. |
| 2021/0358068 A1 | 11/2021 | Boszczyk et al. |
| 2022/0020236 A1* | 1/2022 | Luthra ................ G16H 50/80 |
| 2022/0101608 A1 | 3/2022 | Hu |
| 2022/0223282 A1 | 7/2022 | Ferro |
| 2022/0223300 A1 | 7/2022 | Ferro |
| 2022/0230747 A1 | 7/2022 | Ferro |
| 2022/0270752 A1 | 8/2022 | Ferro |
| 2022/0285007 A1 | 9/2022 | deHaan |

FOREIGN PATENT DOCUMENTS

| | | |
|---|---|---|
| KR | 10-2008-0012745 | 2/2008 |
| KR | 10-2012-0076652 | 7/2012 |
| KR | 10-2018-0068703 | 6/2018 |
| WO | WO 21/044064 | 3/2021 |
| WO | WO 21/171226 | 9/2021 |

OTHER PUBLICATIONS

Baruah, Basant, "Augmented reality and QR codes—What you need to know", accessed via wayback machine for Apr. 14, 2021, beaconstac blog.

Uber expands options for prescription delivery with ScriptDrop, Mar. 24, 2021, Uber.com Blog (Year: 2021).

Zheng, Lixia, "Using Augmented Reality with Interactive Narrative to Help Paediatric Patients Take Prescription Medication", 2020, University College London.

International search report and written opinion dated Jul. 11, 2022, in application No. PCT/US2022/021197.

* cited by examiner

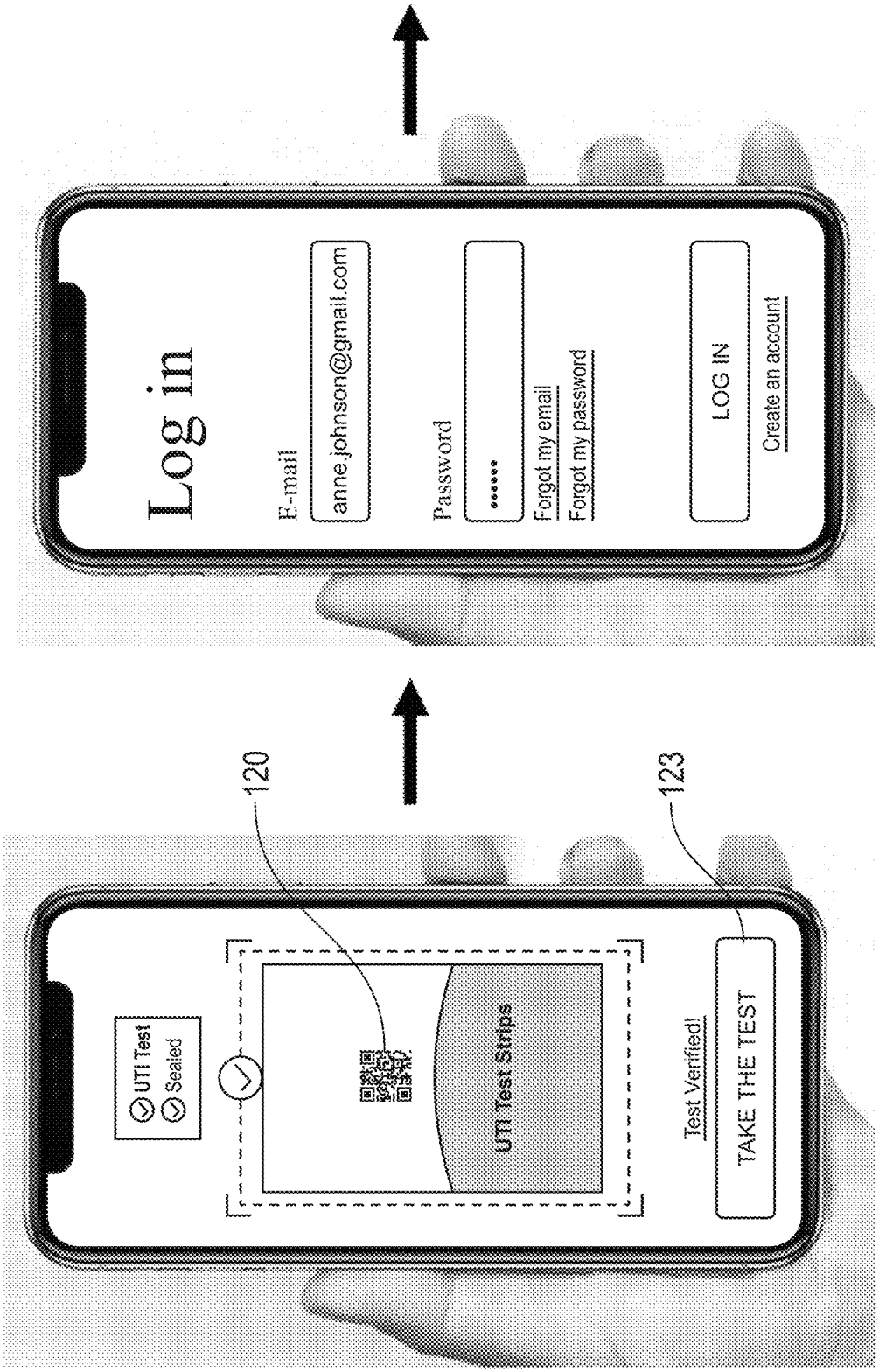

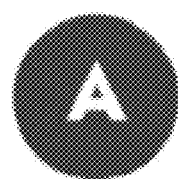
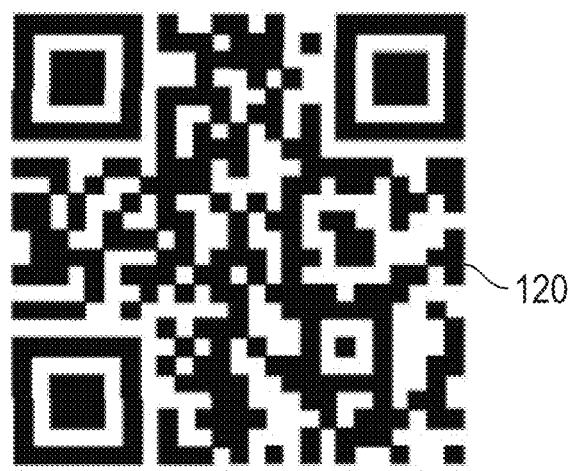
FIG. 11

DIGITALLY ENABLED AT-HOME RAPID TESTING

Third-party verified diagnostic testing with certified and validated result reporting powered by eMed. Digital health pass available via mobile app with negative test result.

- Negative test result is CDC accepted for travel.
- Meets CDC requirements for international air traveler U.S. reentry
- Same day Rx deliverly available if test result is positive.

Rx delivery via

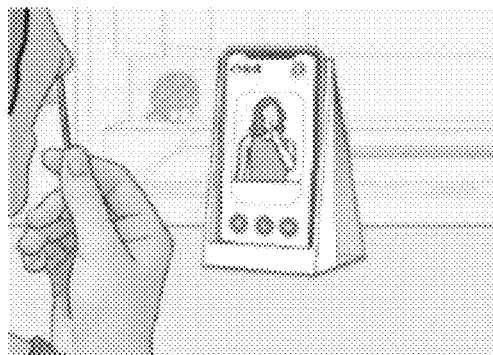

STEPS TO BEGIN TESTING

- SCAN YOUR CHOSEN TEST QR CODE.
- LOGIN OR SETUP YOUR ACCOUNT.
- BEGIN YOUR TEST PROCESS.
- VIEW TEST RESULTS.
- RECEIVE YOUR HEALTH PASS OR ADDITIONAL GUIDANCE.

(A) COVID-19 ANTIGEN TEST
(B) INFLUENZA A + B TEST
(C) STREP THROAT TEST
(D) UTI TEST

FIG. 13

✚ AT-HOME RAPID TEST KIT

Ⓐ COVID-19 ANTIGEN TEST*

Test provides a positive accuracy rate of 83.5% detection of SARS-CoV-2 protein antigen.

Ⓑ INFLUENZA A + B TEST**

Test detects influenza type A and type B.

Ⓒ STREP THROAT TEST**

Test detects Group A streptococcal antigen proteins.

Ⓓ UTI TEST**

Urine test that quickly detects whether nitrite and leukocytes are present.

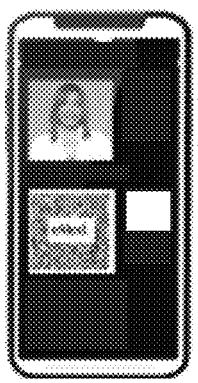

Third-party verified diagnostic testing with certified and validated result reporting powered by eMed. Digital health pass available via mobile app with negative test result is accepted for travel.

*Meets CDC requirements for international air traveler U.S. reentry.
**Some day Rx delivery available if test result is positive.

Rx delivery via

✚ CERTIFIED GUIDE PROCTORED     🕒 RESULTS IN MINUTES     ✓ CERTIFIED HEALTH PASS

FIG. 14

Please confirm the following

Are you free for the next 20 minutes?
- ◯ Yes
- ◯ No

Do you have your test available?
- ◯ Yes
- ◯ No

Is your test in an unopened package?
- ◯ Yes
- ◯ No

What is your date of birth?
[ DD / MM / YYYY ]

SUBMIT

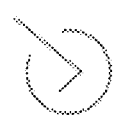
FIG. 28

FIG. 29

Join test session

Please enter your 6-digit meeting code below.

Meeting code

[Enter your meeting code]

SUBMIT CODE

DON'T HAVE A CODE? CLICK HERE

US 11,894,138 B2

REMOTE DIAGNOSTIC TESTING AND TREATMENT

PRIORITY APPLICATIONS

This application is a continuation of U.S. application Ser. No. 17/700,141, filed Mar. 21, 2022, which claims priority to U.S. Provisional Application No. 63/164,669, filed Mar. 23, 2021; U.S. Provisional Application No. 63/266,158, filed Dec. 29, 2021; U.S. Provisional Application No. 63/266,233, filed Dec. 30, 2021; U.S. Provisional Application No. 63/179,101, filed Apr. 23, 2021; U.S. Provisional Application No. 63/202,028, filed May 24, 2021; and U.S. Provisional Application No. 63/202,723, filed Jun. 22, 2022, each of which are incorporated herein by reference. Any and all applications for which a foreign or domestic priority claim is identified in the Application Data Sheet as filed with the present application are hereby incorporated by reference under 37 CFR 1.57.

FIELD

The present application relates to medical testing, such as remote health or diagnostic testing. Some embodiments relate to providing treatment in response to remotely-administered medical testing. Some embodiments relate to systems and methods for conducting remote health testing and diagnostics. Some embodiments relate to providing federated testing using a health testing and diagnostic platform. Some embodiments relate to first aid, first aid kits, diagnostic health testing kits, and to systems and method for providing first aid and/or diagnostic health testing guidance.

BACKGROUND

The use of telehealth to deliver healthcare services has grown consistently over the last several decades and has experienced very rapid growth in the last several years, particularly in light of the COVID-19 pandemic. Telehealth can include the distribution of health-related services and information via electronic information and telecommunication technologies. Telehealth can allow for long-distance patient and health provider contact, care, advice, reminders, education, intervention, monitoring, and remote admissions. Often, telehealth can involve the use of a user or patient's user device, such as a smartphone, tablet, laptop, personal computer, or other type of user device. For example, the user or patient can administer a health-related test remotely through the user device.

Remote or at-home health care testing and diagnostics can solve or alleviate some problems associated with in-person testing. For example, health insurance may not be required, travel to a testing site is avoided, and tests can be completed at a patient's convenience. However, at-home testing introduces various additional logistical and technical issues, such as guaranteeing timely test delivery to a testing user, providing test delivery from a patient to an appropriate lab, guaranteeing timely result reporting from the appropriate lab to a patient, ensuring test result verification and integrity, providing test result reporting to appropriate authorities and medical providers, providing treatments to a patient, and connecting patients with medical providers who may be needed to provide guidance and/or oversight of the testing procedures and results remotely.

SUMMARY

For purposes of this summary, certain aspects, advantages, and novel features of the invention are described herein. It is to be understood that not all such advantages necessarily may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

In one aspect, medical diagnostic kit includes a container and a plurality of medical diagnostic test kits located within the container, wherein each of the plurality of medical diagnostic test kits comprises equipment necessary to perform a particular self-administered medical diagnostic test, wherein the plurality of medical diagnostic test kits comprise at least a first medical diagnostic kit adapted to facilitate user completion of a first medical diagnostic test and a second medical diagnostic kit adapted to facilitate user completion of a second medical diagnostic test different from the first medical diagnostic test, and wherein the container comprises a machine-readable code located on an external surface of the container.

The medical diagnostic kit may include one or more of the following features in any combination: wherein at least one of the plurality of medical diagnostic test kits comprises one of: a Covid-19 test kit, a UTI test kit, a drug test kit, a syphilis test kit, a streptococcal pharyngitis test kit, an influenza test kit, and a sexually transmitted disease (STD) test kit; wherein the machine-readable code configured to be imaged by a camera of a portable user computing device to enable providing a fiducial point from which a coordinate frame for an augmented reality presentation can be established using the camera and a display of the portable user computing device, and causing the portable user computing device to display a user-selectable graphic on the display of the portable user computing device that, when selected by a user, causes a software application stored on the portable user computing device to access a provider webpage that enables initiation of the augmented reality presentation that includes display of augmented reality content relating to the plurality of medical diagnostic test kits; wherein the augmented reality content relating to the plurality of medical diagnostic test kits comprises information about each of the particular medical diagnostic tests; wherein the augmented reality content relating to the plurality of medical diagnostic test kits comprises information about various steps in a testing process for each of the particular medical diagnostic tests; wherein the machine-readable code is an QR code; wherein the machine-readable code is an augmented reality QR code; wherein each of the plurality of medical diagnostic test kits comprises a respective machine-readable code located on an external surface of a package of the medical diagnostic test kit that, when scanned by the portable user computing device, causes the portable user computing device to display information relating to the particular medical diagnostic test and/or instructions on how to perform the particular medical diagnostic test on the display of the portable user computing device; wherein at least one of the respective machine-readable codes comprises a QR code; wherein the machine-readable code configured to be imaged by a camera of a portable user computing device to enable providing a fiducial point from which a coordinate frame for an augmented reality presentation can be established using the camera and a display of the portable user computing device, and causing the portable user computing device to display a user-selectable graphic on the display of the portable user computing device that, when selected by a user, causes a software application stored on the portable user computing device to access a provider webpage that enables establishment of a live video feed with a live proctor, wherein the proctor is remotely located from the user device; and/or other features as described herein.

In another aspect, a method for medical diagnostic testing, includes: providing a user with a medical diagnostic test kit container, wherein a plurality of medical diagnostic test kits are located within the container, wherein each of the plurality of medical diagnostic test kits comprises equipment necessary to perform a particular self-administered medical diagnostic test, wherein the plurality of medical diagnostic test kits comprise at least a first medical diagnostic kit adapted to facilitate user completion of a first medical diagnostic test and a second medical diagnostic kit adapted to facilitate user completion of a second medical diagnostic test different from the first medical diagnostic test, and wherein the container comprises a machine-readable code located on an external surface of the container.

The method can include one or more of the following features in any combination: wherein at least one of the plurality of medical diagnostic test kits comprises one of: a Covid-19 test kit, a UTI test kit, a drug test kit, a syphilis test kit, a streptococcal pharyngitis test kit, an influenza test kit, and a sexually transmitted disease (STD) test kit; wherein the machine-readable code configured to be imaged by a camera of a portable user computing device, the method further comprising providing a fiducial point from which a coordinate frame for an augmented reality presentation can be established using the camera and a display of the portable user computing device, and causing the portable user computing device to display a user-selectable graphic on the display of the portable user computing device that, when selected by a user, causes a software application stored on the portable user computing device to access a provider webpage that enables initiation of the augmented reality presentation that includes display of augmented reality content relating to the plurality of medical diagnostic test kits; wherein the augmented reality content relating to the plurality of medical diagnostic test kits comprises information about each of the particular medical diagnostic tests; wherein the augmented reality content relating to the plurality of medical diagnostic test kits comprises information about various steps in a testing process for each of the particular medical diagnostic tests; wherein the machine-readable code is an QR code; wherein the machine-readable code is an augmented reality QR code; wherein each of the plurality of medical diagnostic test kits comprises a respective machine-readable code located on an external surface of a package of the medical diagnostic test kit that, when scanned by the portable user computing device, causes the portable user computing device to display information relating to the particular medical diagnostic test and/or instructions on how to perform the particular medical diagnostic test on the display of the portable user computing device; wherein at least one of the respective machine-readable codes comprises a QR code; wherein the machine-readable code configured to be imaged by a camera of a portable user computing device, the method further comprising providing a fiducial point from which a coordinate frame for an augmented reality presentation can be established using the camera and a display of the portable user computing device, and causing the portable user computing device to display a user-selectable graphic on the display of the portable user computing device that, when selected by a user, causes a software application stored on the portable user computing device to access a provider webpage that enables establishment of a live video feed with a live proctor; and/or other features as described herein.

In another aspect, an augmented-reality (AR)-enabled first aid kit, comprises a container; and a plurality of first aid items located within the container, wherein each of the plurality of first aid items comprises equipment necessary to perform a first aid, a machine-readable code located on an external surface of the container, the machine-readable code configured to be imaged by a camera of a portable user computing device to enable providing a fiducial point from which a coordinate frame for an augmented reality presentation can be established using the camera and a display of the portable user computing device, and causing the portable user computing device to display a user-selectable graphic on the display of the portable user computing device that, when selected by a user, causes a software application stored on the portable user computing device to access a provider webpage that enables initiation of the augmented reality presentation that includes display of AR content relating to the plurality of first aid items.

The AR-enabled first aid kit can include one or more of the following features in any combination: wherein the AR content comprises information about various first aid steps associated with providing first aid using one or more of the plurality of first aid items; wherein the AR content comprises information about diagnosis of a condition to be treated with one or more of the plurality of first aid items; wherein the machine-readable code is a QR code; wherein the machine-readable code is an augmented reality QR code; wherein each particular first aid item of the plurality of first aid items comprises a respective machine-readable code located on an external surface of a package of the particular first aid item that, when scanned by the portable user computing device, causes the portable user computing device to display information relating to the particular first aid item and/or instructions on how to perform first aid with the particular first aid item on the display of the portable user computing device; wherein at least one of the respective machine-readable codes comprises a QR code; and/or other features as described herein.

In another aspect, a system for facilitating first aid using a first aid kit comprising a container and a plurality of first aid items. The system comprises an electronic storage medium comprising computer-executable instructions and one or more processors in electronic communication with the electronic storage medium and configured to execute the computer-executable instructions in order to: receive, by the system, a request for first aid guidance, wherein the request for first aid guidance is provided by a user on a user interface on a user device; receive, by the system, one or more indications of a condition to be treated, wherein the one or more indications of the condition to be treated are provided by the user using the user device; determining, by the system, whether the condition to be treated is treatable with the first aid kit; based on a determination that the condition to be treated is not treatable with the first aid kit, providing, by the system, a user instruction to seek professional medical attention and a user-selectable option for connecting the user to emergency services, the user instruction and the user-selectable option provided on a display of the user device; and based on a determination that the condition to be treated is treatable with the first aid kit, providing, by the system, first aid instructions for treating the condition using first aid materials of the first aid kit.

The system can include one or more of the following features in any combination: wherein the one or more indications of a condition to be treated comprise an image captured using a camera of the user device, wherein the image is transmitted to the system over a network; providing, by the system, information that is superimposed on the image, the information comprising the first aid guidance; causing, by the system, the image with the superimposed information to be displayed on a display of the user device; receiving, by the system, indications of the first aid items in the first aid kit, wherein the indications are provided by the user on the user device, and wherein the determination that whether the condition to be treated is treatable with the first aid kit is based on the indications of the first aid items in the first aid kit; wherein the indications of the first aid items in the first aid kit are determined based on one or more images of the first aid kit captured by a camera of the user device; determining, by the system, at least some of the first aid items within the first aid kit based on machine-readable codes includes on the at least some of the first aid items; wherein the machine-readable codes comprise QR codes; wherein the indications of the first aid items in the first aid kit are determined based on providing, by the system, a list of first aid items to be displayed on the display of the user device, and receiving, by the system, a selection of the listed items, wherein the selection is made by the user on the user device; wherein the indications of the first aid items in the first aid kit are determined based on receiving, by the system, a spoken list of first aid items available to the user, wherein the spoken list is generated by the user and recorded on a microphone of the user device; and/or other features as described herein.

In another aspect, a method for facilitating first aid using a first aid kit comprising a container and a plurality of first aid items comprises: receiving a request for first aid guidance, wherein the request for first aid guidance is provided by a user on a user interface on a user device; receiving one or more indications of a condition to be treated, wherein the one or more indications of the condition to be treated are provided by the user using the user device; determining whether the condition to be treated is treatable with the first aid kit; based on a determination that the condition to be treated is not treatable with the first aid kit, providing a user instruction to seek professional medical attention and a user selectable option for connecting the user to emergency services, the user instruction and the user-selectable option provided on a display of the user device; and based on a determination that the condition to be treated is treatable with the first aid kit, providing first aid instructions for treating the condition using first aid materials of the first aid kit.

The method can include one or more of the following features in any combination: receiving an image captured using a camera of the user device, wherein the image is transmitted over a network; analyzing the image to determine the one or more indications of a condition to be treated; providing information that is superimposed on the image, the information comprising the first aid guidance; causing the image with the superimposed information to be displayed on the display of the user device; determining contents of the first aid kit based on one or more images of the first aid kit captured by a camera of the user device; and/or other features as described herein.

In another aspect a computer-implemented method includes determining, by a computer system, a test result of a user, wherein the test result based on a self-administered diagnostic medical test; based upon a determination that the test result is positive, wherein a positive test result indicates that treatment is advisable: generating, by the computer system, a prescription questionnaire, wherein the prescription questionnaire is transmitted to the user over an electronic network and displayed to the user on a user device; receiving, by the computer system, user inputs in response to the prescription questionnaire, wherein the user inputs are inputted by the user on the user device and transmitted to the computer system over the electronic network; transmitting, by the computer system, the user inputs and the test result to a prescription provider, wherein the user inputs are transmitted over the electronic network and displayed to the prescription provider on a provider device, and wherein the prescription provider determines at least one prescription for the user based on the user inputs and the test result; receiving, by the computer system, prescription information based on the at least one prescription determined by the prescription provider, wherein the prescription information is transmitted to the computer system over the electronic network; determining, by the computer system, a delivery partner based on a location of the user and a location of the prescription provider, a delivery partner for delivering the prescription to the user; and generating, by the computer system, delivery instructions for the delivery partner, wherein the delivery instructions are configured to facilitate the delivery partner obtaining the prescription from the prescription provider and delivering the prescription to the user; and transmitting, by the computer system, the delivery instructions to the delivery partner, wherein the delivery instructions are transmitted over the electronic network.

The method can include one or more of the following features in any combination: wherein the self-administered medical diagnostic test is taken by the user using a testing platform provided by the computer system that provides a video conference connection between the user and a proctor; determining, by the computer system, the prescription questionnaire based on the test result and a database of available medications; wherein the prescription questionnaire is further based on a user profile, wherein the user profile is generated based on an interaction between the user and a testing platform provided by the computer system that facilitates the self-administered medical diagnostic test; determining, by the computer system, if more than a threshold period of time has passed since the user obtained the positive test result; wherein the user device comprises a smartphone; wherein the user device comprises a GPS module, and determining the location of the user is based at least in part on an output of the GPS module; generating a prescription release code, wherein the prescription release code comprises one or more of a code, a barcode, and a QR code; transmitting the prescription release code to the delivery partner, whereby the delivery partner obtains the prescription based on the prescription release code; generating, by the computing system, an alert notification for the user when the delivery partner obtains the prescription; and/or other features as described herein.

In another aspect, a computer system comprising an electronic storage medium comprising computer-executable instructions and one or more processors in electronic communication with the electronic storage medium and configured to execute the computer-executable instructions in order to: determine, by a computer system, a test result of a user, wherein the test result based on a self-administered diagnostic medical test; based upon a determination that the test result is positive, wherein a positive test result indicates that treatment is advisable: transmit, by the computer system, a prescription questionnaire to the user, wherein the prescription questionnaire is transmitted to the user over an electronic network and displayed to the user on a user device; receive, by the computer system, user inputs in response to the prescription questionnaire, wherein the user inputs are inputted by the user on the user device and transmitted to the computer system over the electronic network; transmit, by the computer system, the user inputs and the test result to a prescription provider, wherein the user inputs are transmitted over the electronic network and displayed to the prescription provider on a provider device, and wherein the prescription provider determines at least one prescription for the user based on the user inputs and the test result; receive, by the computer system, prescription information based on the at least one prescription determined by the prescription provider, wherein the prescription information is transmitted to the computer system over the electronic network; determine, by the computer system, a delivery partner based on a location of the user and a location of the prescription provider, a delivery partner for delivering the prescription to the user; and generate, by the computer system, delivery instructions for the delivery partner, wherein the delivery instructions are configured to facilitate the delivery partner obtaining the prescription from the prescription provider and delivering the prescription to the user; and transmit, by the computer system, the delivery instructions to the delivery partner, wherein the delivery instructions are transmitted over the electronic network.

The computer system can include one or more of the following features in any combination: wherein the self-administered medical diagnostic test is taken by the user using a testing platform provided by the computer system that provides a video conference connection between the user and a proctor; determining, by the computer system, the prescription questionnaire based on the test result and a database of available medications; wherein the prescription questionnaire is further based on a user profile, wherein the user profile is generated based on an interaction between the user and a testing platform provided by the computer system that facilitates the self-administered medical diagnostic test; determining, by the computer system, if more than a threshold period of time has passed since the user obtained the positive test result; wherein the user device comprises a smartphone; wherein the user device comprises a GPS module, and determining the location of the user is based at least in part on an output of the GPS module; generating a prescription release code, wherein the prescription release code comprises one or more of a code, a barcode, and a QR code; transmitting the prescription release code to the delivery partner, whereby the delivery partner obtains the prescription based on the prescription release code; generating, by the computer system, an alert notification for the user when the delivery partner obtains the prescription; and/or other features as described herein.

In another aspect, a computing system for a proctored examination platform for a medical diagnostic test is described. The computing system comprises an electronic storage medium storing computer-executable instructions and one or more processors configured to execute the computer-executable instructions for implementing the proctored examination platform for the medical diagnostic test by: receiving, by the computing system, a user request from a user computing device of a user for a proctored examination for a medical diagnostic test; generating, by the computing system, display data for a display of a proctor device, the display data configured to display to a non-physician proctor a phase indicator showing a current phase of the user of the medical diagnostic test; establishing, by the computing system, an electronic video conference session between the proctor device and the user computing device; receiving, by the computing system, a positive medical diagnostic indicator from the proctor device; dynamically verifying, by the computer system, the positive medical diagnostic indicator by analyzing monitored video frame data associated with the electronic video; based on the positive medical diagnostic indicator, generating, by the computing system, user display data for displaying medical content data about a positive result for the medical diagnostic test and a user prompt for determining whether the user desires to order prescription drugs for treatment responsive to the positive result for the medical diagnostic test; receiving, by the computing system, a request to order the prescription drugs from the user computing device; and generating, by the computing system, physician display data for displaying a display of a physician device, the physician display data configured to display and a physician prompt for generating a prescription for ordering the prescription drugs for treatment responsive to the positive result for the medical diagnostic test.

The computing system can include one or more of the following features in any combination: transmitting, by the computing system, the prescription for the prescription drugs to a pharmacy device; generating, by the computing system, courier data for display on a courier computing device, the courier display data configured to display a prescription release code and directions to a pharmacy fulfilling the prescription; transmitting, by the computing system, the courier data to the courier computing device; wherein the prescription release code is a QR code; receiving, by the computing system, a pick-up confirmation that the prescription drug was picked up by the courier from the pharmacy device; generating, by the computing system, based on the pick-up confirmation, supplemental courier data for the display of the courier computing device, the supplemental courier display data configured to cause to display directions to the user; receiving, by the computing system, a delivery confirmation that the prescription drug was delivered by the courier from the user computing device; wherein dynamically verifying the positive medical diagnostic indicator comprises verifying that the medical diagnostic test was administered by the user without abnormalities by analyzing monitored video frame data associated with the electronic video conference session for abnormalities to automatically determine from the analyzed monitored video frame data that a swab used by the user during the medical diagnostic test was inserted into a nasal cavity at a proper insertion depth; wherein dynamically verifying the positive medical diagnostic indicator comprises verifying that the medical diagnostic test was administered by the user without abnormalities by analyzing monitored video frame data associated with the electronic video conference session for computer vision analysis of a test result portion; based at least in part on the positive medical diagnostic indicator and the request to order the prescription drugs, generating a prescription questionnaire; transmitting the prescription questionnaire to the user device; receiving, by the computer system, user responses to the prescription questionnaire inputted by the user on the user device; wherein the medical diagnostic data about the positive medical diagnostic indicator for the medical diagnostic test includes information derived the user responses; wherein a current location of a courier is determined by a GPS unit in the courier computing device; wherein a current location of the user is determined by a GPS unit in the user computing device; and/or other features as described herein.

In another aspect, a method for a proctored examination platform for a medical diagnostic test comprises: receiving a user request from a user computing device of a user for a proctored examination for a medical diagnostic test; generating display data for a display of a proctor device, the display data configured to display to a non-physician proctor a phase indicator showing a current phase of the user of the medical diagnostic test; establishing an electronic video conference session between the proctor device and the user computing device; receiving a positive medical diagnostic indicator from the proctor device; dynamically verifying the positive medical diagnostic indicator by analyzing monitored video frame data associated with the electronic video; based on the positive medical diagnostic indicator, generating user display data for displaying medical content data about a positive result for the medical diagnostic test and a user prompt for determining whether the user desires to order prescription drugs for treatment responsive to the positive result for the medical diagnostic test; receiving a request to order the prescription drugs from the user computing device; and generating physician display data for displaying a display of a physician device, the physician display data configured to display and a physician prompt for generating a prescription for ordering the prescription drugs for treatment responsive to the positive result for the medical diagnostic test.

The method can include one or more of the following features in any combination: transmitting the prescription for the prescription drugs to a pharmacy device; generating courier data for display on a courier computing device, the courier display data configured to display a prescription release code and directions to a pharmacy fulfilling the prescription; transmitting the courier data to the courier computing device; wherein the prescription release code is a QR code; receiving a pick-up confirmation that the prescription drug was picked up by the courier from the pharmacy device; generating based on the pick-up confirmation, supplemental courier data for the display of the courier computing device, the supplemental courier display data configured to cause to display directions to the user; receiving a delivery confirmation that the prescription drug was delivered by the courier from the user computing device; wherein dynamically verifying the positive medical diagnostic indicator comprises verifying that the medical diagnostic test was administered by the user without abnormalities by analyzing monitored video frame data associated with the electronic video conference session for abnormalities to automatically determine from the analyzed monitored video frame data that a swab used by the user during the medical diagnostic test was inserted into a nasal cavity at a proper insertion depth; wherein dynamically verifying the positive medical diagnostic indicator comprises verifying that the medical diagnostic test was administered by the user without abnormalities by analyzing monitored video frame data associated with the electronic video conference session for computer vision analysis of a test result portion; based at least in part on the positive medical diagnostic indicator and the request to order the prescription drugs, generating a prescription questionnaire; transmitting the prescription questionnaire to the user device; receiving user responses to the prescription questionnaire inputted by the user on the user device; wherein the medical diagnostic data about the positive medical diagnostic indicator for the medical diagnostic test includes information derived the user responses; wherein a current location of a courier is determined by a GPS unit in the courier computing device; wherein a current location of the user is determined by a GPS unit in the user computing device; and/or other features as described herein.

These and other features and advantages of the systems and methods for providing first aid guidance will be described in more detail below.

BRIEF DESCRIPTION OF THE DRAWINGS

The drawings are provided to illustrate example embodiments and are not intended to limit the scope of the disclosure. A better understanding of the systems and methods described herein will be appreciated upon reference to the following description in conjunction with the accompanying drawings, wherein:

FIGS. 10A-10H illustrate a series of example screen displays that can be displayed to a user to guide the user through the steps of administering an at-home urinary tract infection test according to some embodiments described herein.

FIG. 11 illustrates an example of a graphic label (including a machine-readable code) that can be printed on or adhered to an external surface of a medical diagnostic test kit within the medical diagnostic test kit container or package of FIG. 1 according to some embodiments described herein.

FIGS. 13 and 14 are examples of graphic labels or inserts that may be provided on or inside the medical diagnostic test kit container or package of FIG. 1 according to some embodiments described herein.

FIG. 28 illustrates an example pre-testing virtual waiting room according to some embodiments described herein.

FIG. 29 illustrates an example unique code submission interface according to some embodiments described herein.

DETAILED DESCRIPTION

Figure 1:
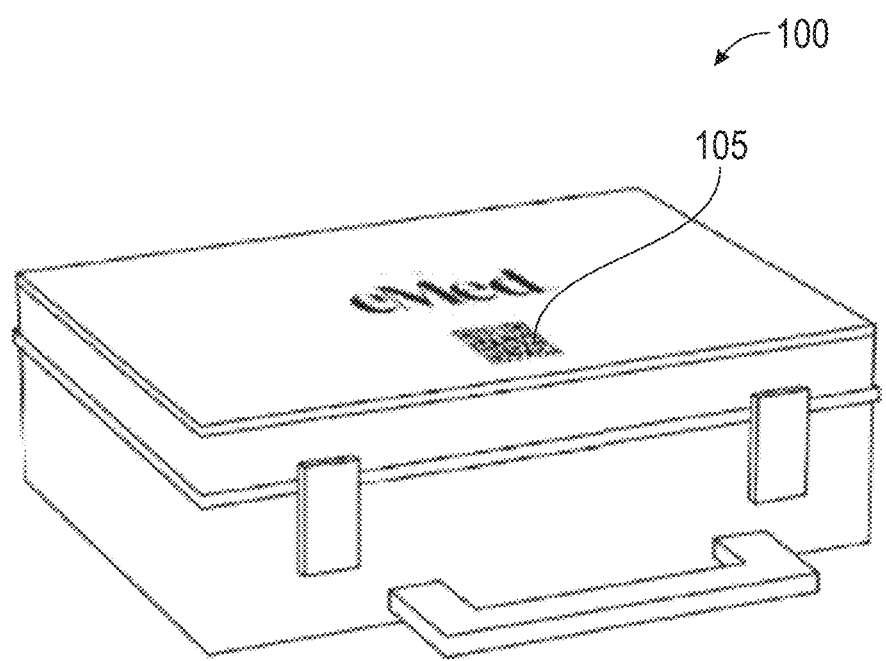
FIG. 1 illustrates an example of an at-home medical diagnostic test kit container or package having a machine-readable code that can be scanned to initiate an augmented reality experience according to some embodiments described herein.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present technology. The section headings used herein are merely provided to enhance readability and are not intended to limit the scope of the embodiments disclosed in a particular section to the features or elements disclosed in that section.

Some embodiments herein are directed to a medical diagnostic test kit container or package that functions similar to a first aid kit but includes several at-home medical diagnostic test kits of different types that a household (e.g., an individual or family), care facility or assisted living center, or other group or individual, could use to complete at-home medical testing. The diagnostic test kit container or package may be purchased from an e-commerce provider or a retail store without requiring a prescription and stored and used on demand as needs arise for diagnostic or medical testing. For example, if an individual is feeling sick or experiencing symptoms of a medical condition (such as COVID-19, influenza, or urinary tract infection), the individual may open the medical diagnostic test kit container and select an appropriate at-home diagnostic test and complete the at-home medical diagnostic test. The at-home medical diagnostic tests may be self-administered, administered by another individual in the household or care facility, or a health care provider.

Of course, the medical diagnostic test kits may also be used even in instances where no symptoms are being experienced, as desired. In addition, if a negative screening test is required prior to travel or employment (such as a negative COVID-19 test or a negative drug test), the medical diagnostic test kit container may include screening tests that are certified and accepted as proof by government agencies, travel companies and institutions (such as airlines, cruise ship companies), restaurants, gyms, fitness centers, hospitals, other retail establishments, and employers that may require proof of negative diagnostic tests.

Different medical diagnostic test kit containers or packages may include various types and numbers of tests designed for different individuals, households, care facilities, etc. A label on the diagnostic test kit container may indicate the types and numbers of medical diagnostic tests in the particular container or package. In addition, supplemental medical diagnostic test kits may be ordered (e.g., via an e-commerce website or platform) when needed to restock supply. Certain medical diagnostic test kits may require a prescription or approval from a health care provider prior to ordering. Other medical diagnostic test kits may be purchased without any prescription or approval at the time of purchase.

The medical diagnostic test kit container or package may include a machine-readable code located on an external surface of the box that can be scanned by a camera of a user device (such as a personal computer, a cellular phone, a smartphone, a laptop, a tablet computer, smart glasses, an e-reader device, an audio player, or another device capable of connecting to and communicating over a network, whether wired or wireless) to initiate an augmented reality interactive experience for user computing devices that have augmented reality capability (e.g., AR-compatible smartphone, tablet, or smart glasses). The augmented reality experience can include, for example, interactive displays that show the types of medical diagnostic test kits included in the medical diagnostic test kit container or package, an overview of the steps required for each of the medical diagnostic tests, the materials (e.g., test equipment) included in the medical diagnostic test kits, and a guided step-by-step process to facilitate completion of each of the medical diagnostic tests. The augmented reality experience may help users visualize and complete the steps of an at-home test more easily and provide an enhanced user experience.

A remote health testing and diagnostic platform (e.g., a digital point-of-care platform operated by a commercial entity, such as eMed based in Florida) may also be used to facilitate coordination with proctors to enable certification of certain of the diagnostic tests, to facilitate ordering and delivery of prescription medicine that may be helpful to treat a medical condition identified by a medical diagnostic test in the medical diagnostic test kit package, to facilitate generation of a certification or pass that can be displayed as proof of a negative screening test (such as a negative COVID-19 test), to facilitate re-ordering or supplemental ordering of medical diagnostic test kits when inventory of a particular medical diagnostic test kit type in the medical diagnostic test kit container or package is low or out of stock, and/or to generate pre-screening surveys to determine whether or not it makes sense for the user to actually complete a particular medical diagnostic test.

At-home medical testing provides both safety and convenience to patients and medical providers. In-person visits by individuals with infectious diseases endangers both medical professionals, as well as anyone who encounters the individuals on their way to the in-person visit or in the waiting room. At-home testing does not involve personal contact between the patient and any other individuals who may otherwise be at risk. Furthermore, at-home testing is simply more convenient, as neither medical providers nor patients need to leave the safety or comfort of their home in order to administer a test using remote testing platforms.

Additionally, because of advancements in medical and logistics technology, especially as described herein, at-home testing can now be extremely fast. In some cases, medical diagnostic tests can be administered and read within seconds. Other tests may require a cure time before being read or may require delivery to a laboratory to receive results, but results can still be received within days in most cases.

Applications for at-home medical testing are abundant. For example, at-home testing can be used by travelers in any location to ensure that the traveler is healthy before and/or after arriving at a destination, without having to locate medical care in an unfamiliar locale. Furthermore, at-home testing may prevent the spread of infectious diseases by providing travelers knowledge of when to quarantine or avoid traveling altogether, and to avoid bringing home an infectious disease. At-home testing may also be useful for sensitive individuals such as the elderly and children. At-home testing may provide a better experience for such sensitive individuals, especially in cases in which the testing procedure is uncomfortable or invasive. At-home testing can mean that the test is done in a safe, comfortable, and familiar environment, so sensitive individuals may feel less stressed and worried during their test, allowing testing to proceed more smoothly. In some instances, at-home testing can be performed in a user's home, although this need not be the case in all instances. For example, as used herein, at-home testing can refer to testing performed in other locations outside the home, such as in hotel rooms, airports, or other remote locations where access to an in-person healthcare provider is not available or desirable. Another consideration for at-home testing is privacy. At-home testing can be private and discreet, which is ideal for high-profile individuals or sensitive individuals who want to get tested without leaving their homes. Also, accessibility considerations favor at-home testing. At-home testing is ideal for anyone who has transportation issues or mobility/accessibility considerations.

In some embodiments, the remote health testing and diagnostic platform may facilitate administration of a medical diagnostic test to a patient with the guidance of a proctor. In some embodiments, the proctor may comprise uncertified personnel, certified medical personnel, and/or a proctor for monitoring an algorithm such as computer software, which may administer a medical diagnostic test. In some embodiments, the computer software is not administering the medical diagnostic test but rather is monitoring the medical diagnostic test for abnormalities or deviations or inconsistencies in the administration or performance or procedure of the medical diagnostic test that is being administered by the uncertified personnel and/or certified medical personnel and/or medical personnel and/or the like. In some embodiments, the patient may be provided with step-by-step instructions for test administration by the proctor within a testing environment. The platform may display unique, dynamic testing interfaces to the patient and proctor to ensure proper testing protocols and/or accurate test result verification. The displays may be enhanced with augmented reality content overlaid on images obtained by cameras of a user device, such as a smartphone or tablet, to enhance the user experience and reduce user compliance errors.

In some embodiments, the platform may provide a testing environment comprising a private communication channel (such as over the internet) between a proctor and a patient. In some embodiments, the testing environment may comprise one or more unique user interfaces that may facilitate seamless testing, submission and verification. In some embodiments, the platform may provide for automatic transmission of verified test results to users, relevant authorities, and third parties. In some embodiments, the platform may generate a unique health card or passport, which may provide an easily accessible and understandable testing summary for a patient and/or third parties.

In some embodiments, the platform may also be configured to provide urgent care to patients in need by collecting symptom and medical data from patients and providing such data to relevant medical professionals and pharmacies. In some embodiments, the platform may facilitate diagnosis of a patient by a third-party medical provider and fulfillment and even delivery of a drug prescription by a third-party pharmacy and a third-party courier service, without any of the parties having direct (e.g., physical or in person) contact.

At-Home Medical Diagnostic Test Kit Container

Figure 42:
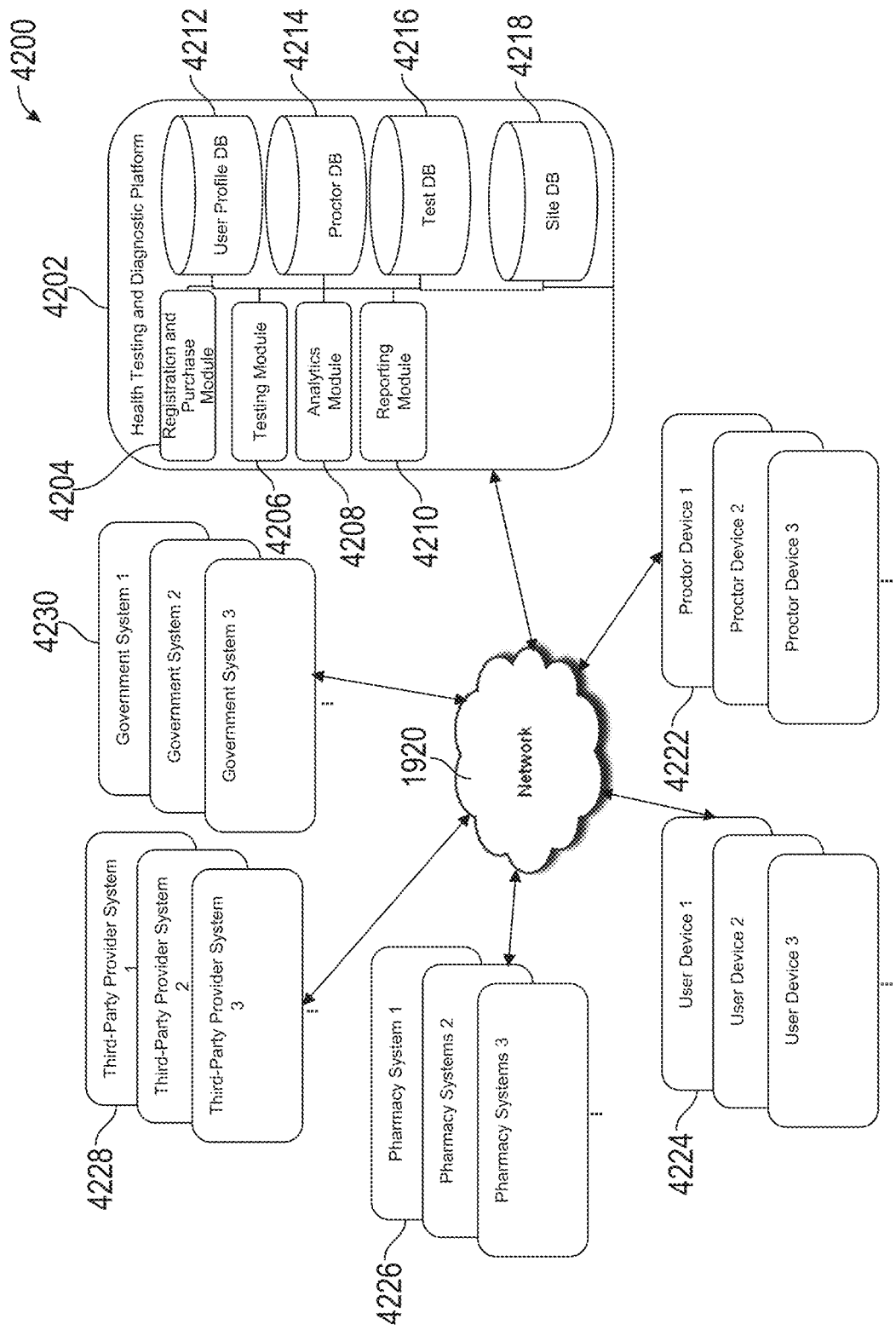
FIG. 42 is a block diagram illustrating an example embodiment of a computer system configured to run soft-

FIG. 1 illustrates an example of an at-home medical diagnostic test kit container or package 100 that may be utilized in conjunction with a remote health testing and diagnostic platform (e.g., platform 4202 shown in FIG. 42). The medical diagnostic test kit container or package 100 may function similar to a first aid kit but, instead of including bandages, gauze pads, wraps, ointments, or other typical first aid kit supplies, includes a plurality of medical diagnostic test kits of various types that can be used to perform at-home or self-administered medical diagnostic tests. The diagnostic test kit container 100 may comprise a box, package, canister, or other container adapted to hold and store contents. The diagnostic test kit container 100 may be made of plastic, cardboard, metal, polymeric, or other material.

The medical diagnostic test kit container 100 may include one or more graphics (e.g., images and/or alphanumeric text). The graphics may be printed on an exterior surface of the medical diagnostic test kit container 100 or may be printed on an adhesive label or sticker that is adhered to the exterior surface of the medical diagnostic test kit container 100. The graphics may include, among other things, a machine-readable code 105 (e.g., QR code, AR code, bar code, datamatrix code, PDF417 code, Aztec code) that, when scanned or imaged by a user device, such as a mobile computing device having one or more built-in cameras, causes the user device to provide information about the collection of medical diagnostic test kits within the medical diagnostic test kit container 100 as a whole, about the individual medical diagnostic test kits, and/or about the medical diagnostic tests themselves. In one implementation, the machine readable code 105 is an AR code configured to facilitate display of augmented reality content. In some embodiments, the machine readable code 105 may correspond to a graphic (e.g., an image, logo, etc.) that an application or web app may recognize using one or more computer vision techniques to provide one or more pieces of the aforementioned information.

Although the machine-readable code 105 is shown located on a top external surface of the medical diagnostic test kit container 100 in a central location, it should be appreciated that other locations for the machine-readable code 105 are also contemplated (e.g., other locations on the top external surface, locations on a different external surface, internal locations). In addition, there may be multiple instances of the machine-readable code 105 at various locations on the medical diagnostic test kit container 100.

In accordance with various embodiments, the medical diagnostic test kits that may be included in the medical diagnostic test kit container 100 include, but are not limited to, the following:

| Test Name | Condition(s) | Test Mechanism | Sample Type |
| --- | --- | --- | --- |
| COVID-19 Rapid Test Kit | SARS-CoV-2 | Antigen | Nasal Swab (Anterior) |
| UTI Emergency Kit | UTI | Analyte | Urine |
| Drug Test | Drug | Antigen | Saliva |
| Syphilis Rapid Test Kit | STD/STI | Analyte | Finger Prick |
| COVID-19 All-In-One Test Kit | SARS-CoV-2 | PCR (molecular) | Nasal Swab (Anterior) |
| Strep | Strep A | Immunolateral Flow Cell | Throat Swab |
| Flu | Influenza A/B | Immunolateral Flow Cell | Nasal Swab (Anterior) |
| UTI Test Strips | UTI | Analyte | Urine |
| STD Multitest | STD/STI | LAMP | Urine |
| Sexual Health Multi-Test Pack | STD/STI | Lateral immunoflow | Multiple - blood or fluid sample |
| IGM & IGG COMBO COVID-19 ANTIBODY | SARS-CoV-2 | Antibody | Finger Prick |
| Gonorrhea Rapid Test Kit | STD/STI | Analyte | Genital Swab |
| Hepatitis B Rapid Test Kit | STD/STI | Analyte | Finger Prick |
| Chlamydia Rapid Test Kit | STD/STI | Analyte | Genital Swab |

The medical diagnostic test kits may include test kits configured for diagnosing or testing various medical conditions (which may be symptomatic conditions or asymptomatic conditions) and may involve various different test mechanisms (e.g., analyte tests, antibody tests, polymerase chain reaction (PCR) tests, lateral flow immunoassay tests, loop mediated isothermal amplification (LAMP) assay tests, etc.), and means of obtaining diagnostic samples (e.g., urine, finger prick, saliva, nasal swab, genital swab, throat swab, etc.).

Some of the medical diagnostic test kits may be administered when an individual is not feeling well or is experiencing symptoms of a suspected medical condition. Some of the medical diagnostic test kits, such as COVID-19 test kits or drug test kits, may be administered on-demand when an individual is required to show proof of a negative diagnostic test (e.g., prior to travel or entry into a public event or retail or commercial building, prior to employment or periodically during employment for verification, prior to attending school or college, etc.).

In several implementations, the machine-readable code 105, when scanned by a camera of the user device (e.g., using a camera application or a QR code scanner application of the user device), can direct the user (e.g., via a Web browser application stored on the user device) to a proprietary platform website or Web application running on one or more servers, or a software application stored on the user device, that can provide the user with an option to initiate an augmented reality experience to explore the contents of the medical diagnostic test kit container 100 using the user device without even opening the medical diagnostic test kit container 100.

Figure 2A:
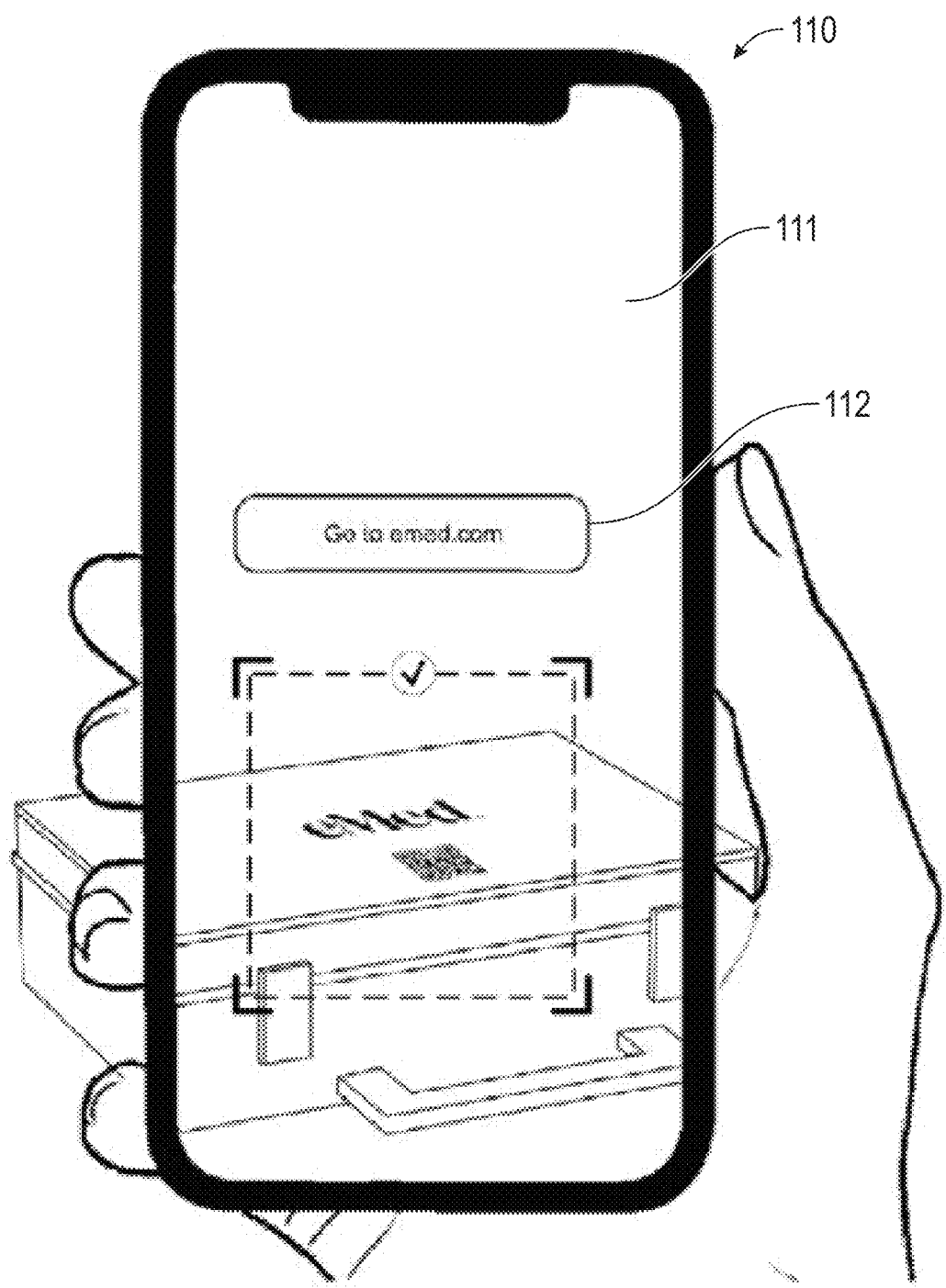
FIG. 2A illustrates an example of a user scanning the machine-readable code on the medical diagnostic test kit container of FIG. 1 using a camera of a user device (such as a mobile phone), as well as an example graphical user interface shown on a display of the user device after the machine-readable code has been scanned, according to some embodiments described herein.

FIG. 2A illustrates an example of an individual scanning the machine-readable code 105 on the medical diagnostic test kit container 100 using a built-in camera (e.g., rear-facing camera) of a user device 110 (such as a mobile phone, smartphone, tablet, laptop, e-Reader device, smartwatch, smart glasses). The real-time video images obtained by the camera(s) of the user device 110 can be displayed on a display screen 111 of the user device 110. As shown, a graphical user interface may be presented on the display screen 111 that allows the user to choose (by interacting with an image and/or text hyperlink or button 112 on the display screen 111) to navigate to a proprietary platform website using a Web browser application stored on the user device 110 capable of accessing the Internet.

Figure 2B:
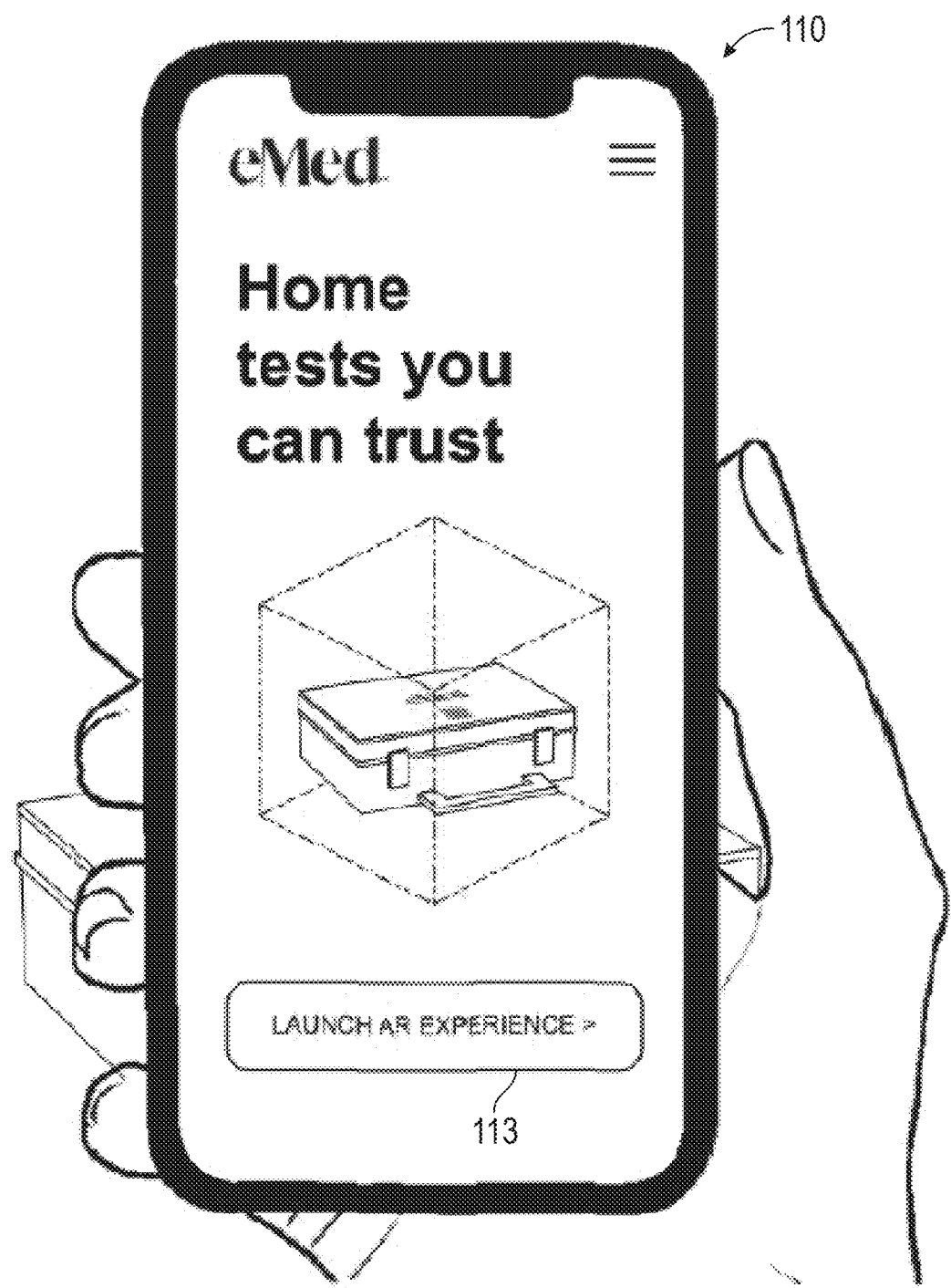
FIG. 2B illustrates an example screen display on the user device that can facilitate user initiation of an augmented reality experience associated with the medical diagnostic test kit container of FIG. 1 for devices configured for augmented reality displays, according to some embodiments described herein.

Clicking or tapping on the image and/or text hyperlink or button 112 can cause a Web browser to launch and navigate the user to a proprietary platform or provider website (e.g., a website controlled and monitored by the provider of the medical diagnostic test kit 100 or operator of a remote health testing and diagnostic platform). FIG. 2B illustrates an example screen display on the user device 110 that can facilitate user initiation of an augmented reality experience associated with the medical diagnostic test kit container 100. The provider or platform website may include a user-selectable option (e.g., a graphical user interface button 113) to launch an augmented reality experience that is implemented by a Web application or software application. The Web application or software application, or portions thereof may be stored on a provider or platform server, a cloud server, and/or local storage of the user device 110.

Augmented Reality Experience Associated with Medical Diagnostic Test Kit Container If the user device 110 is capable of implementing an augmented reality experience, the Web application or software application can be configured to present the user with augmented reality content including graphics and/or alpha-numeric text conveying various information to the user while providing an aesthetically-pleasing enhanced user interaction experience. The information can include, for example:

- Information about the contents within the medical diagnostic test kit container 100 (e.g., an overview of the collection of medical diagnostic test kits)
- Information about each individual medical diagnostic test in the collection (e.g., condition(s) tested, time to result, test accuracy, whether certified proctors are required, testing materials involved, etc.)
- Information about how each individual medical diagnostic test is taken or how it works (e.g., an overview of how the test is to be taken with infographics and/or text demonstrating various steps in the testing process and/or the testing materials involved).

Figure 3A:
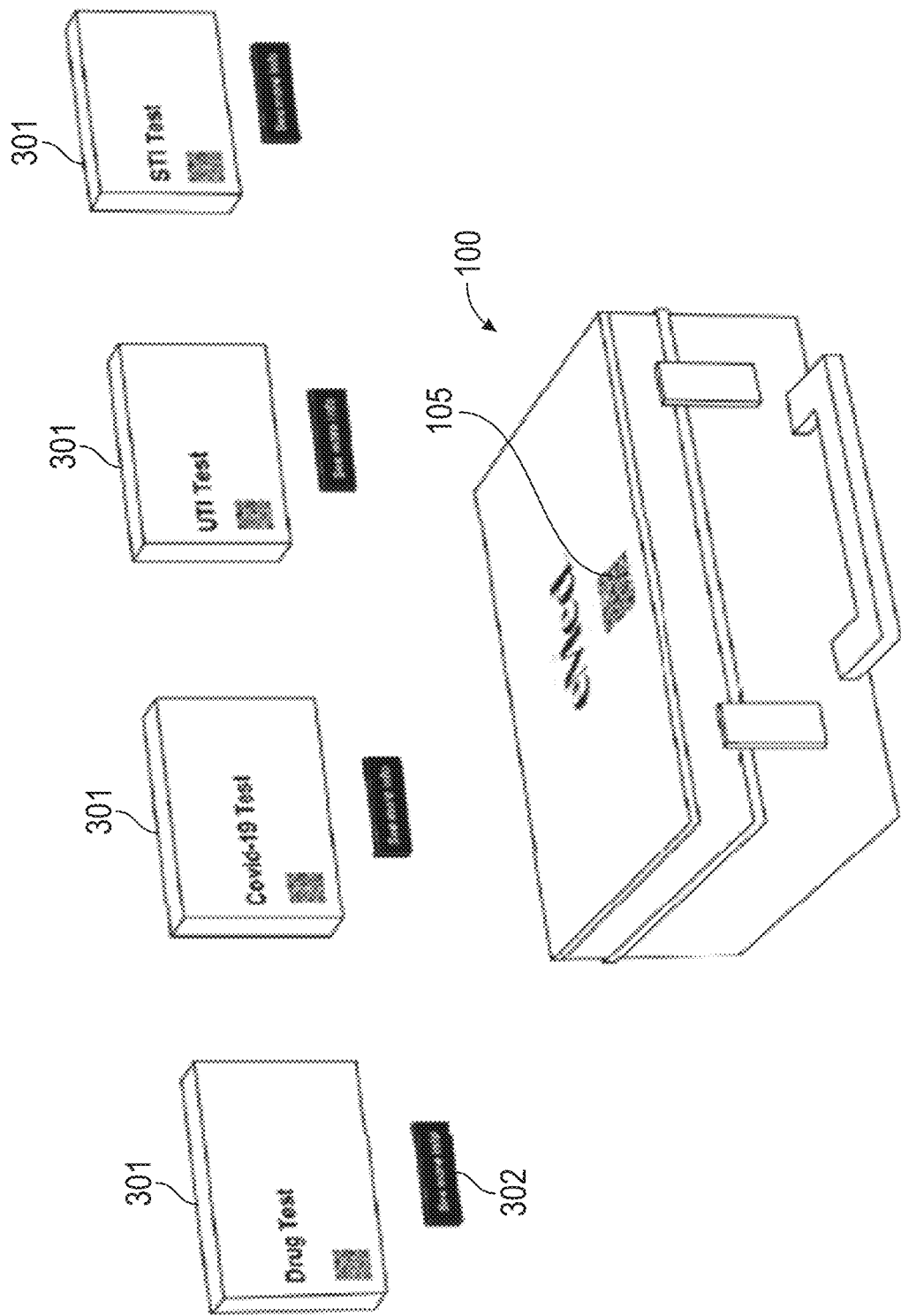
FIG. 3A illustrates an example augmented reality display and graphical user interface according to some embodiments described herein that shows virtual images of the medical diagnostic test kits located within the medical diagnostic test kit container of FIG. 1.
Figure 3B:
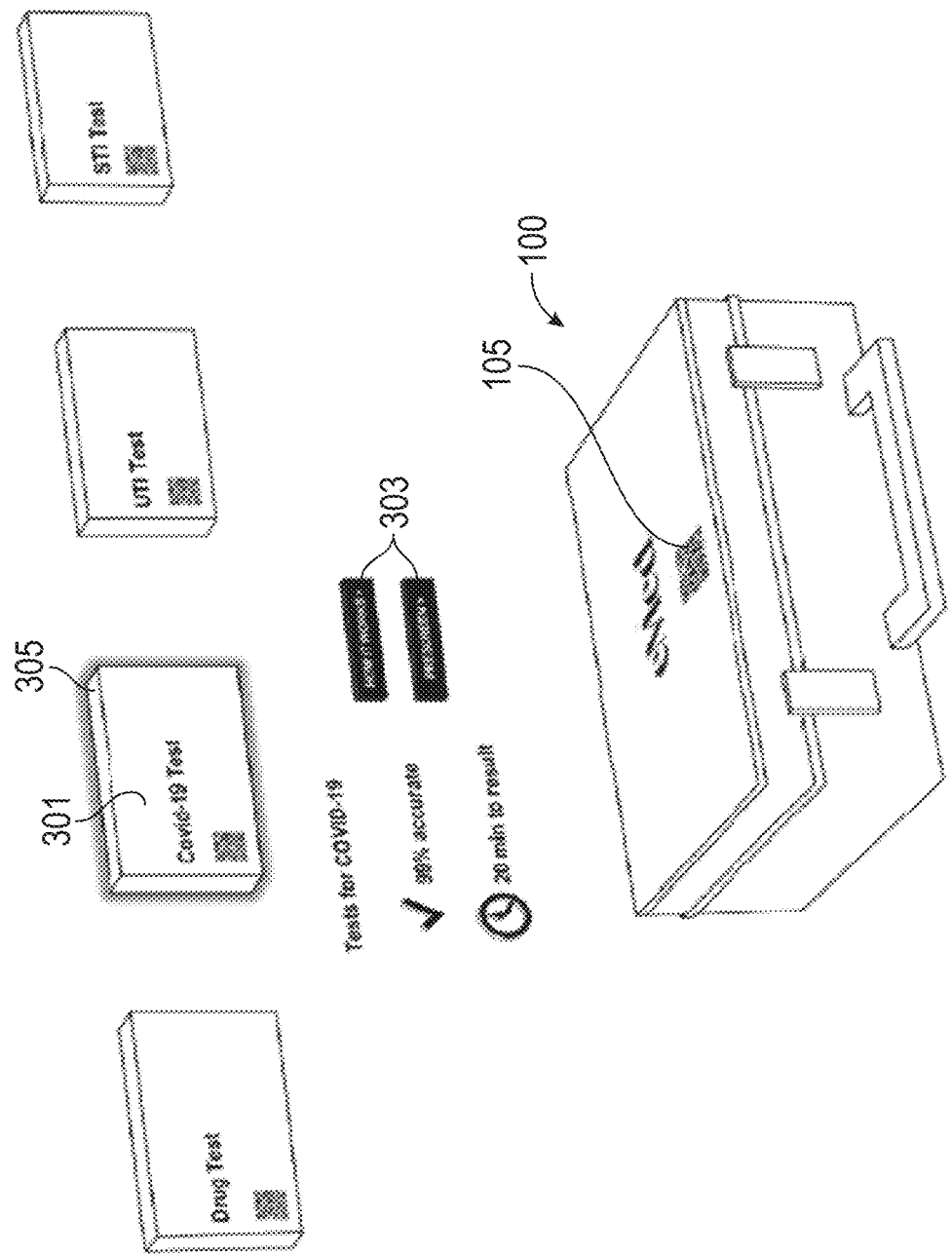
FIG. 3B illustrates an example of a further augmented reality display and graphical user interface following user selection of a particular medical diagnostic test kit in the augmented reality display experience according to some embodiments described herein.

FIGS. 3A-3D illustrate various examples of augmented reality content related to the medical diagnostic test kit container 100 that can be generated and displayed using the camera(s) and display screen 111 of the user device 110. Each of FIGS. 3A-3D may represent a scene as captured using the cameras of user device 110 and overlaid with augmented reality content. For example, the medical diagnostic test kit container 100 as shown in FIGS. 3A-3B may correspond to an image of a real world object. The machine-readable code 105 may serve as a fiducial or anchor point from which a coordinate frame, or registration calibration, for the augmented reality display or presentation can be established. In some implementations, graphics other than the machine-readable code 105 (e.g., a logo, a photo, etc.) on the medical diagnostic test kit container 100 may alternatively or additionally be leveraged to establish the coordinate frame or registration reference point for the augmented reality display or content presentation.

FIG. 3A illustrates an example of augmented reality content that displays the types of medical diagnostic test kits located within a particular medical diagnostic test kit container 100. The augmented reality content includes virtual images 301 of the various medical diagnostic test kits positioned to appear hovering over, or above, the medical diagnostic test container 100 and spaced apart from each other. For example, an augmented reality animation may play that "explodes" the virtual images 301 out of the medical diagnostic test kit container 100 as 3D icons floating in world space above the medical diagnostic test kit container 100. The virtual images 301 include text stating the name of the test, a machine-readable code (e.g., QR code), and one or more user-selectable buttons, images, and/or text icons 302 that, if selected by a user, provide further information about the particular selected medical diagnostic test kit and/or medical diagnostic test. Text on the buttons or icons 302 may include information to indicate that selection by the user will provide more details. The virtual images or icons 301 may also be selectable by the user to provide the user selection input data for further details. Although the buttons or icons 302 are shown in a position below the virtual image of the diagnostic test kit, other positions are contemplated as well. In addition, the virtual images 301 of the medical diagnostic test kits may be displayed in other arrangements or at other locations or positions.

FIG. 3B illustrates an example of a further augmented reality display and graphical user interface following user selection of a particular medical diagnostic test kit in the augmented reality display associated with FIG. 3A. As shown, the augmented reality content includes a shadow or highlighting feature 305 surrounding the virtual image 301 of the selected diagnostic test kit (in this illustration, the COVID-19 test kit). In addition, or as an alternative, the virtual image 301 of the selected medical diagnostic test kit may be enlarged or appear closer to the user than the virtual images of the unselected medical diagnostic test kits.

Further augmented reality content related to the selected medical diagnostic test kit may be displayed below the virtual image 301 of the selected medical diagnostic test kit. For example, the further augmented reality content may include further textual information about the selected medical diagnostic test kit, such as condition(s) tested, test accuracy, and time to result. The further augmented reality content may include a face sheet or card that animates out of the virtual image 301 and is displayed surrounding the virtual image 301 in world space (e.g., above, below, to the right or left). The further augmented reality content may also include additional user-selectable buttons, icons and/or text 303 that, when selected by a user in the augmented reality experience, provide the user with further information about how the selected medical diagnostic test works and/or to initiate a pre-screening survey or test related to the selected medical diagnostic test. Again, the locations and content of the further augmented reality content may vary as desired and/or required.

Figure 3C:
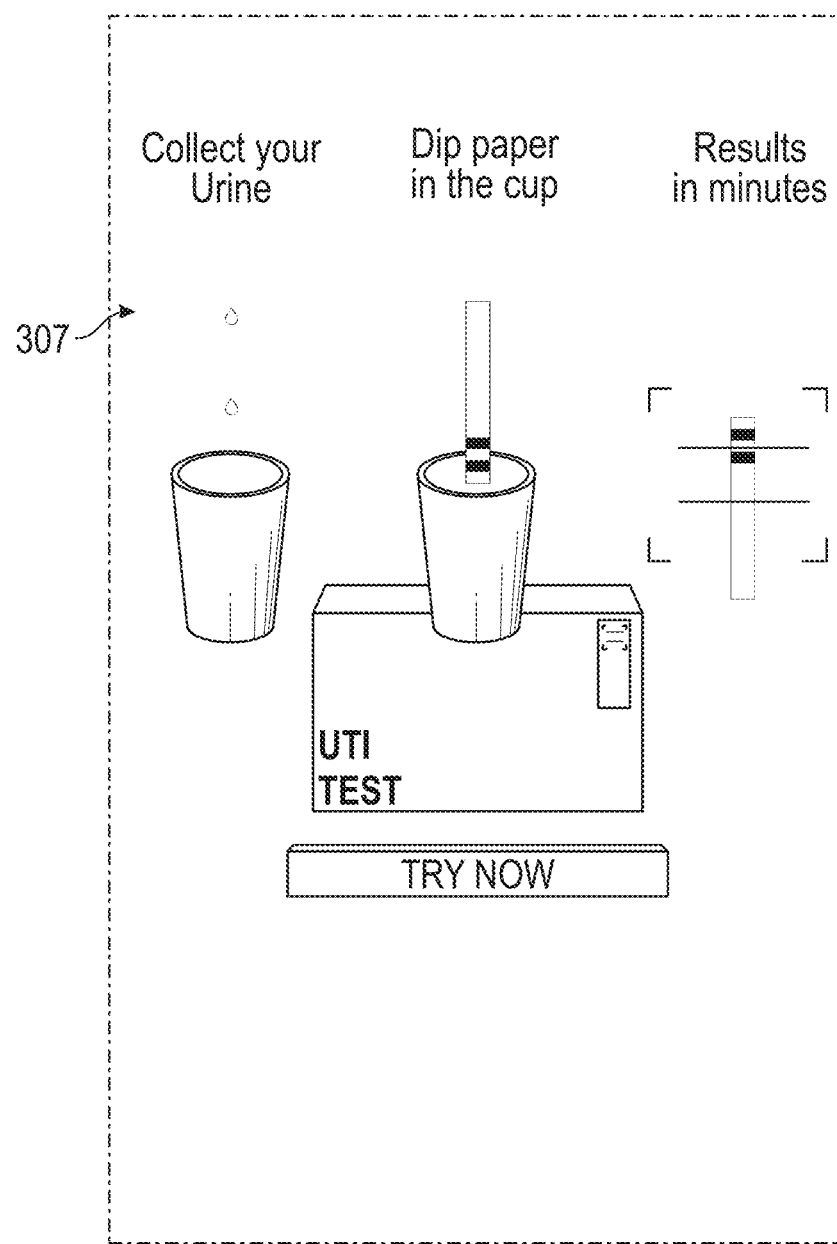
FIGS. 3C and 3D illustrate examples of augmented reality displays and graphical user interfaces showing an overview of steps of a urinary tract infection diagnostic test and a drug test, respectively, contained within the medical diagnostic test kit container, according to some embodiments described herein.
Figure 3D:
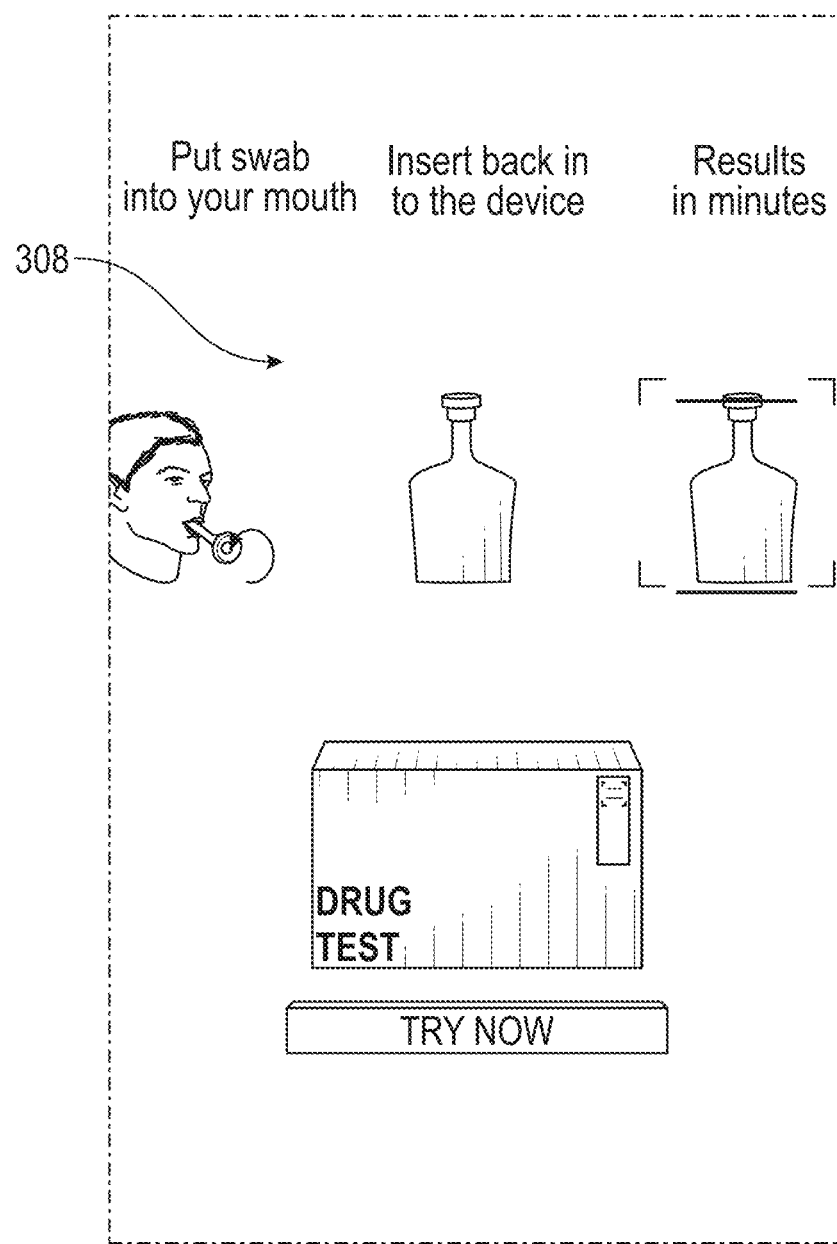

FIGS. 3C and 3D illustrate examples of augmented reality content that includes information about how a particular medical diagnostic test is taken or how it works. This further augmented reality content may be generated upon receipt of user input data indicating a request for further details or information. FIG. 3C illustrates example augmented reality infographics 307 showing an overview of the steps involved in a urinary tract infection (UTI) test and FIG. 3D illustrates example augmented reality infographics 308 showing an overview of the steps involved in a drug test. The overview of steps may be presented in an augmented reality video, animation, or still images. The infographics 307, 308 may be displayed at various positions or locations with respect to the medical diagnostic test kit container 100.

Figure 3E:
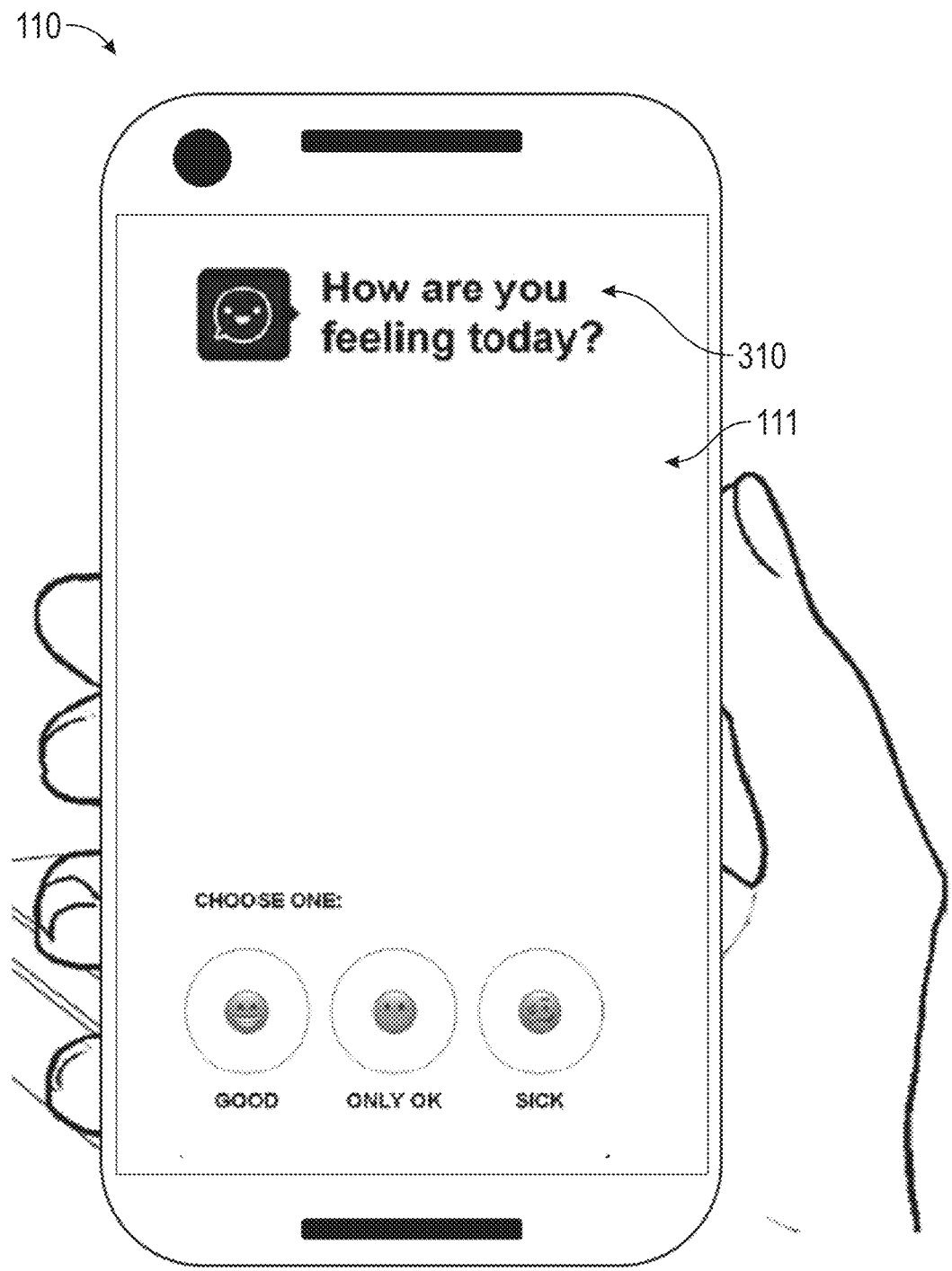
FIG. 3E illustrates an example of a 2-D display and graphical user interface that may be generated to facilitate a prescreening process to be completed via user interaction on a user device (e.g., mobile phone or tablet) prior to initiating a particular at-home medical diagnostic test according to some embodiments described herein.

FIG. 3E illustrates an example of a 2-D display and graphical user interface 310 that may be generated and presented on the display screen 111 of the user device 110 (e.g., personal computer, a cellular phone, a pair of smart glasses, a smartwatch, a smartphone, a laptop, a tablet computer, an e-reader device, an audio player, or another device capable of connecting to and communicating over a network, whether wired or wireless) if the user selects user-selectable content in the augmented reality experience to initiate a prescreening survey or chatbot. The illustrated display may be the first question of several questions that are completed via user interaction involving graphical user interfaces on a user device (e.g., mobile phone or tablet) prior to initiating a particular at-home medical diagnostic test.

The prescreening survey or test may help determine whether the user should take the selected medical diagnostic test. Although the user may obtain the medical diagnostic test kit container 100 without a prescription (and thus may take any of the medical diagnostic tests in the diagnostic test kit container 100 whenever he or she feels like it), it may not be a worthwhile use of a particular medical diagnostic test if the user is not exhibiting the corresponding symptoms. In some implementations, therefore, as a user experience enhancement, the prescreening surveys can be used to help users avoid wasting medical diagnostic test kits in situations where usage is deemed unnecessary.

In some implementations, the health testing and diagnostic platform (e.g., platform 4202 shown in FIG. 42) may receive user input of survey answers from the user device 110 and attempt to pre-qualify the user based on available guidelines, such as government stipulated testing requirements. In some implementations, information can be gathered about the user that may facilitate various functionality of the health testing and diagnostic platform. For example, the user's identity can be verified. Verification of the user's identity can occur in various ways as described further below. In some implementations, verification of the user's identity comprises checking the user's ID (e.g., driver's license or passport). In some implementations, the user's identity is verified using biometrics. Additionally, information about the user may be gathered at this stage which may facilitate matching the user to a proctor within the system in a manner that improves the efficiency of the system.

In addition to checking symptoms, the user patient may also be prompted by the platform to complete a medical questionnaire to provide additional information regarding the patient's condition, health history, and/or other relevant information. In some implementations, the information gathered can include information regarding the user patient's travel history and/or future travel plans. For example, the process can include presenting the user with questions regarding their travel plans (e.g., "Are you planning to travel into or out of the United States within the next 72 hours?").

Figure 4A:
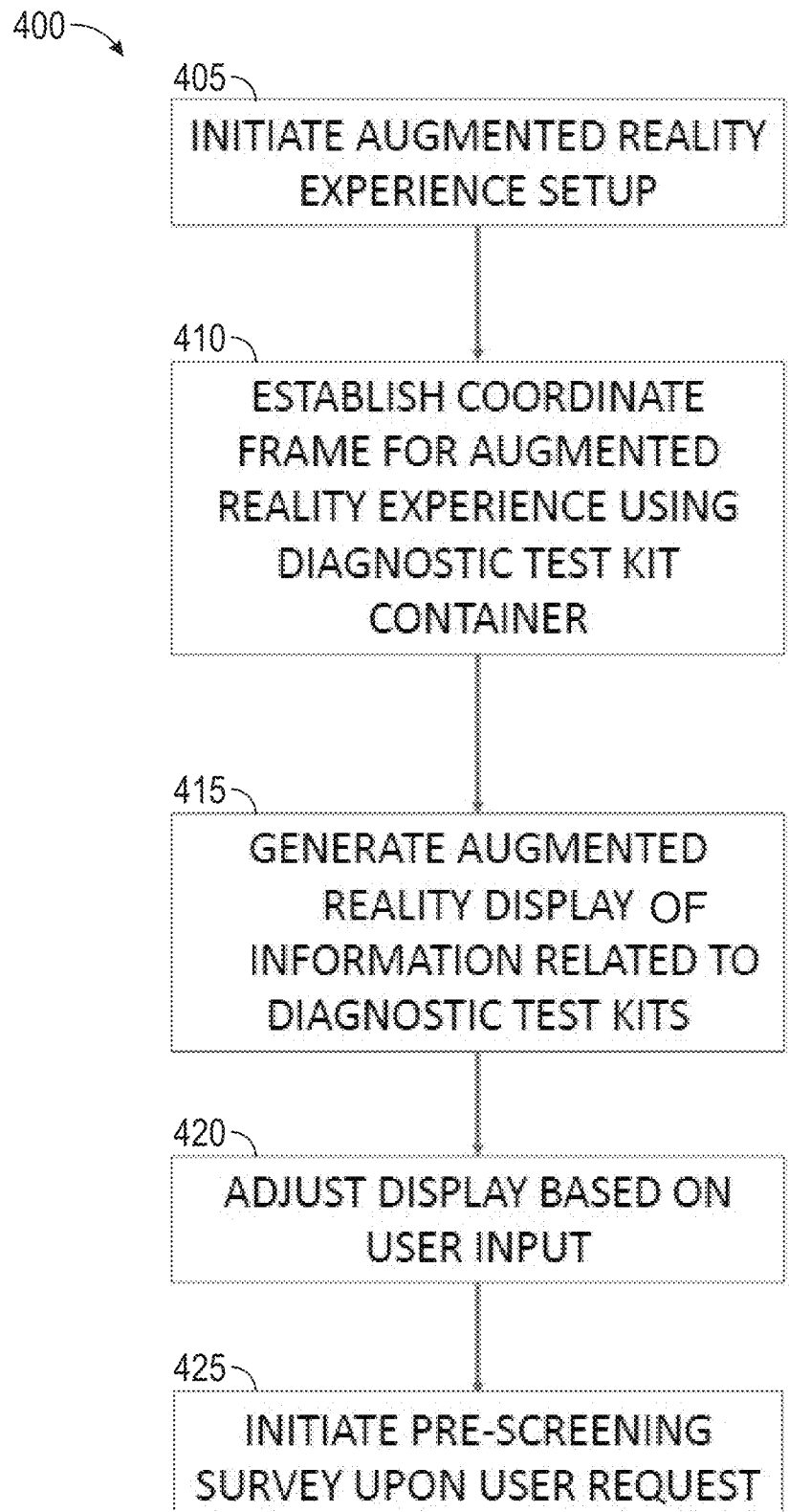
FIGS. 4A and 4B illustrate an example flowchart of a method of providing an augmented reality experience for a user interacting with the medical diagnostic test kit container of FIG. 1 according to some embodiments described herein.
Figure 4B:
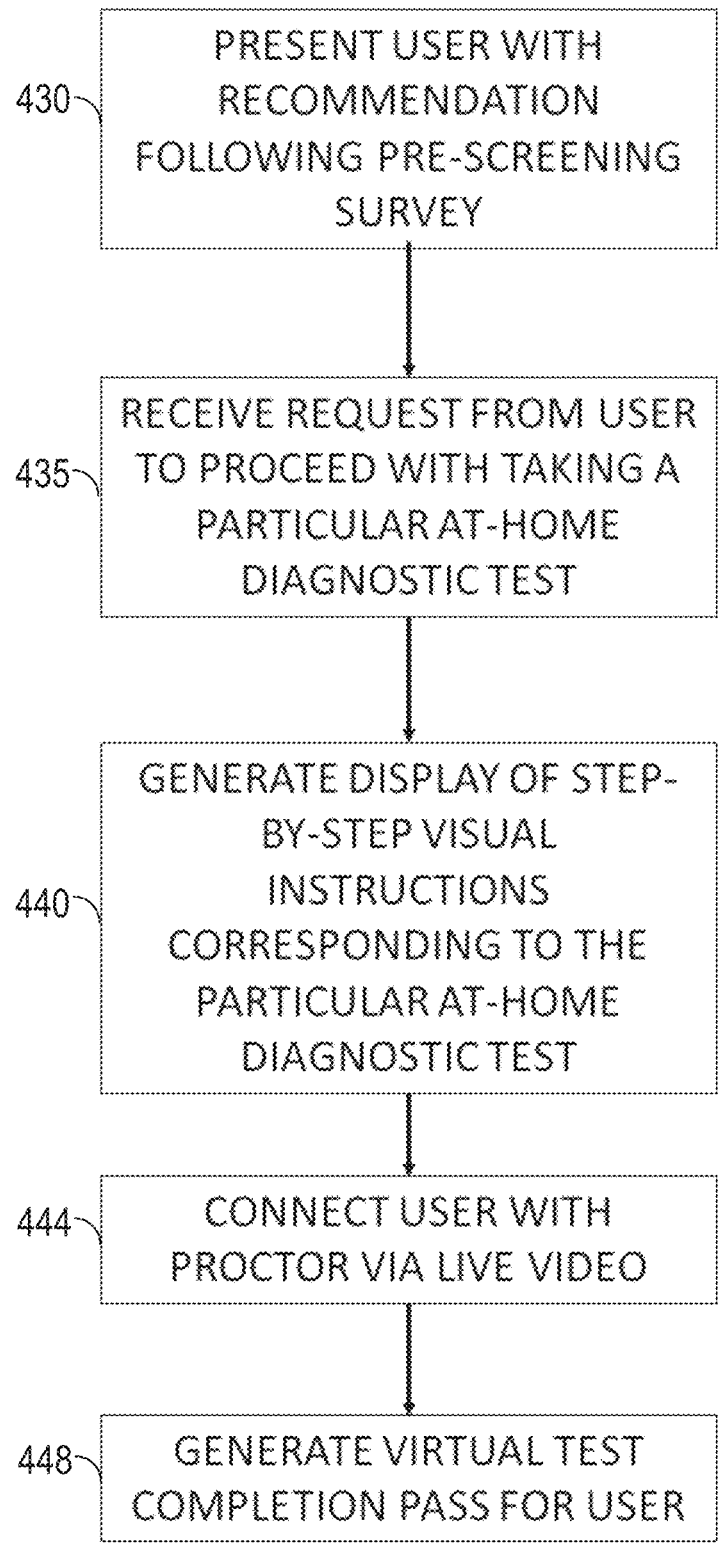

FIGS. 4A and 4B illustrate an example flowchart of a method 400 of providing an augmented reality experience for a user interacting with the medical diagnostic test kit container 100. At Block 405, a remote health testing and diagnostic platform (e.g., software application or Web application upon execution of program instructions stored on a computer-readable storage medium, such as platform 4202 shown in FIG. 42) initiates an augmented reality experience setup associated with the medical diagnostic test kit container 100. The initiation of the augmented reality experience setup at Block 405 may be triggered by receipt of user input data (e.g., the user selection of a selectable graphical user interface button or other content on a platform webpage or Web application) that indicates a desire to launch an AR experience associated with the medical diagnostic test kit container 100.

For example, to get to this point, a user may scan the machine-readable code 105 (e.g., QR code) on the exterior of the medical diagnostic test kit container 100 using a camera of the user device 110 (e.g., smartphone or tablet), as shown in FIG. 2A. Then, in response to the user scanning the machine-readable code 105, the user device 110 provides the user with an opportunity to proceed to a URL (webpage) that is associated with the machine-readable code 105. Receiving user input data indicating that the user would like to proceed to the URL (webpage) can trigger the user device 110 to proceed to the URL (webpage), which in turn provides the user with the opportunity to launch the AR experience, as shown in FIG. 2B.

At Block 410, the remote health testing and diagnostic platform (e.g., software application or Web application) establishes a coordinate frame for the augmented reality experience associated with the medical diagnostic test kit container 100. The platform may use the machine-readable code 105 and/or other graphics or portions of the medical diagnostic test kit container 100 to establish the coordinate frame, or registration.

At Block 415, augmented reality content associated with the medical diagnostic test kits contained within the medical diagnostic test kit container 100 is displayed or overlaid on real-time, real-world images obtained by the camera(s) of the user device 110, as shown for example in FIG. 3A. At Block 420, the augmented reality content and display is adjusted based on receipt of user input data. For example, the augmented reality content is adjusted to indicate or highlight a selected diagnostic test kit and/or to display additional information related to a particular diagnostic test kit, as shown in FIGS. 3B-3D. At Block 425, a prescreening survey or questionnaire is optionally initiated upon user request (e.g., upon the user clicking on, tapping, or touching via touchscreen interface a "Prescreening" virtual button 302 in the augmented reality display of FIG. 3B).

The method 400 may continue following the prescreening survey. Turning to FIG. 4B, the method 400 may proceed with facilitating completion of one of the at-home medical diagnostic tests using a medical diagnostic test kit within the medical diagnostic test kit container 100. At Block 430, in some implementations, upon completing the prescreening survey, a recommendation may be generated by the health testing and diagnostic platform and presented to the user concerning whether the user should take the particular medical diagnostic test. The user may also be presented with an opportunity to indicate that he or she would like to proceed with taking the particular medical diagnostic test, regardless of the recommendation. At Block 435, a request is received by the health testing and diagnostic platform to proceed with taking a particular at-home medical diagnostic test (e.g., a virtual graphical user interface button or other user-selectable image, icon, and/or text link presented on a display screen 111 of the user device 110).

At Block 440, augmented reality content may be generated and displayed on the user device 110 that includes step-by-step visual instructions and/or infographics corresponding to the particular at-home medical diagnostic test. Example augmented reality content that may be overlaid on real-time, real-world images of the user and/or diagnostic test kit obtained from front-facing and/or rear-facing cameras of the user device 110 is shown, for example, in FIGS. 8A-8J, 9A-9F, and 10A-10H. In some implementations, the step-by-step visual instructions and/or infographics may be presented in a 2D format and not as AR content.

At Block 444, the remote health testing and diagnostic platform may facilitate connection of the user with a proctor via live video (e.g., over the Internet or cellular telecommunications network) using the user device if the particular medical diagnostic test requires a proctor to observe at least a portion of the test administration for certification purposes. In some embodiments, the user may be connected with a proctor or other personnel while performing the testing procedure at block 440 at the user's request (e.g., to receive assistance with performing a specific step, etc.). In some embodiments, at block 444 a proctor or other personnel may observe at least a portion of the test administration for certification purposes without engaging in a live video connection with the user. At Block 448, the remote health testing and diagnostic platform may optionally generate a virtual, or digital, test completion pass for the user, as will be described further below. In some implementations, block 448 may additionally or alternatively include one or more steps for procuring prescription medicine or otherwise receiving treatment, such as one or more of the steps described below with reference to FIGS. 15-17B.

Medical Diagnostic Test Kit Container Inventory Tracking

Figure 4C:
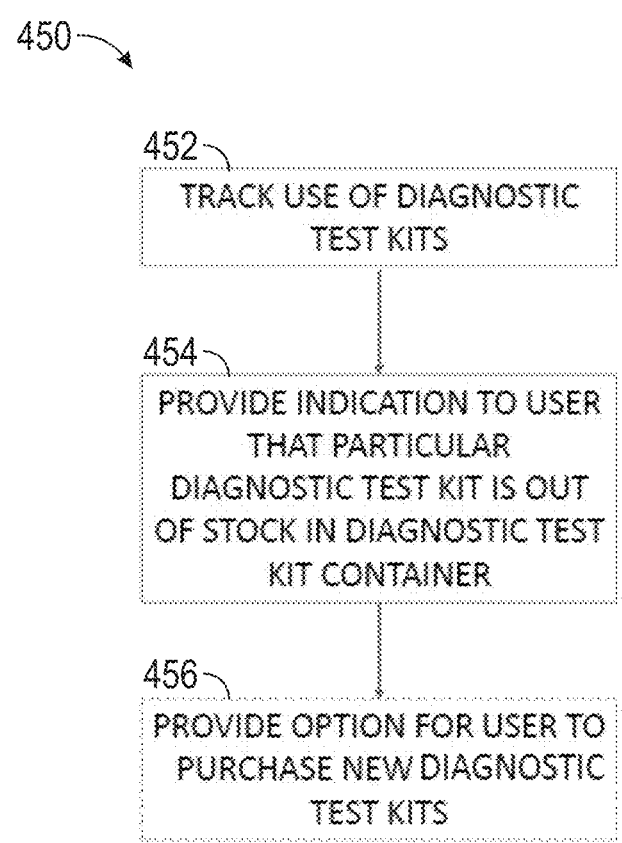
FIG. 4C illustrates an example flowchart of a method of tracking inventory of medical diagnostic test kits within the medical diagnostic test kit container and providing notifications to a user when inventory is low according to some embodiments described herein.

FIG. 4C illustrates an example flowchart of a method 450 of tracking inventory of medical diagnostic test kits within the medical diagnostic test kit container 100 and providing notifications to a user when inventory is low. At Block 452, the remote health testing and diagnostic platform (e.g., platform 4202 shown in FIG. 42) tracks use of medical diagnostic test kits in the medical diagnostic test kit container 100. The remote health testing and diagnostic platform may be pre-programmed with the initial start count or tally of each type of medical diagnostic test kit in the medical diagnostic test kit container 100 or the user may indicate or provide the initial start count or tally. The remote health testing platform may track inventory, for example, by decreasing a count or tally upon user indication of initiation of a particular medical diagnostic test. Of course, the count or tally may be decreased at other stages of the test taking process as well. For example, the user may be requested to scan a machine-readable code located on packaging of a particular medical diagnostic test kit once the diagnostic test is completed using that kit and the scanning of the machine-readable code may cause the remote health testing platform tracking program to decrease the count or tally for that type or category of medical diagnostic test kit. In some embodiments, this information may be stored and managed in association with the user's account.

At Block 454, the remote health testing and diagnostic platform may provide an indication to a user (via an alert notification, text message, email message or other notification means) that a particular category or type of medical diagnostic test kit(s) is running low or has been completely depleted and is in need of a resupply. In some implementations, the remote health testing platform may provide the indication by presenting a modified representation of the virtual medical diagnostic test kit image in the augmented reality display. For example, an out-of-stock medical diagnostic test kit may be presented in gray or other different color, as an outline, with highlighting, and/or with one or more graphics (e.g., strikethrough symbol, letter X, or circle with a diagonal line through it) indicating that the medical diagnostic test kit container 100 no longer includes any of the particular medical diagnostic test kit. The method 450 may optionally include (at Block 456) providing an option for a user to purchase additional medical diagnostic test kits upon receipt of the indication (e.g., alert or other notification). The option may be provided via a hyperlink or user-selectable graphical icon, button, or image to direct the user to a URL or Webpage or e-commerce portal to facilitate purchasing of additional medical diagnostic test kits. In some implementations, the option may be presented using an inline HTML iframe element.

At-Home Medical Diagnostic Test Kits

Figure 5:
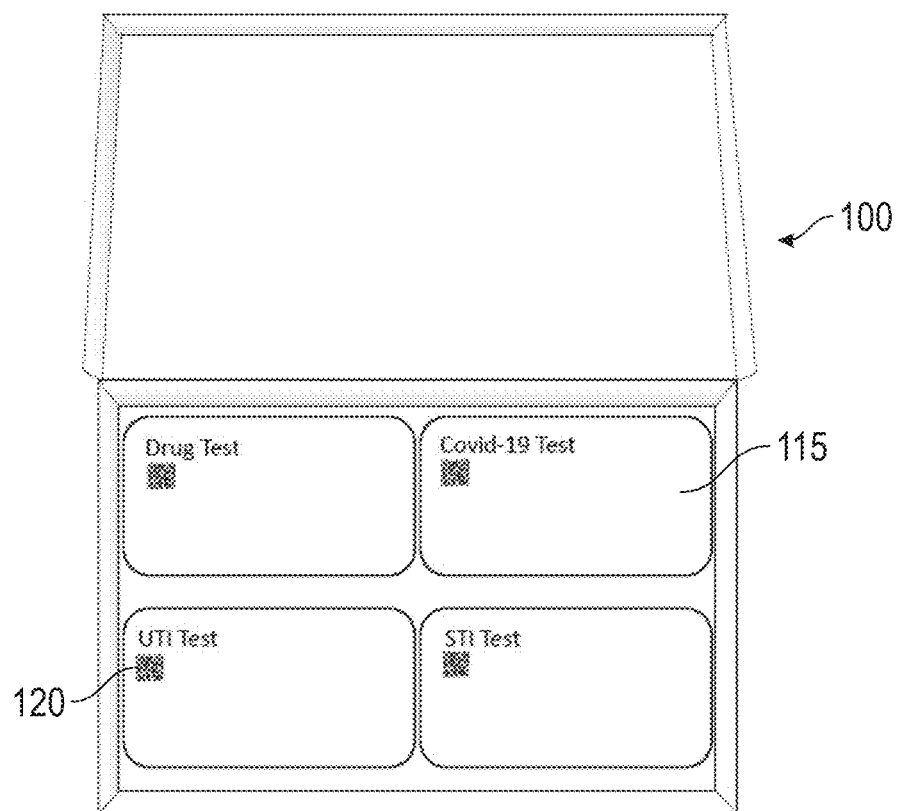
FIG. 5 illustrates examples of items (e.g., at-home medical diagnostic test kits) that may be included in the medical diagnostic test kit container or package of FIG. 1 according to some embodiments described herein.

FIG. 5 illustrates examples of items (e.g., at-home medical diagnostic test kits 115) that may be included in the medical diagnostic test kit container or package 100. As shown, the particular medical diagnostic test kit container 100 includes one or more drug test kits, one or more COVID-19 test kits, one or more UTI test kits, and one or more sexually transmitted infection (STI) test kits. Different diagnostic test kit containers 100 may include different types and amounts of test kits 115 geared toward particular households, individuals, or other groups or facilities, depending on needs, lifestyles, or circumstances. The number of total test kits 115 may vary (e.g., 2 test kits, 3 test kits, 4 test kits, 5 test kits, 6 test kits, 7 test kits, 8 test kits, 9 test kits, 10 test kits, more than 10 test kits).

As shown in FIG. 5, in some implementations, each of the medical diagnostic test kits 115 inside the medical diagnostic test kit container 100 may bear its own machine-readable code 120 (e.g., QR code, AR code, PDF417 code, bar code, datamatrix code, Aztec code). The machine-readable codes 120 on the individual medical diagnostic test kits 115 may be positioned on an external surface of packaging of the diagnostic test kit 115 but may alternatively be positioned in locations other than the location illustrated in FIG. 5. In some implementations, the machine-readable code 120 that is scanned may be printed on one or more of the diagnostic test kit materials (rather than the box or other packaging). In some implementations, other types of machine-readable codes (e.g., bar codes, etc.) can be used in addition to or in place of the illustrated QR codes.

The external surface of the packaging of the medical diagnostic test kit 115 may also include graphics, logos, photos, or textual content in addition to the machine-readable codes 120. Multiple machine-readable codes 120 may be positioned at different locations on each medical diagnostic test kit packaging in some implementations. In some implementations, one or more computer vision techniques may be leveraged to identify test kit materials and packaging instead of or in addition to the QR code scanning techniques.

In accordance with several implementations, scanning of a machine-readable code 120 on a particular medical diagnostic test kit 115 may cause the user device 110 to automatically initiate an augmented reality experience associated with the particular medical diagnostic test kit 115. Again, the machine-readable code 120, alone or in combination with other graphics or portions of the medical diagnostic test kit 115 may serve as a fiducial reference or registration point for establishing a coordinate frame for the augmented reality content presentation in some implementations. In some implementations, simultaneous localization and mapping (SLAM) or other autonomous control methods or techniques may be used to calculate a spatial relationship between the user device 110 and multiple keypoints.

Figure 6:
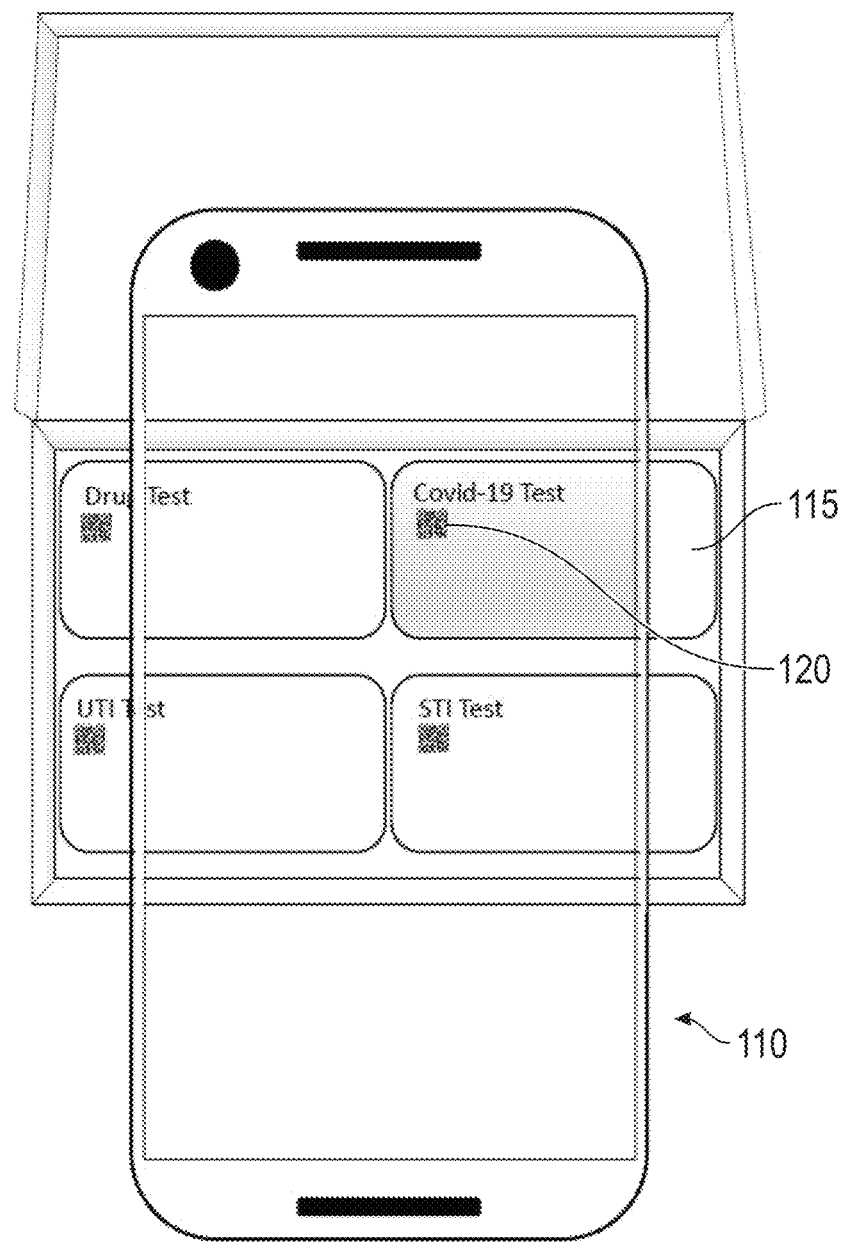
FIG. 6 illustrates an example of a user scanning a machine-readable code located on a particular medical diagnostic test kit using a mobile phone having a built-in camera according to some embodiments described herein.

FIG. 6 illustrates an example of a user scanning a machine-readable code 120 located on a particular medical diagnostic test kit 115 (in this instance, a COVID-19 test kit) using a user device 110 (e.g., mobile phone) having one or more built-in cameras. The machine-readable codes 120 (e.g., QR codes, AR codes) may be scanned while a particular medical diagnostic test kit 115 remains within the medical diagnostic test kit container 100 or after removal of the particular medical diagnostic test kit 115.

Figure 7:
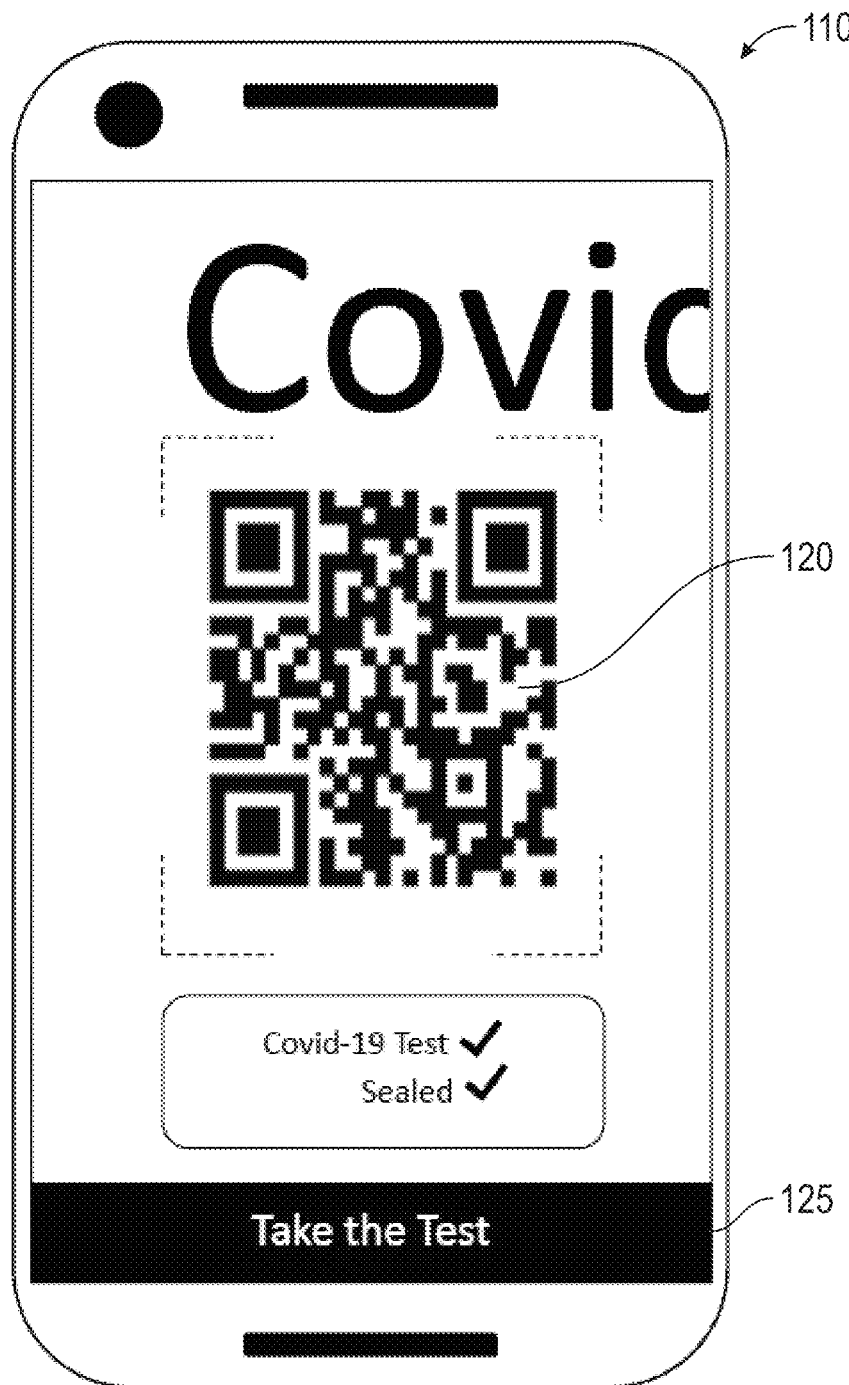
FIG. 7 illustrates an example of a graphical user interface screen that may be displayed on a portable user device upon scanning of a machine-readable code of a particular medical diagnostic test kit according to some embodiments described herein.

FIG. 7 illustrates an example of a graphical user interface screen that may be displayed on a user device 110 (e.g., mobile phone, smartphone, or tablet) upon scanning of the machine-readable code 120 of a particular medical diagnostic test kit 115. As shown, the graphical user interface may include a user-selectable button 125 or other graphic or textual link that provides the user with an option to initiate taking the test associated with the particular medical diagnostic test kit 115 for which the machine-readable code 120 has been scanned. Upon receipt of a user indication or user input data (e.g., pressing of the user-selectable button 125 on the graphical user interface), the augmented reality content may transition to the step-by-step guide to completion of the medical diagnostic test using the medical diagnostic test kit 115.

Augmented Reality (AR) Based Testing Guidance for At-Home Medical Diagnostic Test Kits In some implementations, the remote health testing and diagnostic platform (e.g., platform 4202 shown in FIG. 42) may provide augmented reality (AR) based testing guidance to users and/or proctors. Because users and proctors generally interact with the platform using devices that include displays, AR-based testing guidance can be overlaid onto the displays to facilitate testing and/or proctoring. For example, graphics can be overlaid onto a live video feed of the medical diagnostic test kit (as provided by one or more cameras of the user device 110) to help the user properly open, set up, utilize, and/or dispose of the test kit 115. As a more specific example, in some tests, the user may be required to deposit drops of a solution onto a certain portion of a test card (see, for example, FIG. 8D, described below). The user can be instructed to position the test kit 115 such that it is within the view of the camera and can be viewed on the user's screen. Augmented reality guidance (infographics, images and/or text) indicating where to deposit the drops can be overlaid onto the user's screen to indicate where the user should place the drops of solution. As another example, when the user needs to access a swab within the test kit 115, the location of the swab can be highlighted using AR on the user's screen.

AR-based guidance can be implemented in a variety of different ways. In the illustrated examples herein, a user accesses the remote health testing and diagnostic platform using a user device 110 (e.g., smartphone or tablet). In this example, the user device 110 includes both forward facing and rearward facing cameras. One or both of these cameras can be used during a testing procedure to capture images of, for example, the user and/or a test kit 115 used during the testing procedure. Further, the images captured by the forward and/or rearward facing cameras can be displayed to the user on a display 111 of the user device 110. Moreover, AR-based guidance can be added to the images displayed to the user to facilitate and improve the testing experience. Examples of AR-based guidance that can be displayed to the user are shown in FIGS. 8A-H, described below.

Figure 8A:
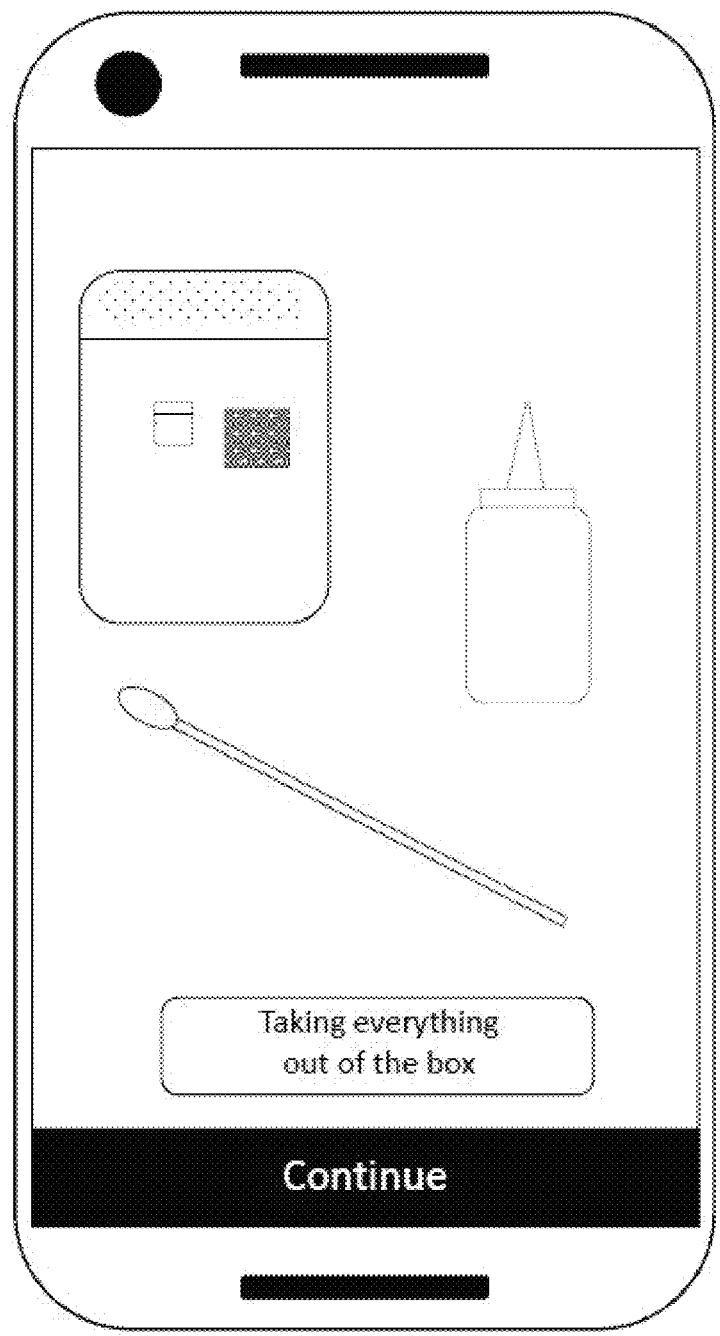
FIGS. 8A-8J illustrate a series of example screen displays that can be displayed to a user to guide the user through the steps of administering an at-home COVID-19 diagnostic test according to some embodiments described herein.
Figure 8B:
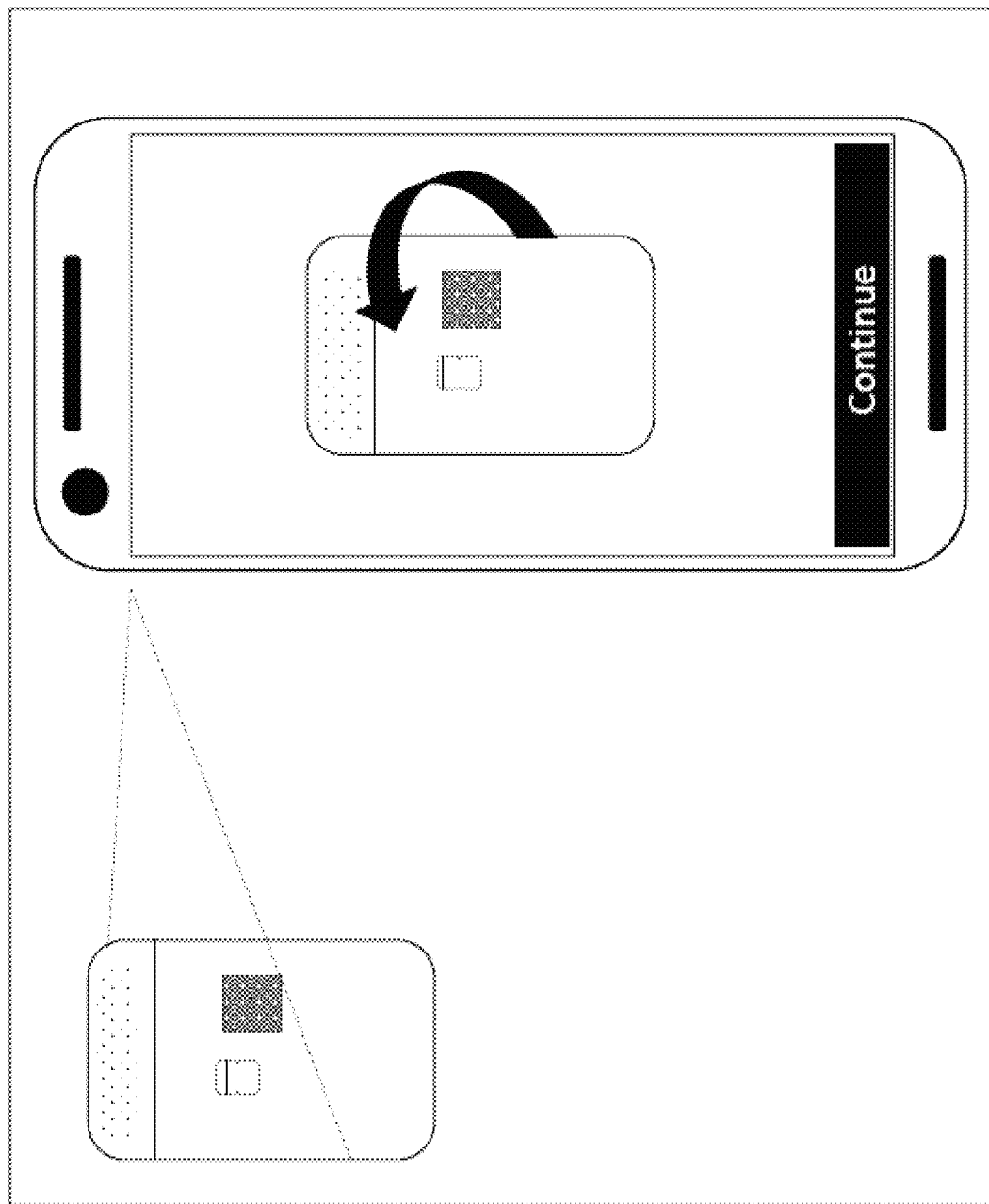
Figure 8C:
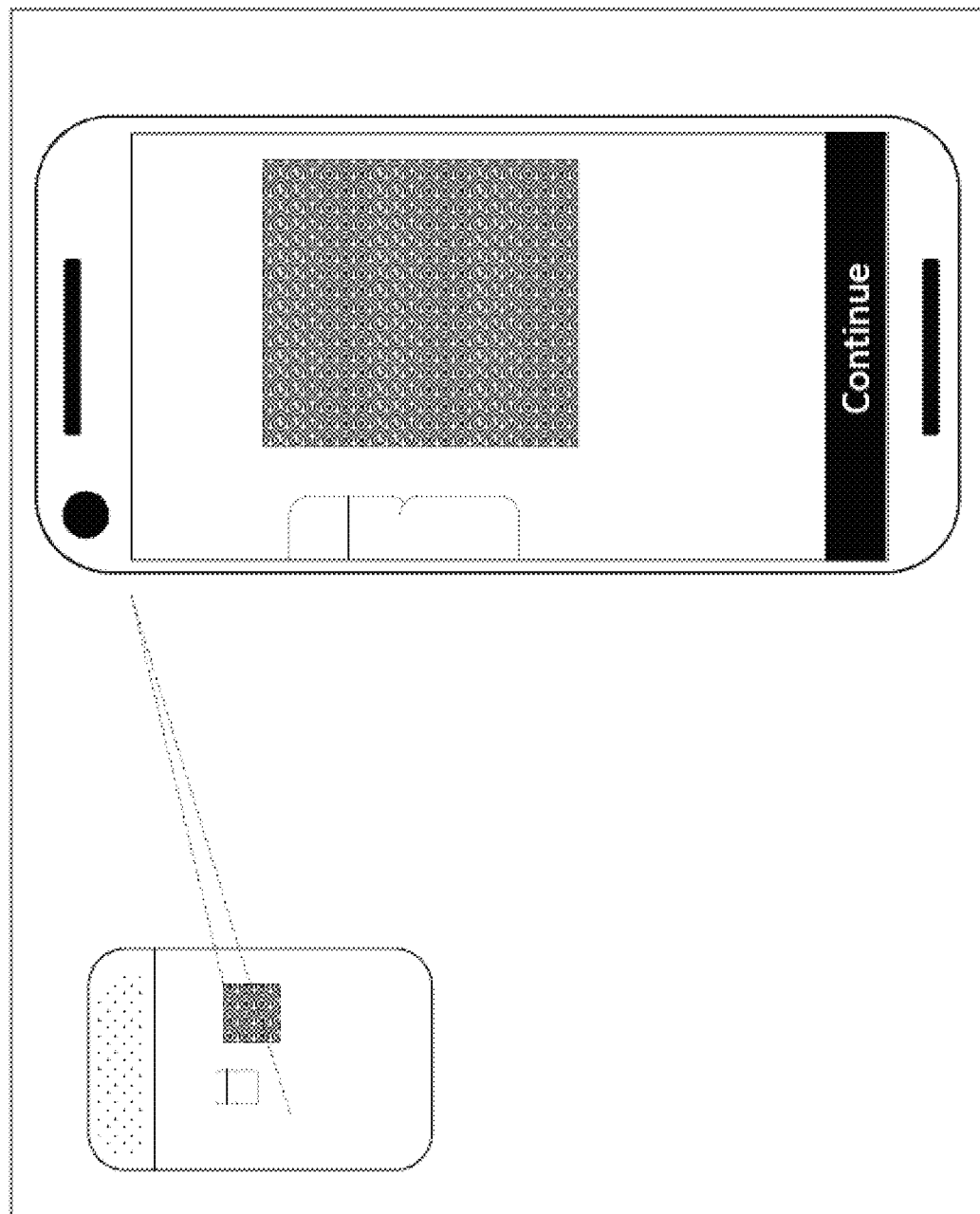

FIGS. 8A-8J illustrate a series of example screen displays that can be displayed to a user to guide the user through the steps of completing an at-home COVID-19 diagnostic test according to some embodiments described herein. The screen displays may include augmented reality display content that is overlaid on real-time, real-world camera images of components or portions of the medical diagnostic test kit 115 and/or the user. As shown, the screen displays may also include infographics, text instructions, and user-selectable content (e.g., buttons) to facilitate receipt of user indication of completion of each step of the testing process in order to continue on to the next step. FIG. 8A includes a display that instructs the user to take the contents out of the COVID-19 test kit. FIG. 8B includes a display that instructs the user to flip over the COVID-19 test kit. The augmented reality content may include a virtual arrow image overlaid on the real-world image of the test kit. FIG. 8C includes a display that is zoomed in on a certain portion of the test kit, potentially for verification that the test kit is sealed and has not been used or tampered with prior to administration of the test or to scan a machine-readable code on the test kit.

Figure 8D:
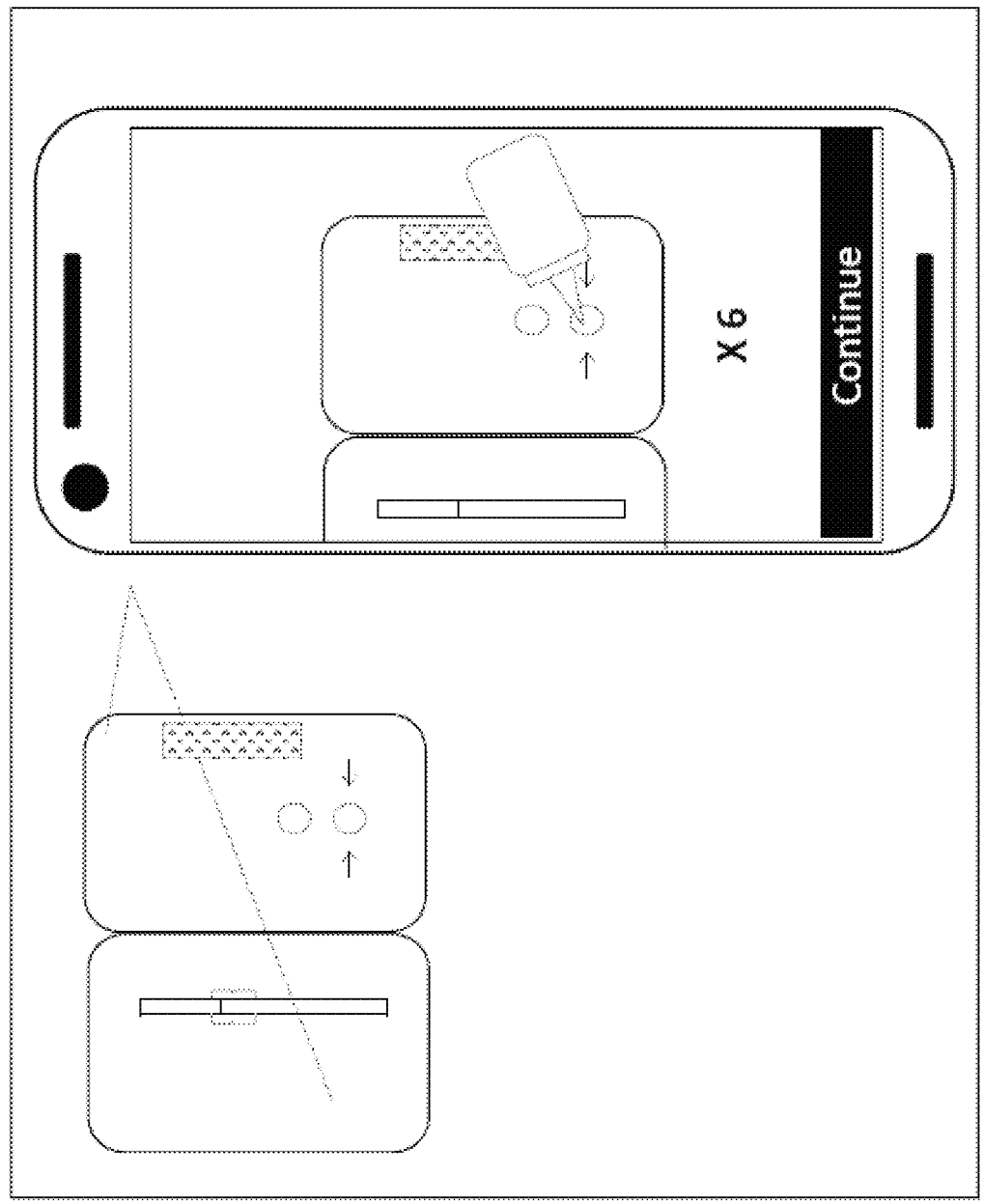
Figure 8E:
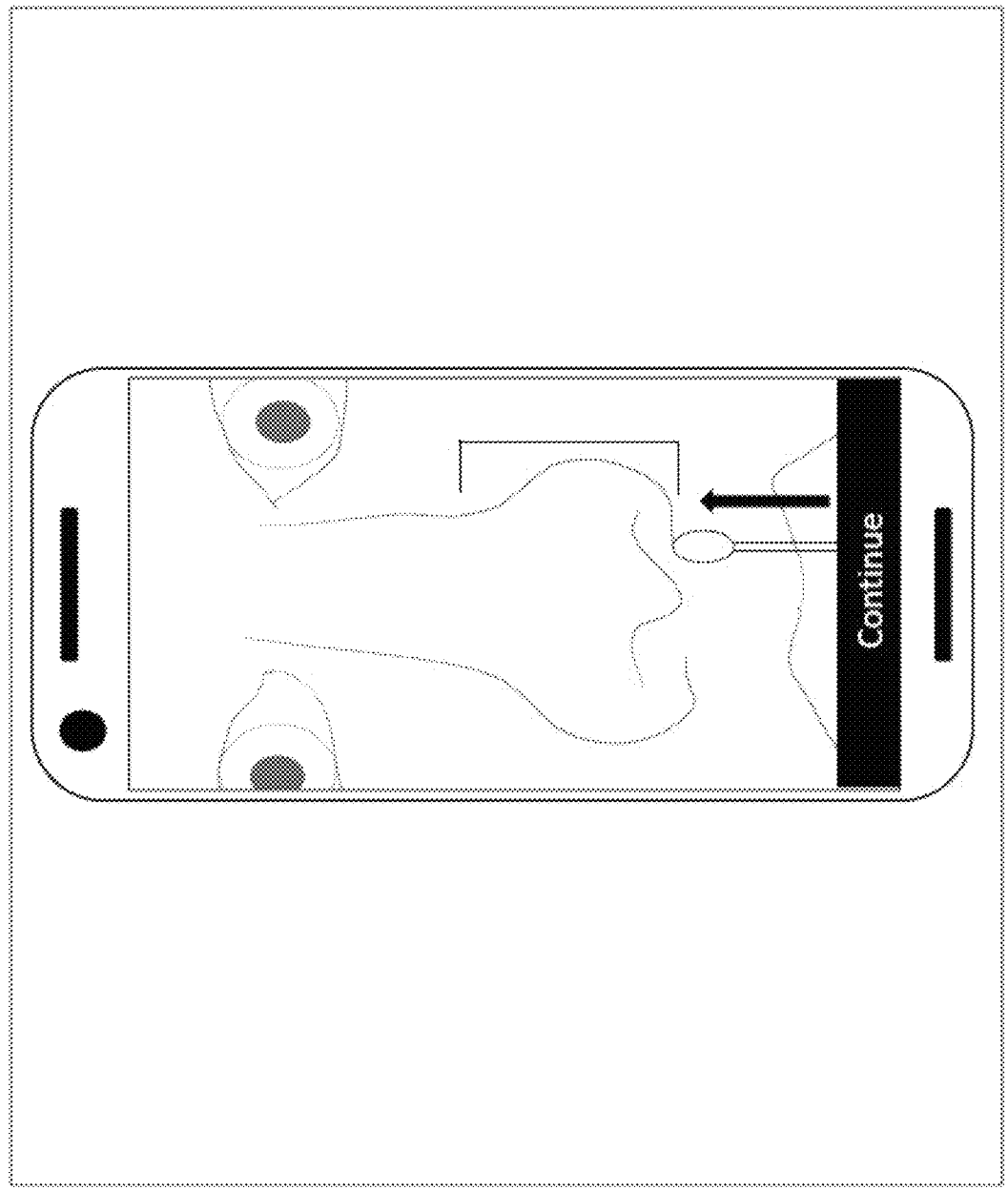
Figure 8F:
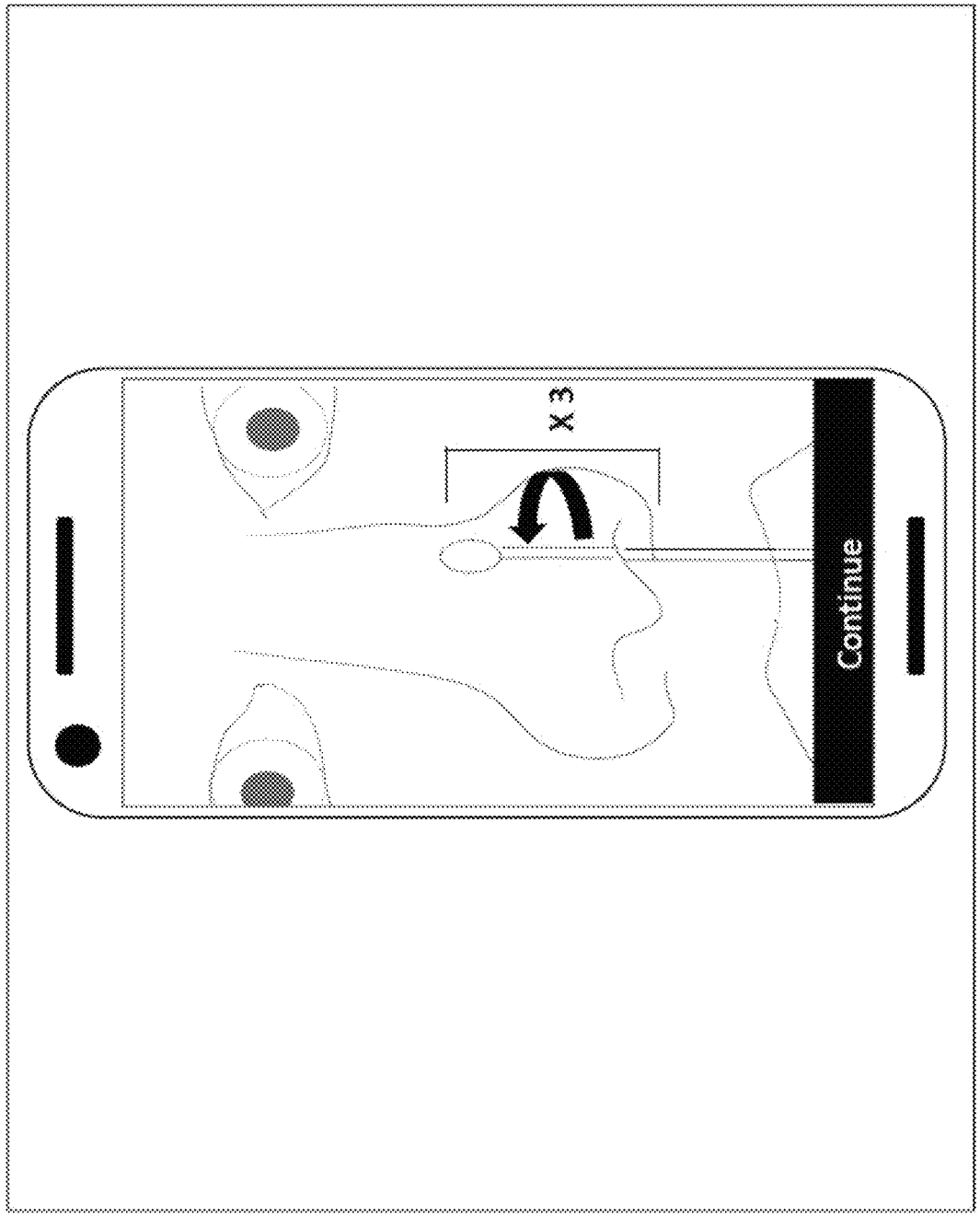

FIG. 8D includes a virtual image or animation of a bottle dropper (which may be one of the real-world items within the COVID-19 test kit) and a textual display of "×6" indicating to the user to insert 6 drops of the fluid from the bottle dropper into the indicated hole or window on the COVID-19 test kit. FIG. 8E includes a virtual image or animation of a cotton swab stick (which may be another real-world item within the COVID-19 test kit) being inserted within a nostril, thus guiding the user to perform this step of the COVID-19 diagnostic test. FIG. 8F includes a virtual image or animation that includes a curved arrow and that may show the cotton swab stick rotating, as well as a textual display of "×3", to indicate to the user to rotate the cotton swab three times within the nostril.

Figure 8G:
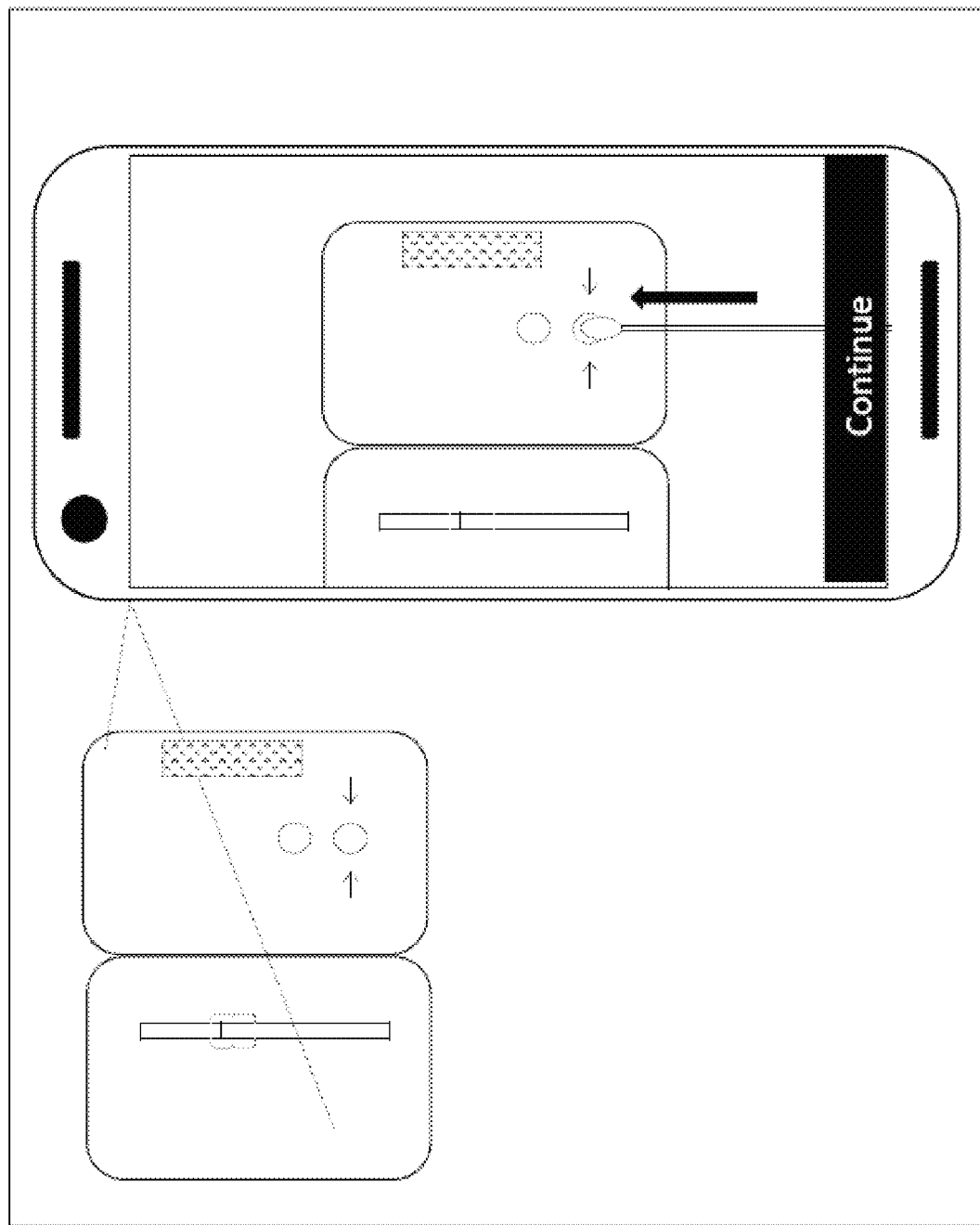
Figure 8H:
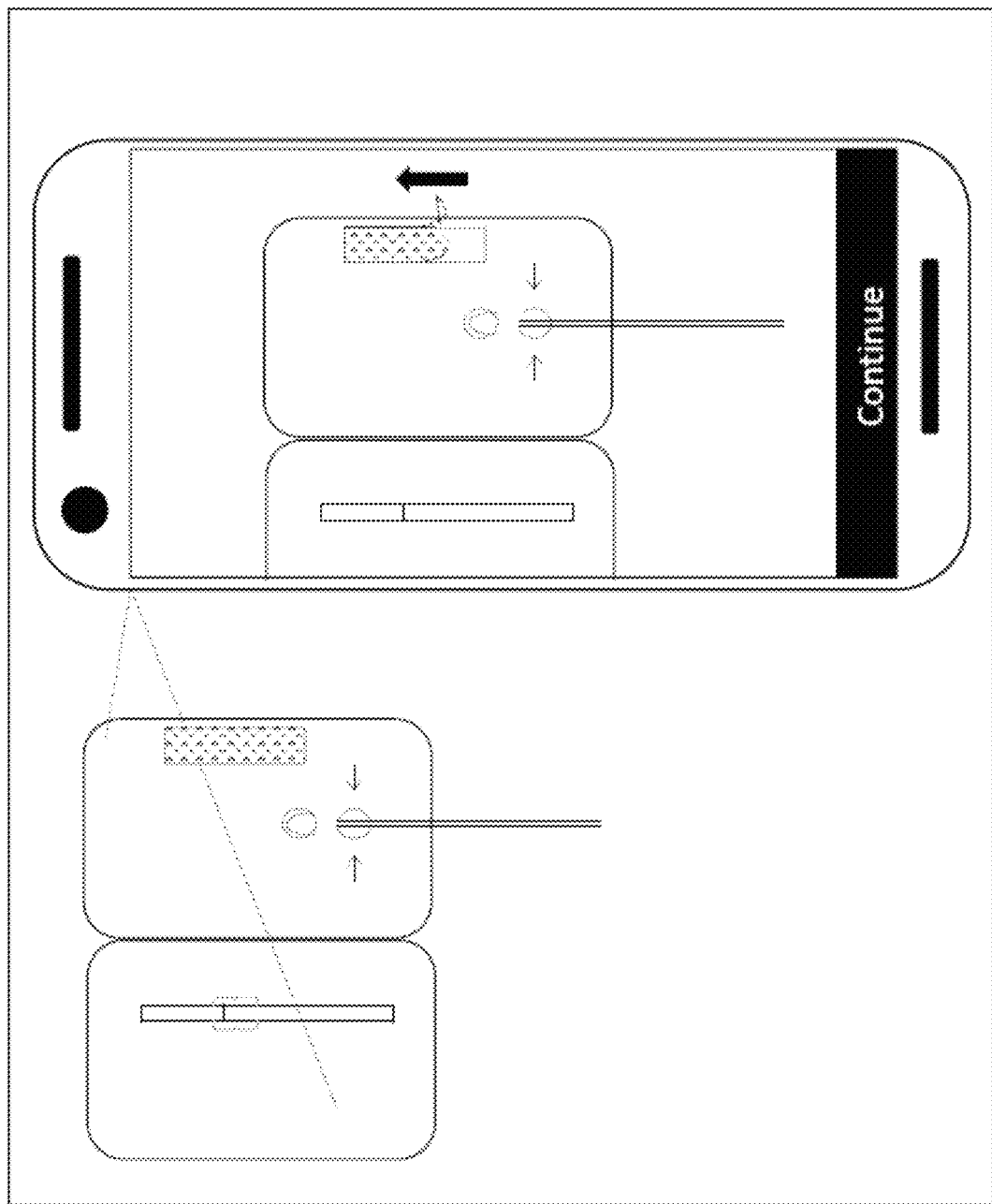
Figure 8I:
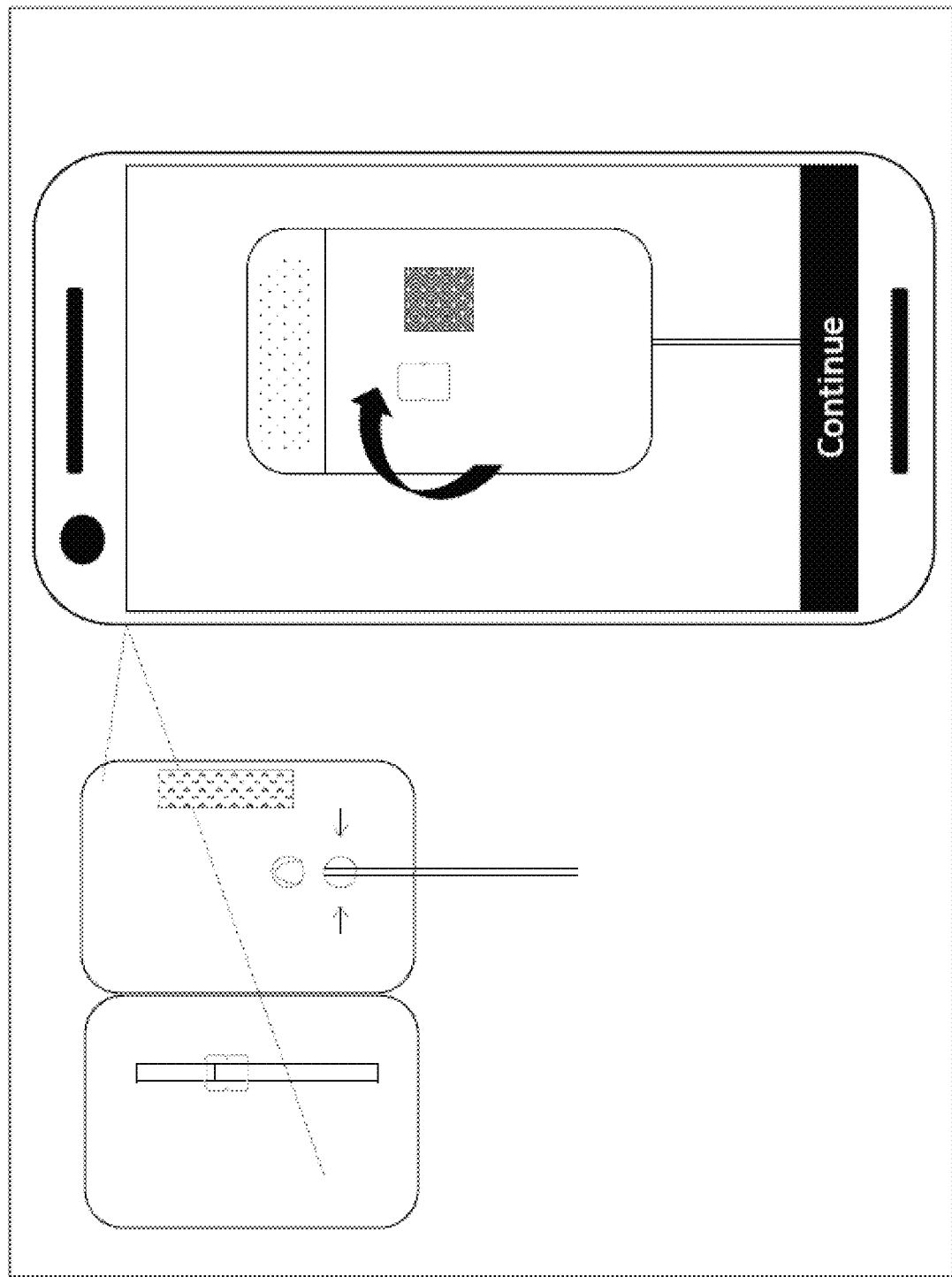
Figure 8J:
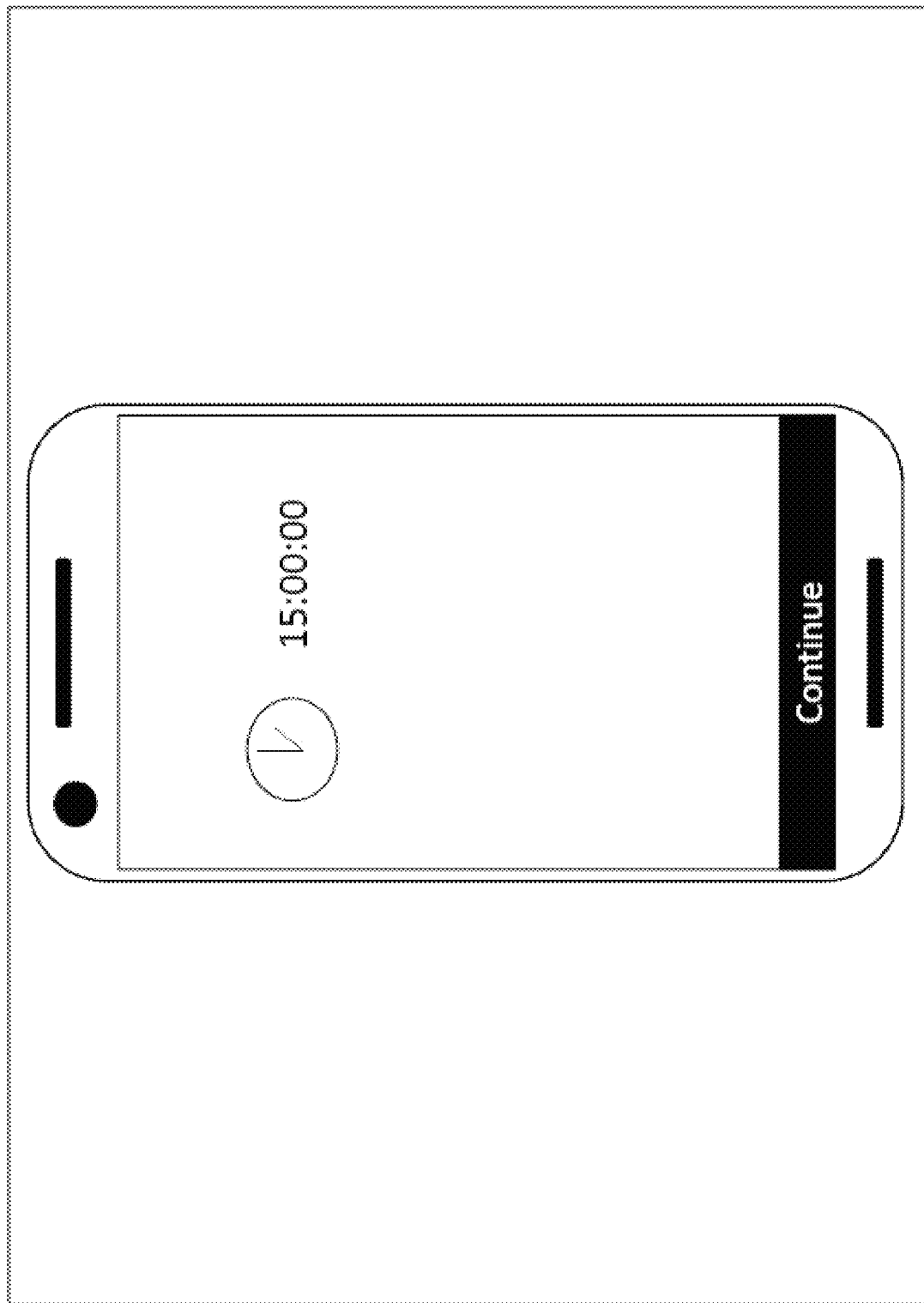

FIG. 8G includes a virtual image or animation of an arrow and a cotton swab stick guiding the user to insert the tip of the cotton swab stick that was inserted and rotated within the nostril into the indicated lower hole on the COVID-19 test kit. FIG. 8H includes a virtual image or animation of an upward-directed arrow and the cotton swab stick guiding the user to advance the cotton swab stick upward until the cotton tip of the cotton swab tip is visible within the upper window or hole of the COVID-19 test kit. The upward arrow may also indicate to the user that a covering of an adhesive strip on the exterior of the COVID-19 test kit should be removed. FIG. 8I again includes a curved arrow virtual image or animation to guide the user to fold the two portions of the COVID-19 test kit together to seal the portions together to facilitate testing of the sample. FIG. 8J shows a screen display including a timer to guide the user as to how long to wait until the results can be viewed for accuracy.

Figures 9A, 9B:
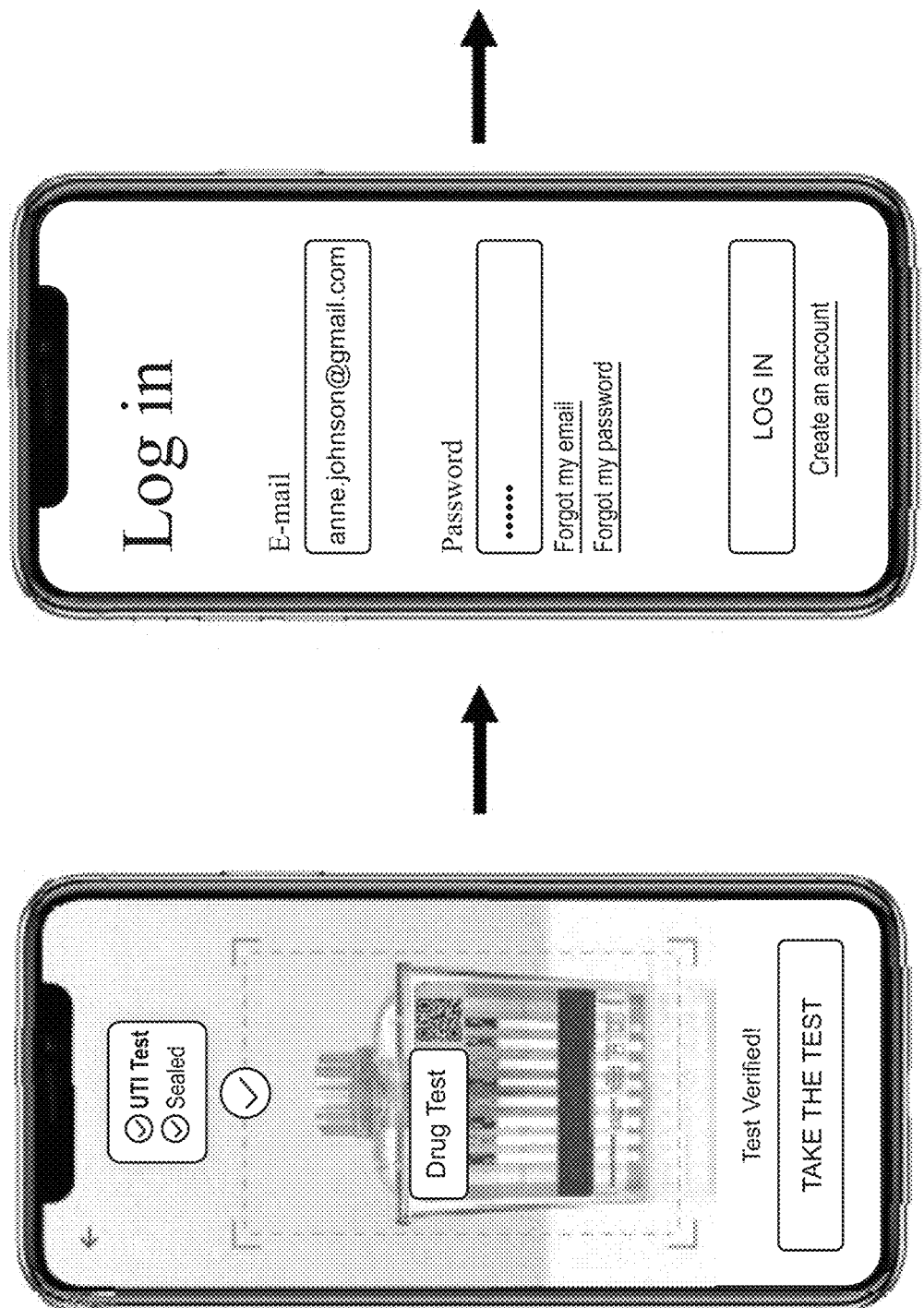
FIGS. 9A-9F illustrate a series of example screen displays that can be displayed to a user to guide the user through the steps of administering an at-home drug test according to some embodiments described herein.

FIGS. 9A-9F illustrate a series of example screen displays that can be displayed to a user to guide the user through the steps of completing an at-home drug test according to some embodiments described herein. Again, the screen displays may include augmented reality display content that is overlaid on real-time, real-world camera images of components or portions of the medical diagnostic test kit 115 and/or the user. FIG. 9A shows a screen that may be displayed after scanning of the machine-readable code 120 on a drug test kit and provides a user-selectable option on the graphical user interface (e.g., a user-selectable button) to facilitate receipt of user input data to proceed with administration of the medical diagnostic test.

In some implementations, as shown in FIG. 9B, the user must log in to the health testing platform or Web application prior to proceeding with the diagnostic test (e.g., drug test) in order to authenticate the user and to facilitate tracking and processing of test results and/or generation of a virtual pass upon completion of the testing process. FIG. 9C shows a screen display in which textual instructions are provided to the user guiding the user as to what to do. A visual image is also displayed to visually show the user the step to complete. A box is overlaid on the image so that the user can fix his or her face within the box while performing the testing step of swabbing his or her mouth with a swab located in the drug test kit. The display further includes a countdown timer.

Figure 9D:
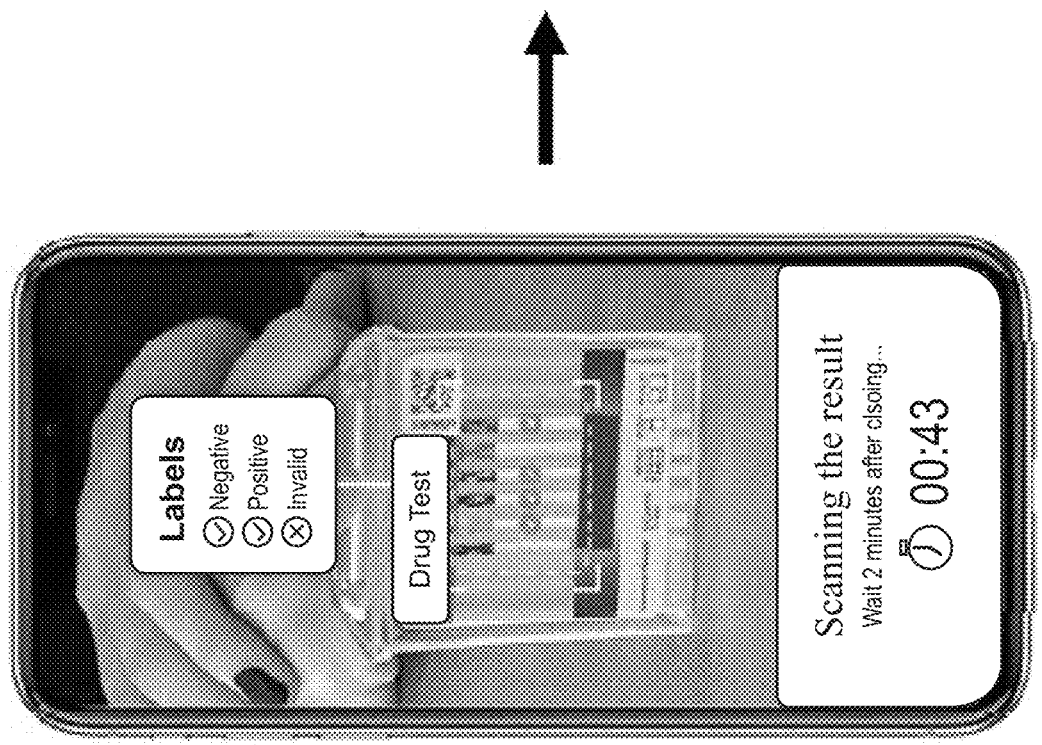
Figure 9C:
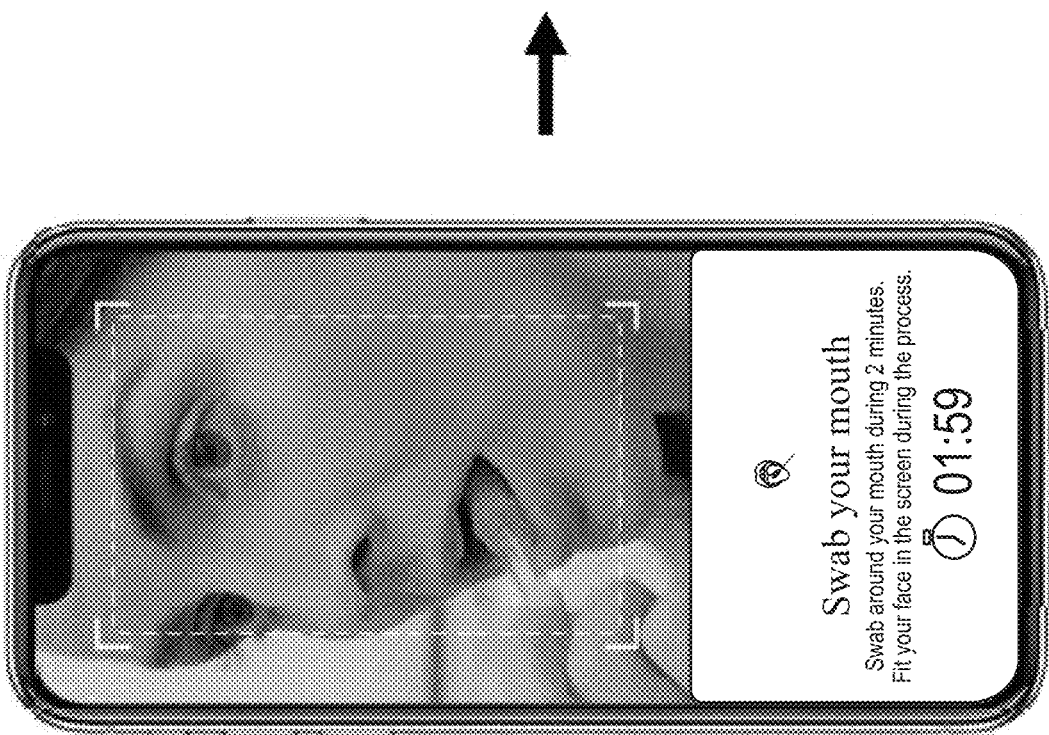
Figures 9E, 9F:
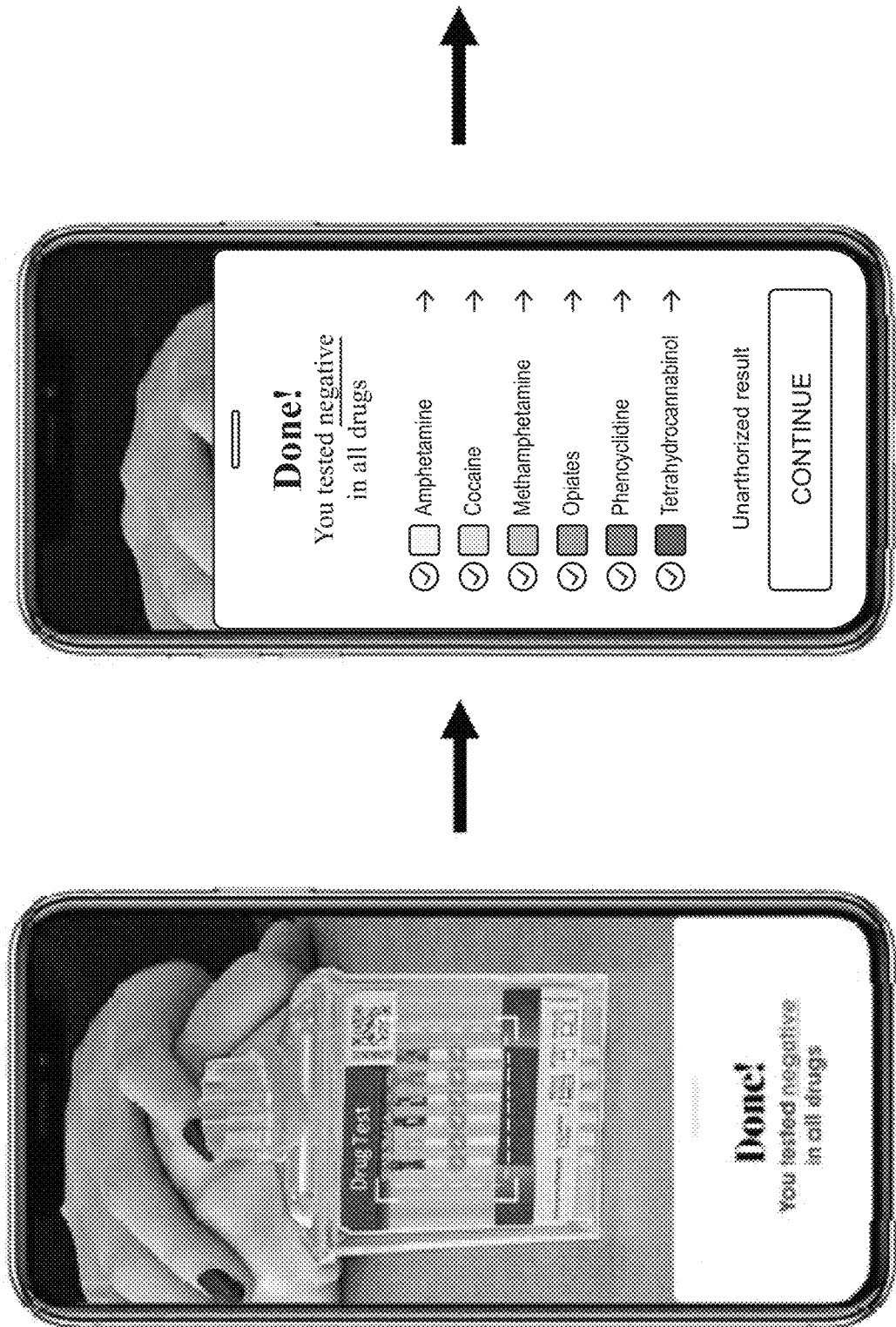

FIG. 9D includes instructions and a countdown timer guiding the user to wait to scan or take an image capture of the results until after a certain amount of time. The display may also include overlaid information as to how to interpret the test results. FIG. 9E indicates the test results to the user. The display may also include overlaid virtual content showing a box to guide the user as to what portion of the test kit to capture with a camera of the user device in order to capture the drug test results in the image. FIG. 9F displays more detailed test results and provides an option for the user to obtain more information regarding the test results. In some embodiments, the systems disclosed herein are configured to determine test results based at least in part on images captured of a medical diagnostic test, such as a UTI or drug test, and overlay subsequent images of the diagnostic test as displayed on a user device with graphics indicative of the determined test results. In some examples, these graphics may highlight or point out specific regions, markers, or features on testing materials that are indicative of results, along with graphics indicating what those results are determined to be. For instance, test results may be determined by way of computer vision techniques and/or human observation and interpretation of images of the medical diagnostic test. Such human observation and interpretation may be provided by a guide, medical professional, or other person with which the user is connected during the testing session. In some examples, such as those in which a drug test or COVID-19 test is administered, the user may be connected with one or more persons who serve to proctor one or more portions of the testing session. This may enable testing results to be verified and optionally reflected in a pass that is provided to the user after the test has concluded.

Figure 9G:
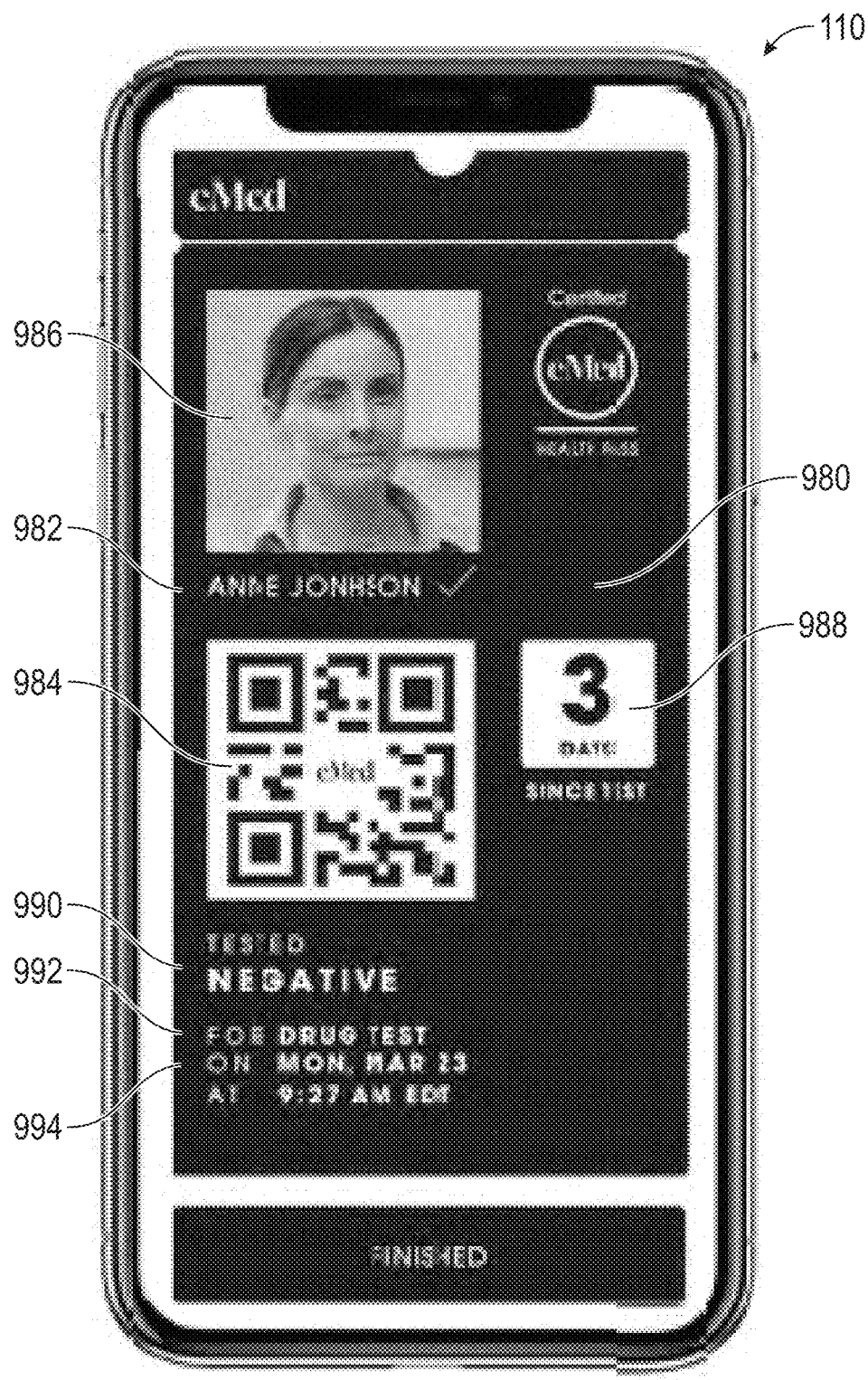
FIG. 9G illustrates an example of a virtual test pass that can be generated following completion of one of the at-home medical diagnostic tests contained within the medical diagnostic test kit container of FIG. 1 according to some embodiments described herein.

FIG. 9G illustrates an example of a certified virtual test pass 980 that can be generated by the provider health platform following completion of one of the at-home medical diagnostic tests contained within the medical diagnostic test kit container or package 100, such as the drug test or a COVID-19 test. The virtual test pass 980 may comprise a digital test completion pass that may be shown or displayed on a user device (e.g., mobile phone or tablet) or sent via email or text message to a recipient requiring proof of the test results.

The test pass 980 can be provided and associated with the remote health testing and diagnostic platform that is used to identify the user and communicate the user's test results. In some implementations, the test pass 980 can be provided at and/or used to verify a user's identity at a point of care, such as the location where the test is taken (e.g., a medical facility, a care facility, an assisted living center, a home, a hotel, an airport, a etc.), and also used to verify the user's test results at a point of verification (e.g., a location where the user's results are checked (such as the airport, a hotel, a place of employment, etc.). In some implementations, the point of care and the point of verification may be different. For example, a user may take the test at his or her home and receive the test pass 980 and then can use the test pass 980 to verify his or her results at the airport. In some implementations, the point of care and the point of verification may be the same. For example, a user desiring to board a flight at an airport can take a test and receive a test pass 980 at the airport and then use that pass to verify the results and board a flight.

In some implementations, the test pass 980 can be configured to perform one or more of several functions. For example, the test pass 980 can include proof of the user's identity. For example, in FIG. 9E, the test pass 980 includes personal information 982. The personal information 982 can include the user's name and other identifying information such as photo or other biometric information. The test pass 980 can be configured to show this information to prove the user's identity at a point of care (e.g., at medical facility or home at which the test is taken) and at point of verification (e.g., at an airport, stadium, etc., where the test result is checked). In some implementations, the test pass 980 includes a positive identifier that checks or verifies the user's identity against a driver's license, passport, or other verifiable biometric data. In various implementations, identity verification using the test pass 980 should be simple and quick. Additionally, the test pass 980 should be configured such that the results reported by the test pass 980 should be able to be trusted at point of verification. For example, the test pass 980 can ensure that results stored on the pass were gathered using an FDA-approved method. The test pass 980 can also be configured for information security. For example, the test pass 980 can provide the user with a mechanism for controlling who accesses their data and when.

A test pass 980 can be provided in either a physical or virtual manner. For example, a physical test pass may comprise forgery-resistant card provided by the test pass issuer that includes user's name and photo for identification. The physical test pass may also include a barcode, QR code, NFC chip, contact chip, alphanumeric code, or other unique identifier that will access test results from a secure database when scanned. A virtual test pass, or digital health pass, may be available over a computer network or through a Web application. When accessed, it can display a machine-readable code 984 (e.g., QR code) or use NFC or other means for quick communication at point of verification. The machine-readable code 984 may direct interested parties to a webpage containing additional information about the patient, the test, the test results, and/or other tests that the patient has undergone. In some implementations, the test pass 980 can be linked to a user's existing ID. For example, test results can be linked to an existing form of ID by name and unique number (driver's license number, passport number, etc.). In some configurations, the user must have this ID at point of care and point of verification, where their name and unique number are used to access results from a secure database. The test pass 980 may also include a photo 986 of the user, an indication of the number of days since the test 988, a general result of the test 990, a test type 992, and further details regarding date and time of the test result 994. In addition, the test pass 980 may comprise an expiration, which may comprise easily accessible information regarding expiration of the dependability of the test result based on health guidelines provided by government entities or otherwise.

In some implementations, each user is provided with a new virtual test pass 980 each time they complete a test. For example, a user may be provided with a new virtual test pass indicating the most recent test result. In other implementations, in which the user already has a test pass, upon completion of a new test, the existing test pass can be updated to include the most recent result. For example, the machine-readable code 984 on the virtual test pass 980 may be linked to the newest test result.

In some implementations of the virtual test pass 980, the user's ID may be verified each time that the virtual test pass is displayed. For example, the user may be required to be biometrically authenticated each time the virtual test pass 980 is to be displayed. As one example, the user may use face recognition on his or her phone in order to verify his or her identity before the virtual test pass 980 can be displayed.

FIGS. 10A-10H illustrate a series of example screen displays that can be displayed to a user to guide the user through the steps of completing an at-home UTI test according to some embodiments described herein. The screen displays may include augmented reality display content that is overlaid on real-time, real-world camera images of components or portions of the medical diagnostic test kit 115 and/or the user. As shown, the screen displays may also include infographics, text instructions, and user-selectable content (e.g., buttons) to facilitate receipt of user indication of completion of each step of the testing process in order to continue on to the next step.

FIG. 10A shows a screen that may be displayed after scanning of the machine-readable code 120 on a UTI test kit and provides a user-selectable option on the graphical user interface (e.g., a user-selectable button 123) to facilitate receipt of user input data to proceed with administration of the medical diagnostic test. The display may also indicate verification of the particular medical diagnostic test. In some implementations, as shown in FIG. 10B, the user must log in to the health testing platform or Web application prior to proceeding with the diagnostic test (e.g., UTI test) in order to authenticate the user and to facilitate tracking and processing of test results and potentially later ordering of prescription medication, such as an antibiotic to treat the UTI.

Figures 10C, 10D:
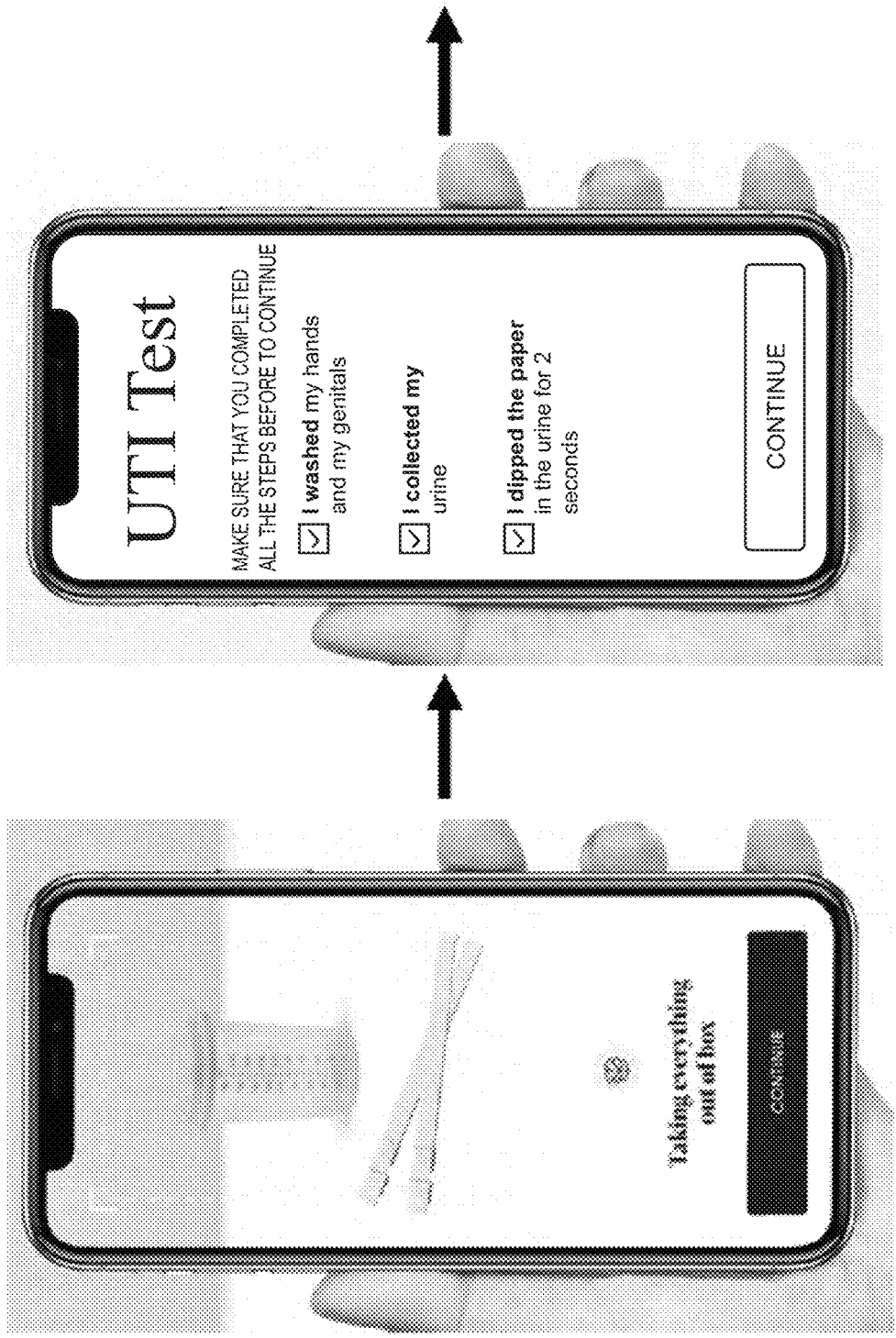

FIG. 10C includes a display that instructs the user to take the contents out of the UTI test kit. The display may also instruct the user to take an image capture of the contents of the UTI test kit prior to testing. FIG. 10D includes a display that instructs the user to complete certain steps in the UTI testing process. The graphical user interface may include checkboxes that a user must check in order to continue with the testing process. Because certain tests may involve interaction with private body parts of the user, the camera and overlaid augmented reality content may not be used during certain parts of the testing process for privacy reasons.

Figure 10F:
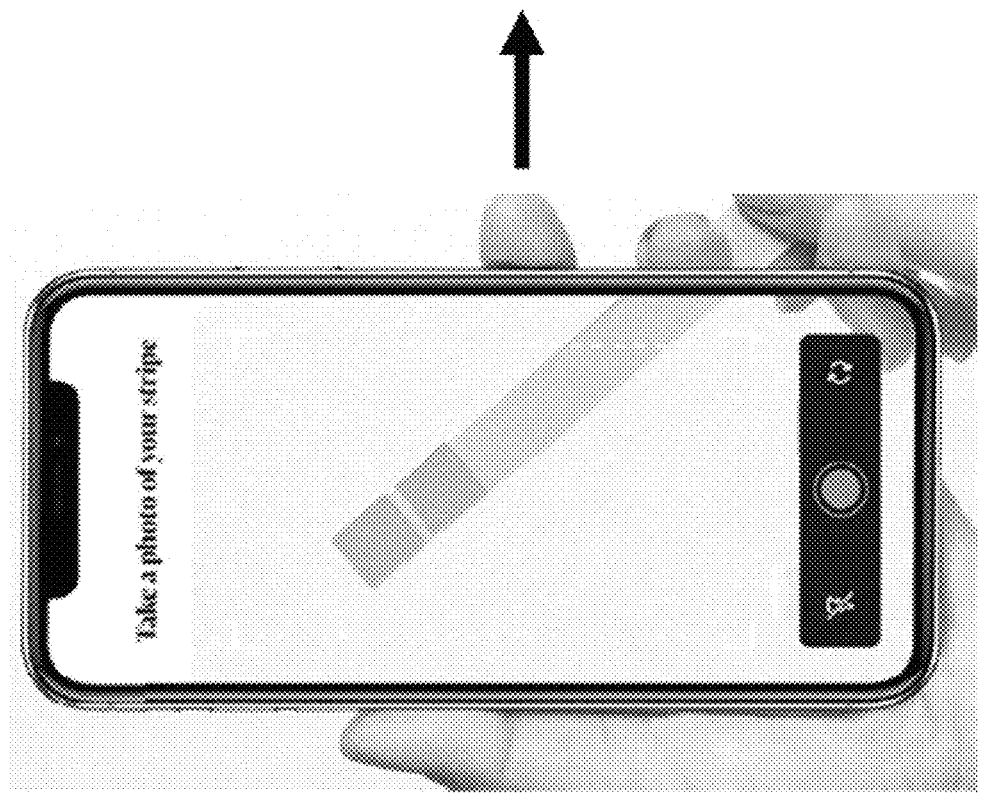
Figure 10E:
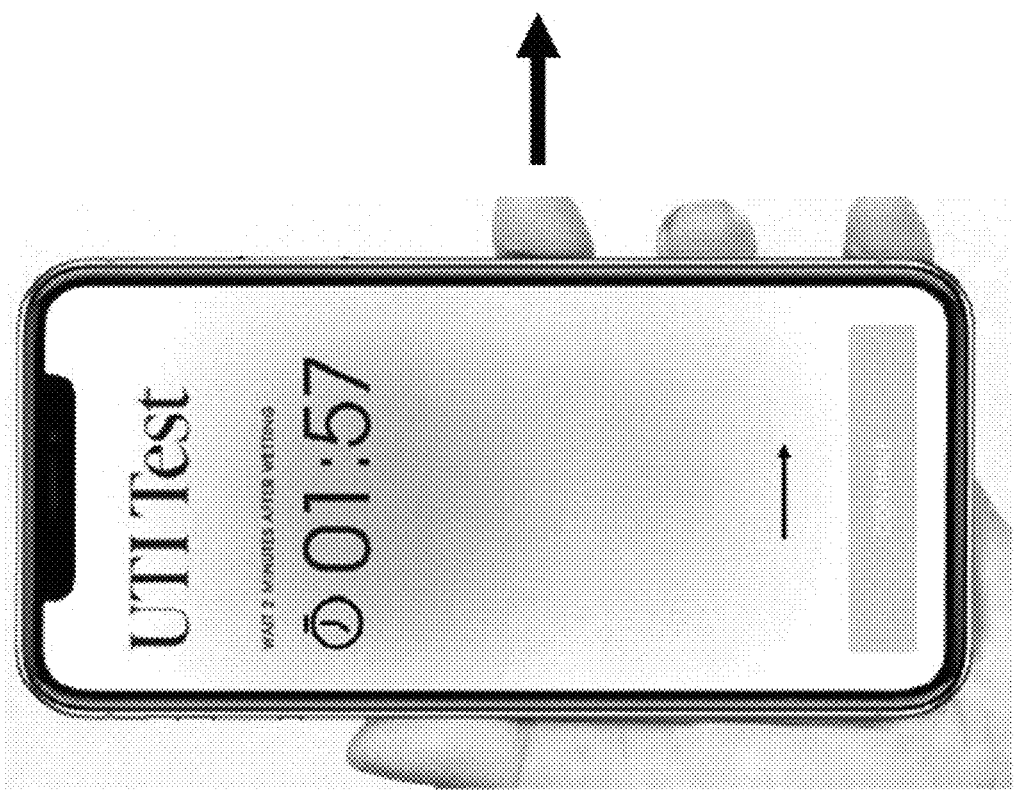
Figure 10H:
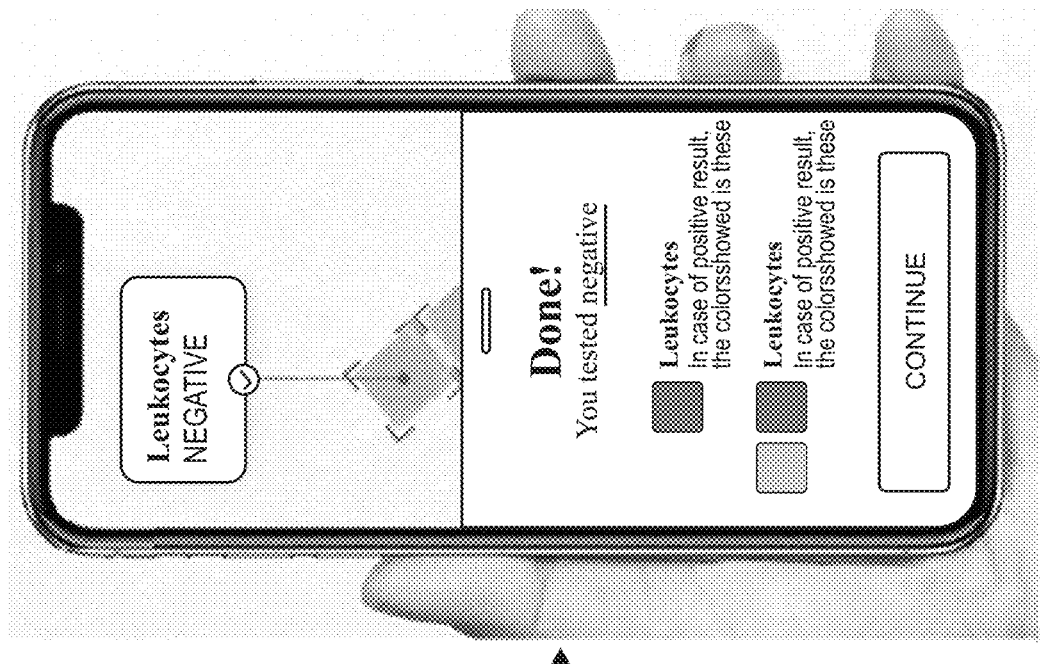
Figure 10G:
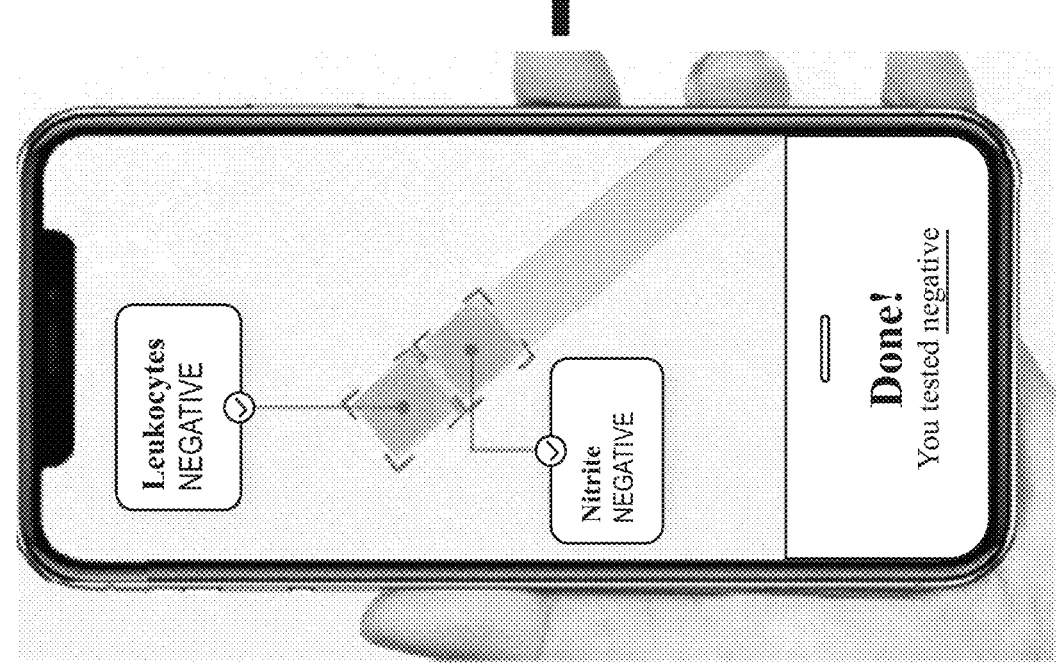

FIG. 10E shows an example screen display including a timer to guide the user as to how long to wait until the results can be viewed for accuracy. FIG. 10F instructs the user to take a photo of a portion of the test strip indicative of the result and facilitates the image capture process. FIG. 10G show example displays indicating the test results to the user along with additional details for more information.

In several implementations of completion of the medical diagnostic tests, such as those described above, the user device 110 may be positioned such that the user is visible within the field of view (FOV) of the user device's forward-facing camera and the medical diagnostic test kit 115 is positioned within the FOV of the user device's rearward facing camera. Such a set up may be advantageous as it allows the user and the medical diagnostic test kit 115 to remain within the different FOVs of the forward and rearward facing cameras of the user device 110 during the entire testing procedure. Further, at different portions of the procedure, the output of the frontward or rearward facing camera can be displayed to the user and supplemented with AR-based guidance.

For example, during one portion of the testing procedure, the output of the rearward facing camera (e.g., FOV in which is positioned the test kit 115) can be displayed to the user such that the user can view the test kit 115 on the display of the user device 110. The display can be updated with AR-based guidance to highlight certain areas of the test kit 115 or items in the test kit 115 or overlaid with other types of instructions to aid the user in performing the testing procedure. During another portion of the testing procedure, the output of the frontward facing camera (e.g., FOV in which the user is positioned) can be displayed to the user such that the user can view his or herself on the display of the user device 110. The display can be updated with AR-based guidance to highlight certain areas of the user (e.g., a nostril) or overlaid with other types of instructions to aid the user in performing the testing procedure.

Although the figures have illustrated examples of AR-based guidance in cases where the user device comprises a smartphone, AR-based guidance can also be provided for other types of user device. For example, in the case of a laptop, the aforementioned camera might be a camera on the laptop located above the screen. In the case of a smartphone, the aforementioned camera might be an inward-facing camera on the front of the smartphone above the screen. Accordingly, in some smartphone embodiments (or other embodiments where the user device includes both forward- and rearward-facing cameras) some steps may be performed using the forward-facing camera and some steps can be performed using the rearward-facing camera. The display shown to the user (e.g., on the screen on the front of the device) can change from the forward- to the rearward-facing camera depending on the step being performed. In some embodiments, the change of cameras occurs automatically.

In some examples, the user may place the smartphone in a smartphone stand, and may be instructed to position the test kit in front of the smartphone such that both the user and the test kit are visible in the inward-facing camera on the front of the smartphone above the screen. With continued reference to examples where the user accesses the platform using a smartphone, the user may be instructed to seat themselves at a table (with a flat surface), place the test kit on the table about 1.5 to 2 feet from the edge of the table, place their smartphone in a smartphone stand (e.g., that is included in the medical diagnostic test kit container 100), and position the smartphone in the smartphone stand on the table between themselves and the test kit such that their face and upper body is within the field of view of the smartphone's inward-facing camera and the test kit is within the field of the smartphone's outward-facing camera. Depending on whether the user is being given test kit guidance or sample collection guidance, the live video feed that's displayed for the user and overlaid with graphics may switch between the outward- and inward-facing cameras.

Test Integrity and Verification

In some embodiments, during a remote testing procedure, various steps can be implemented before, during, and after the test in order to ensure test integrity and verify the result of the test. For example, before the test is taken, it can be desirable to verify the user's identify and to verify that the test kit is valid (e.g., to verify that the test kit is one that has been purchased or otherwise obtained through an official channel, has not expired, and has not been previously used). During the test, it can be desirable to verify that any sample obtained is actually obtained from the previously verified user and that all test instructions and procedures are followed correctly. Finally, after the test, it can be desirable to ensure that the test result is obtained from the previously verified test kit and to ensure that the test result is interpreted correctly.

As noted above, it can be important to verify the user's identity before the test is taken. This can be because it ensures that the results will be attributed to the correct person. Verifying the user's identity is particularly important in cases of remote testing as the person being tested is not physically located with the person administering the test. Thus, in many situations, extra precaution may be advantageously taken to correctly identify the user's identity. Verification of the user's identity can be accomplished in several ways. For example, the user can be asked to upload a copy of an official identification (e.g., a driver's license or passport) as part of an account creation or pre-qualification step. In some embodiments, the user may be asked to show the official identification to the proctor during the testing session. During the testing session, the proctor can then compare the uploaded or shown identification to the person's appearance in the video feed. In this way the proctor can verify the user's identity by comparing a live (or other) video feed of the user to an identification card associated with the user. In some embodiments, once the user's identity is verified, the user's identity can be associated with the user's account for future tests. For example, after verification, future verifications may be automated with face matching technology.

In another example, user identification can be achieved using biometrics. For example, in some embodiments, a user accessing the platform may be given the option to perform a biometric initialization, in which the user goes to a physical location where their fingerprint or a unique segment of DNA can be sampled and stored. Thereafter, every test taken can sample their fingerprint or DNA to verify identity. This may also be automated. In other embodiments, biometrics may be performed using biometric features of the user's device. For example, many smartphones today are capable of taking a user's fingerprint or recognizing a user's face. These features may be used to verify the user's identity in some embodiments.

In addition to verifying the user's identity, the test or test kit that will be used during the test may be verified as well. This can be important because it ensures that the test results are scientifically valid and can be trusted. Again, this can be particularly important in the case of remote testing where the user is not physically located with the person administering the test. In one embodiment, the test or test kit can be provided with a unique ID (e.g., a UID or serial number) assigned during manufacture, which can be queried when the test is taken. This can take the form of a printed string of characters, barcode/QR code, NFC/RFID tag, or other. This code may either explicitly encode information associated with the test (such as a test identifier, test expiration date, batch/lot codes, indication of whether this number has been used for a test or not) or it may encode a link to a database entry that includes such information. Prior to beginning the test, the code may be scanned to verify the test kit. If anything is amiss, the test does not proceed and the user may be instructed to obtain a new test kit. In some embodiments, it may be preferable to provide the unique ID in a non-human readable manner. This may provide an advantage in that they are harder to misrepresent. A visible code could be duplicated and used on an expired test, for example.

During a test, a sample may be collected from the user, for example, using the test kit. To ensure the integrity of the test, steps may be taken to ensure that the sample is actually collected from the same user whose identity was verified before beginning the test. Again, this can be especially important in the case of remote tests since the user is not physically located with the person administering the test. It can be important to ensure that a user does not swap in a sample obtained from another user when performing the test. Various mechanisms for verifying that the sample is collected from the previously verified user are possible. For example, during a proctored testing session, the proctor (or an automated system) can observe the sample collection process. For example, in the case of a nasal swab test, the proctor or the automated system can observe the user performing the swab procedure. Such observation can be performed live (e.g., over a live video connection) or through a pre-recorded video. In either event, it may be important that all sample collection materials remain in view of the camera at all times. This would prevent a user from swabbing his or her nose and then switching out the swab with another that has been used by a different person. Additionally, it may be beneficial to positively identify the user during the collection process. This can be accomplished by, for example, checking the user's identity immediately before the sample collection process.

During the test, it is also important to ensure that all test instructions and procedures are followed correctly. This can ensure the accuracy and validity of the test results. Similar to verifying that the sample is obtained from the correct user, ensuring that all test instructions and procedures are followed correctly can be accomplished by directly viewing the testing procedure, either over a live video feed or be watching a recording of the testing process. In some embodiments, such observation is provided by a live proctor. In some embodiments, such observation is provided through an automated system (e.g., a computer system that is configured to analyze live or pre-recorded video). In the case of a swab, for example, the swab can include stripes or other markings along its length to be able to quantify swab insertion depth in an orifice, such as a nostril. In this manner, a proctor can easily observe that the swab is inserted to a sufficient depth. Additionally, the automated system can be configured to recognize the stripes or markings on the swabs in the video to automate determination of proper insertion depth. In some embodiment, in which test a test must sit for a certain amount of time (e.g., dwell example), the user can be instructed to place the test on a suitable surface in view of the camera for an appropriate amount of time. The proctor or system can observe that the test is placed on the appropriate surface and remains in view during the entire dwell length. In the case of a nasal swab COVID-19 test, for example, an appropriate amount of liquid may need to be added to a testing card, a nasal swab may need to be inserted into the nostril to a sufficient depth, the swab must then be correctly applied to the liquid on the card, and the card must be left undisturbed on a flat surface for at least fifteen minutes. Each of these steps can be observed and verified by a proctor and/or an automated system to ensure the integrity of the test.

Additionally, it is important to ensure that submitted test results actually come from the originally verified test or test kit. This can ensure test continuity, making sure that the same test is used throughout the test (e.g., that the test that was verified is the one for which results are obtained). Otherwise, tests could be exchanged during the process, leading to improper results. In some embodiments, this can be accomplished by reverifying the test or test kit throughout the testing procedure. For example, the method that was used previously to determine the test kit was valid (e.g., scanning the unique ID of the test kit) can be repeated to ensure the UID/serial number are the same. In some embodiments, the test kits can be designed such that the test such that the results are reported in a manner that includes the UID/serial number, such as in a custom visible code (barcode, QR code, etc.) or NFC/RFID, so that when the results are read, the UID can be verified. For example, in some embodiments, test results are verified by viewing strips that appear on a test card. The test card can include the unique ID of the test kit near the area at which the strips will appear such that a view of the strips also includes a view of the unique ID.

Finally, it can also be important to ensure that the test results are interpreted correctly. As described previously, in some embodiments, a proctor interprets the test results by viewing strips that appear on a test card, for example. In some embodiments, an automated system may interpret the test results. In some embodiments, the test results can be reviewed and verified by another proctor or automated system to provide a second layer of verification.

At-Home Medical Diagnostic Test Kit Container Labels and Inserts

FIG. 11 illustrates an example of a graphic label 1100 (including a machine-readable code 120) that can be printed on or adhered to an external surface of a medical diagnostic test kit 115 within the medical diagnostic test kit container or package 100. In various implementations, the external surface may be a top external surface, a bottom external surface, or an inner surface (e.g., underside of lid). As can be appreciated, the graphics can be arranged or altered as desired and/or required. The graphic label 1100, or variations thereof, may also be positioned on multiple external and/or internal surfaces of the medical diagnostic test kit container 100.

Figure 12:
FIG. 12 is an example of a graphic label (including a machine-readable code) that can be printed on or adhered to an external surface of the medical diagnostic test kit container or package of FIG. 1 according to some embodiments described herein.

FIG. 12 is an example of a graphic label 1200 (including a machine-readable code 105) that can be printed on or adhered to an external surface of the medical diagnostic test kit container or package 100. In various implementations, the external surface may be a top external surface, a bottom external surface, or an inner surface (e.g., underside of lid). As can be appreciated, the graphics can be arranged or altered as desired and/or required. The graphic label 1200, or variations thereof, may also be positioned on multiple external and/or internal surfaces of the medical diagnostic test kit container 100. As shown, the graphics of the graphic label 1200 include an indication of the types and quantity of each type of medical diagnostic test kits located within the medical diagnostic test kit container 100. As can be appreciated, the graphics can be arranged or altered as desired and/or required.

FIGS. 13 and 14 are examples of graphic labels or inserts that may be provided on or inside the medical diagnostic test kit container or package 100 according to some embodiments described herein. The labels or inserts or graphics of FIGS. 11-14 may indicate the types of tests included, general instructions regarding an overview of the remote at-home testing process, and additional details regarding how the test results can be validated and certified so that the test results can be used to facilitate travel or to comply with testing requirements.

The labels or inserts or graphics of FIGS. 11-14 may also include (i) a QR code or other machine-readable code or computer-readable graphic that, when scanned by a user device, directs the user device to one or more resources (e.g., web pages, application screens, etc.) that are associated with the medical diagnostic kit container 100 and/or one or more of the medical diagnostic test kits 115 associated therewith, (ii) steps or directions for taking any of the medical diagnostic tests associated with the container 100 and/or starting a proctoring session for verifying the results of any of the medical diagnostic tests, (iii) information on how to obtain treatment for conditions associated with any of the medical diagnostic tests, (iv) information on the contents of the box, (v) information on the health pass that can be obtained upon testing negative on any of the medical diagnostic tests, or a combination thereof. As can be appreciated, the graphics can be arranged or altered as desired and/or required.

Self-Administered Treatment

Self-administered treatments may be used for the treatment of certain conditions. For example, multiple oral medications for the treatment of Covid-19 have obtained emergency use authorization. These medications must be prescribed by a healthcare professional (which may be a physician, pharmacist, or other healthcare professional authorized to prescribe treatment), but the patient can take the medication at home. Remote prescription carries several advantages for self-administered treatment. Patients can obtain treatment conveniently at home and without having to go to an in-person provider visit. This is not only advantageous for the patient who can obtain treatment with reduced inconvenience and delay but may also reduce community spread of disease as the patient can stay home instead of traveling to seek medical care. In some cases, medications may be sent directly to the patient's home or may be filled at a pharmacy of the patient's choosing.

In some embodiments, a testing platform may interface with prescribers in a manner that is transparent to the user. For example, the user may take a test, receive a result, and obtain treatment all within the testing platform, with no apparent discontinuity, although a prescribing partner may be a different entity from the provider of the testing platform. In some cases, a third entity may be engaged to facilitate the delivery of treatments to patients, and this too may be done in a manner that is transparent to the user. For example, the user may be able to track prescription fulfillment status, delivery status, and so forth through an application or website offered by the testing platform. In some embodiments, the user may be transferred to third parties for treatment fulfillment. For example, a user who receives a positive Covid-19 test may be directed to a pharmacy that can provide treatment to the user.

Figure 15:
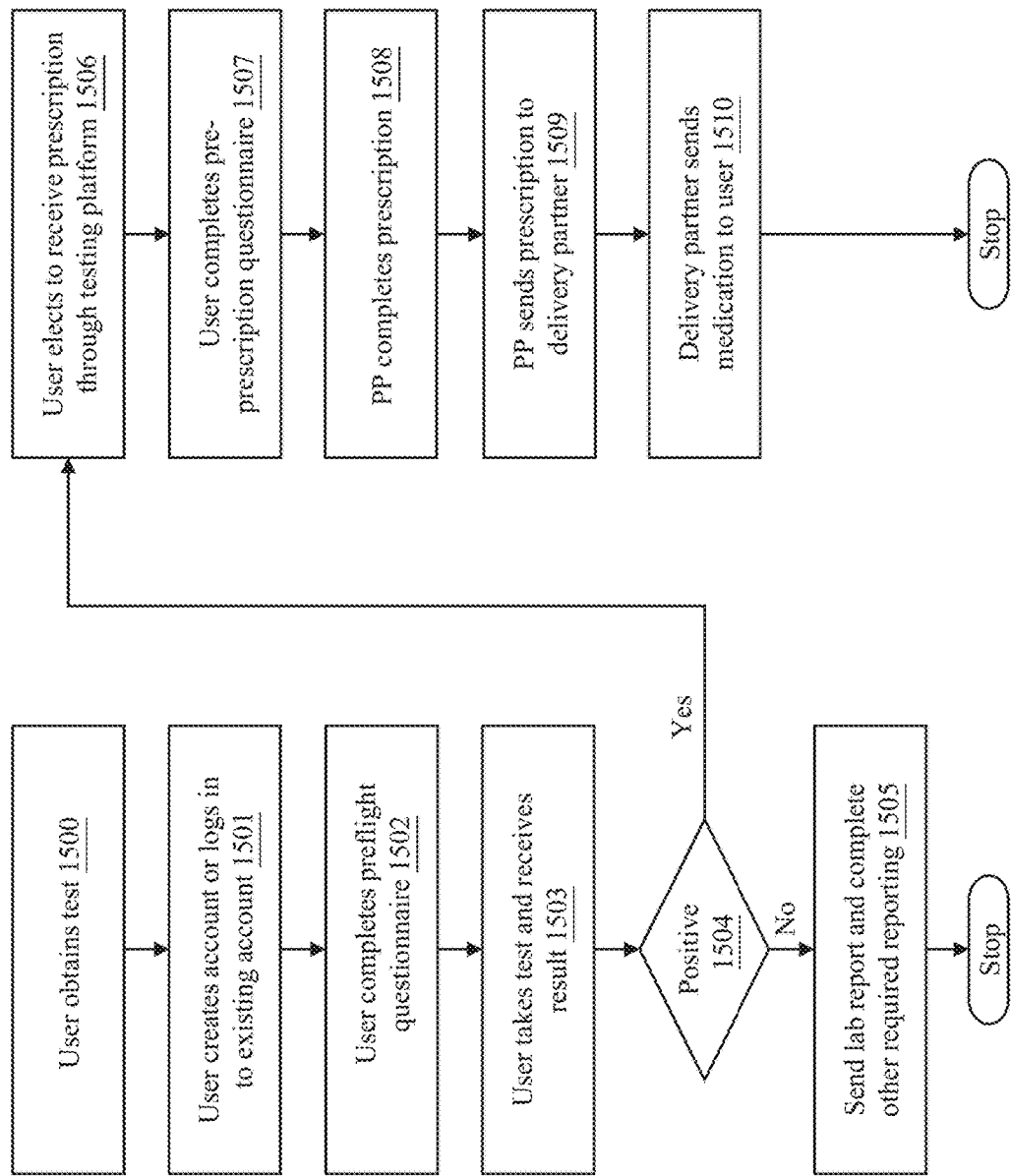
FIG. 15 is a block diagram illustrating testing and treatment according to some embodiments.

FIG. 15 is an illustration of providing self-administered treatment to a user according to some embodiments. At 1500, a user obtains a test. At 1501, the user signs into the testing platform, either by creating a new account or by logging into an existing account. At 1502, the user completes a pre-flight questionnaire. The pre-flight questionnaire may include, for example, the minimum information required by the testing platform and/or information required to comply with public health requirements. At 1503, the user takes the test and receives a result. At 1504, if the result is negative, the system may send a lab report and the result and information may be used by the testing platform to complete required reporting at 1505. If the test is positive, then at 1506 the user may elect to receive a prescription through the testing platform. At 1507, the user completes a pre-prescription questionnaire. The pre-prescription questionnaire may include questions related to, for example, the user's medical history, medication contraindications, test results, qualifying criteria (e.g., time since the onset of symptoms), and so forth. In some embodiments, the pre-prescription questionnaire may ask questions related to prescribing a single medication or multiple medications. In some embodiments, the user's answers to the questionnaire may be used to select one treatment from multiple available treatments. At 1508, a prescribing partner receives the test results and pre-prescription questionnaire and completes a prescription for the user. At 1509, the prescribing partner sends the prescription to a delivery partner which may be, for example, a mail-order pharmacy, a local pharmacy, or, in some circumstances, the prescribing partner (i.e., the prescribing partner may both issue and fulfill the prescription).

Figure 16:
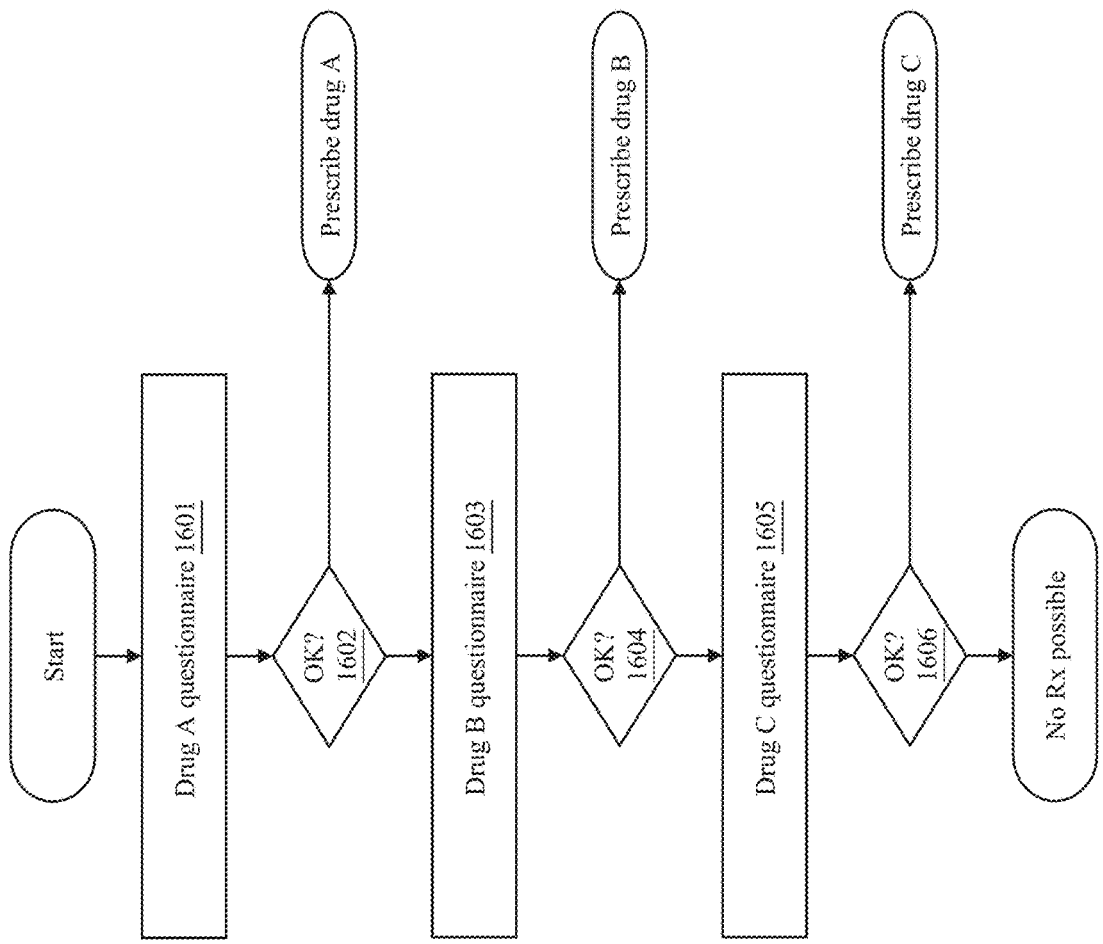
FIG. 16 is a block diagram illustrating a process for determining a treatment to order according to some embodiments.

FIG. 16 depicts a drug selection process according to some embodiments which may be implemented on a computer system. At 1601, a user completes a questionnaire to determine whether a first drug is an appropriate treatment for the user. For example, the first drug may be an oral medication with a high efficacy rate and the questionnaire may determine whether the user has any conditions or allergies or takes any other medications that would contraindicate the first medication. The questionnaire may ask about health insurance coverage, as not all insurance plans may cover all medications. If, at 1602, the system determines that the first drug is okay to prescribe for the user, then the system may proceed with steps for prescribing the first drug, such as sending patient information, test results, and questionnaire responses to a prescribing partner. If, on the other hand, the system determines that the first drug should not be prescribed to the user, the system may present an additional questionnaire for a second drug. The second drug may be, for example, an oral medication with a lower efficacy rate than the first drug. Similarly, the system may present the user with a questionnaire related to a third drug. The third drug may be an injectable, for example, or an oral drug with lesser efficacy than the first drug and the second drug. If none of the available drugs are appropriate for the user, the system may determine that no prescription is possible.

While FIG. 16 illustrates three potential drugs, any number or questionnaires could be presented to screen for any number of medications. In some embodiments, it may be advantageous to combine questions related to different medications into a single questionnaire instead of multiple separate questionnaires. In other embodiments, multiple questionnaires may be used, but responses to earlier questionnaires may be used to avoid asking the user the same questions more than once. For example, if two medications have osteoporosis as a contraindication, there is no need to ask the user about osteoporosis more than once.

Figure 17:
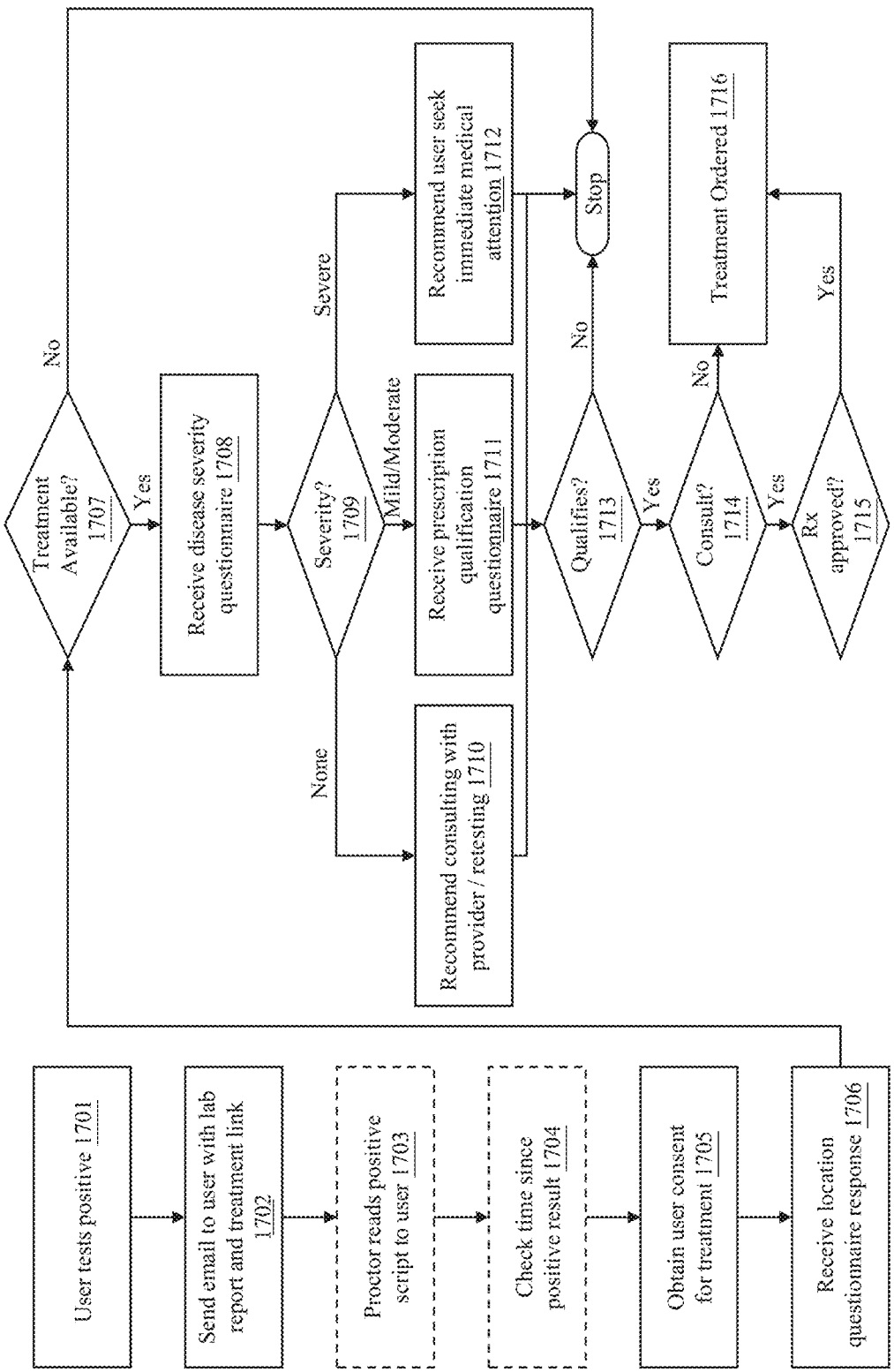
FIG. 17 is a block diagram illustrating testing and treatment determination according to some embodiments.

FIG. 17 illustrates a process for prescribing treatment to a user which may be implemented on a computer system. At 1701, a user receives a positive test result, for example by following steps in FIG. 15, 16, or 17. In some embodiments, instead of a positive test result, the user may receive a negative test result but have a known exposure that may warrant treatment (e.g., exposure to Covid-19). At 1702, the system sends an email to the user with a report of the results and a link to treatment. The user may use the link if, for example, the user at first declines treatment but later wishes to pursue treatment, or if the user gets disconnected before treatment can be ordered. At 1703, a proctor may optionally read a script to the user indicating a positive test result and advising the user that treatment may be available. At 1704, the system may optionally check the amount of time that has elapsed since the user received a positive test result. In some cases, users will proceed to the treatment prescription process immediately after receiving a positive test result. However, in other cases, users may at first decline treatment (for example, if they are not having symptoms at the time) and may return later to seek treatment. If the time since the positive test result is over a threshold value, the user may be advised that a new test is needed.

If the time since testing is below the threshold value, the system may ask the user to consent to treatment at block 1705. At 1706, the system may receive a response from the user indicating the user's location. At 1707, the system may determine whether treatment is available based on the user's location. For example, some states may not permit prescribing certain treatments without an in-person visit to a provider. If treatment is available to the user, then at 1708, the system may receive responses to a disease severity questionnaire from the user. If the user has no symptoms, the system may recommend that the user consult with a provider, retest, or wait to see if symptoms appear. If the user has severe symptoms, the system may recommend that the user seek immediate medical attention. If the user has mild or moderate symptoms, the system may provide the user with a prescription qualification questionnaire and may receive responses at block 1711. The questionnaire may inquire as to the user's age, medical history, allergies, insurance, and so forth. At 1713, the system may determine if the user qualifies for a prescription. If the user does not qualify, the system may inform the user of the reason or reasons for disqualification and be advised of other steps the user can take. If the user qualifies for a prescription, the system may then determine at block 1714 whether the user needs to consult with a prescribing partner such as a provider or pharmacist before treatment can be ordered. For example, some states may require that a user meets with a pharmacist before receiving treatment. In other cases, a user's responses to the prescription qualification questionnaire may warrant further inquiry by a prescribing partner. In some cases, the system may provide a mechanism such as text-based chat or video conferencing to allow the user to consult with a pharmacist or provider. If a consultation is not needed, treatment may be ordered without a consultation. If a consultation is needed, however, then the prescribing partner may approve the prescription and order treatment after consultation with the user or the prescribing partner may determine that treatment is not appropriate for the user.

Figure 18:
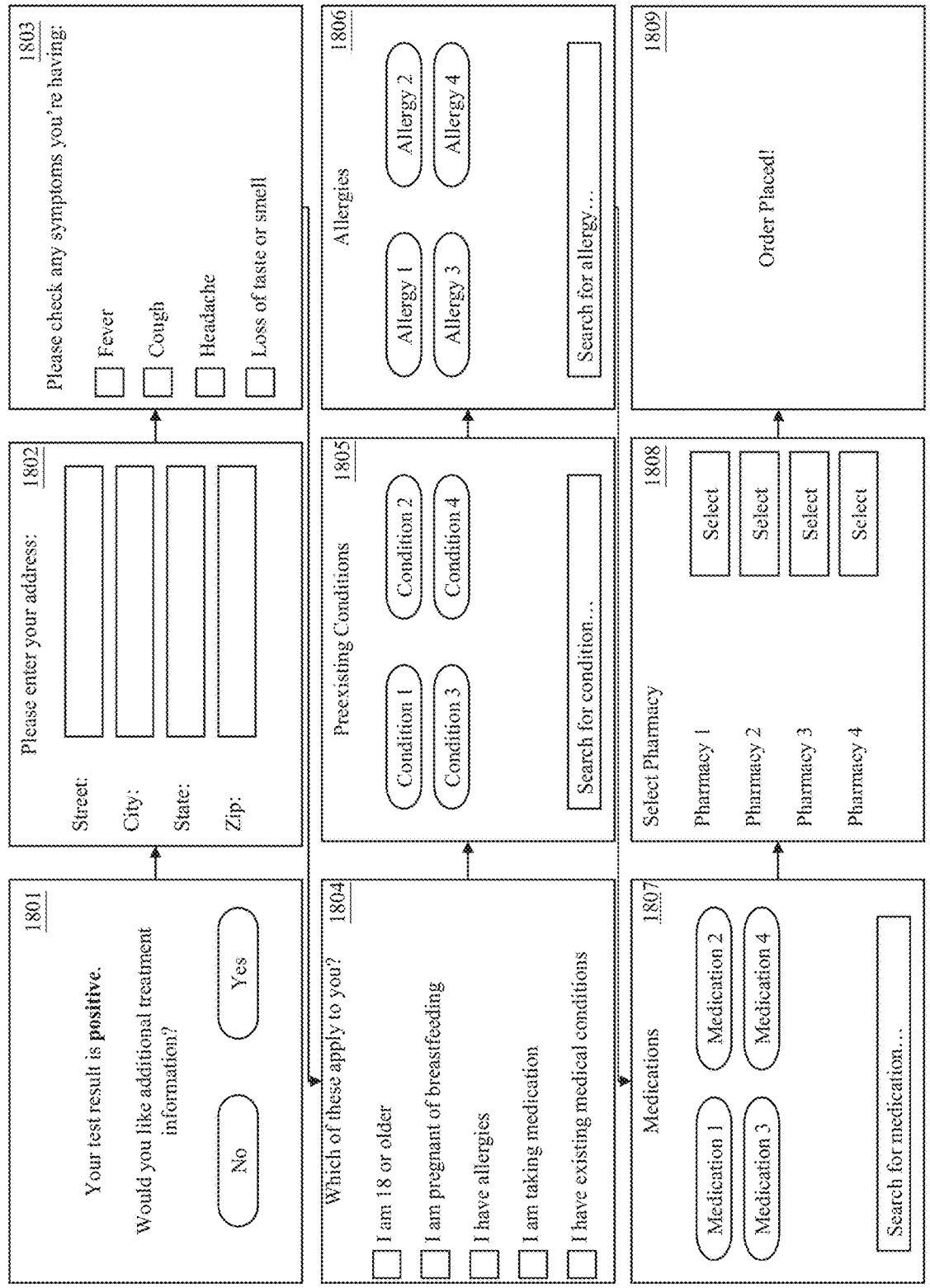
FIG. 18 is a sample user experience for receiving remote treatment according to some embodiments.

FIG. 18 illustrates a series of screens that may be presented to a user following a positive test result. A computer system may be configured to provide the screens to the user. At 1801, the system may show the user a screen indicating that the user's test result is positive. The user may be given an option to receive additional treatment information. If the user chooses to receive additional treatment information, the system may show screen 1802 to the user, where the user may enter location information which may be used to determine whether the user is eligible for remote treatment. If, for example, the user enters a state where remote prescription of treatment is not permitted, the system may abort the questionnaire and display a message to the user explaining why they are not eligible and advising them of other treatment options. The information supplied by the user on screen 1802 may subsequently be used to determine nearby pharmacies in later steps. The system may present the user with screen 1803, where the user can select any symptoms that the user is experiencing. If the system determines that the user is experiencing symptoms consistent with remote treatment (for example, mild or moderate symptoms of Covid-19), then the system may then display screens 1804 through 1807 to the user to determine if the user is eligible for one or more treatments. If the user indicates that they are not experiencing systems, the system may abort the questionnaire and explain that the user is not currently eligible for treatment. If the user indicates that they are having severe symptoms, the questionnaire may abort and advise the user to seek immediate medical attention.

In some embodiments, certain screens may be skipped based on the responses at screen 1804. For example, if the user indicates that are not taking any medications, then screen 1807 may be skipped because there is no need to inquire about medications if it has already been ascertained that the user is not taking any medications. At any point, the system may abort the questionnaire if the user's responses indicate that the user is not eligible for treatment. If the user is eligible, the user may be prompted to select a pharmacy at screen 1808. In some embodiments, the screen 1808 may be prefilled with pharmacies that are near the address entered by the patient at screen 1802, or the patient may input a zip code, street address, or the like to locate nearby pharmacies. In some cases, before selecting a pharmacy or after selecting a pharmacy, or at some other point, the user may be prompted to consult with a prescribing partner such as a physician or pharmacist. Once the required information is collected and the order is approved by a prescribing partner, the system may display to the user a screen 1809 indicating that the order has been placed. In some embodiments, the system may, instead of sending an order to a user's local pharmacy, send the order to a mail-order pharmacy or the like. In some embodiments, the system may be further configured to display an order status, shipment status, shipment tracking number, or the like.

Professionally-Administered Treatment

Unlike self-administered treatments such as oral medications, some treatments must be professionally administered. Monoclonal antibodies, for example, may be used for the treatment of Covid-19. Monoclonal antibodies are delivered as an infusion and must be professionally administered at a treatment location such as a hospital or clinic. Thus, even if a patient takes an at-home test, the patient will still have to travel to obtain treatment. Even in such cases, however, it may be advantageous for the patient to obtain a drug order for monoclonal antibodies through a remote testing platform as the patient can avoid having to visit a medical facility to determine whether monoclonal antibodies are an appropriate treatment and to obtain an order for the monoclonal antibodies, potentially saving time and allowing for earlier treatment.

Figures 19, 20:
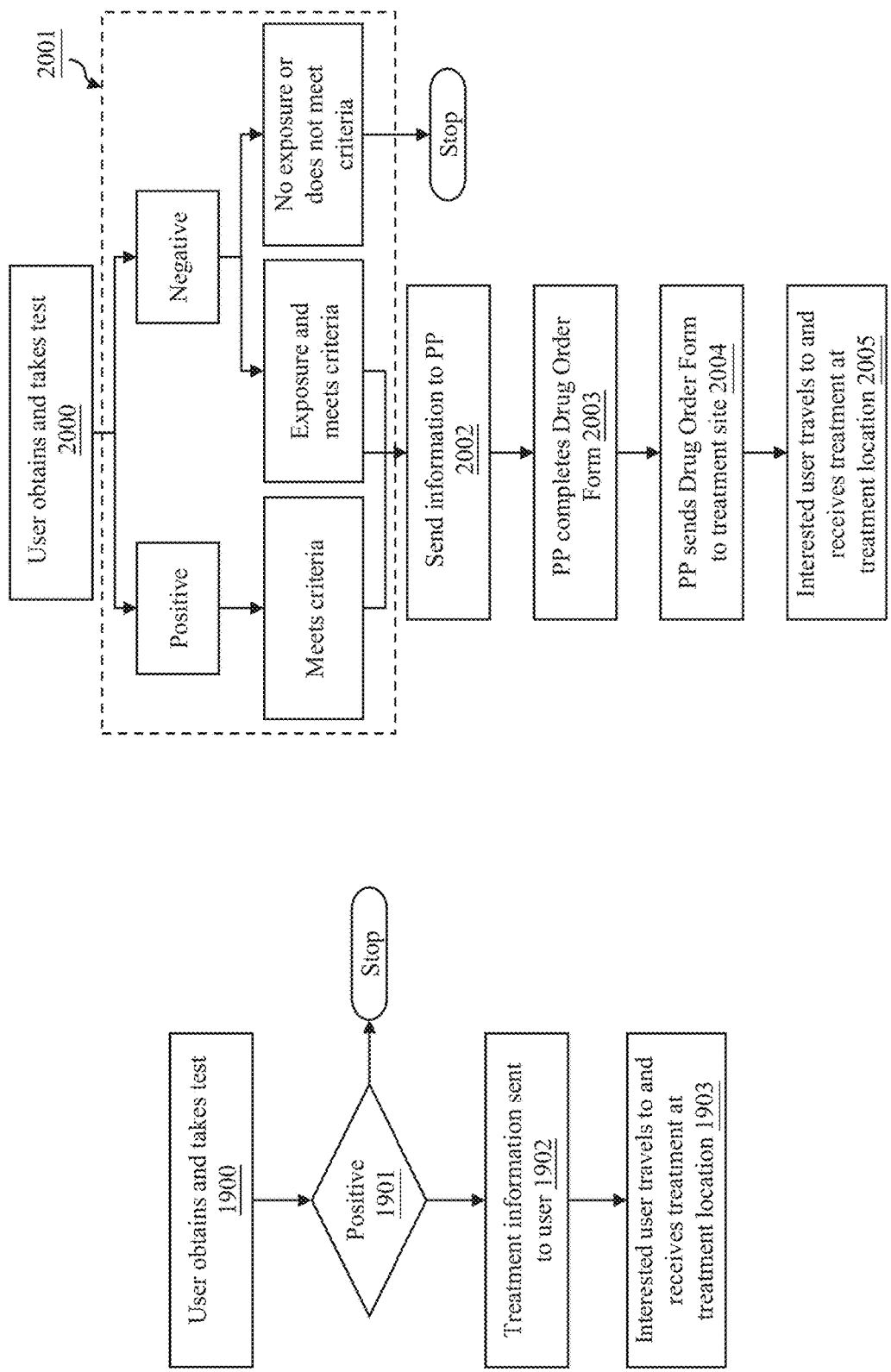
FIG. 19 shows an illustration of professionally-administered treatment according to some embodiments.
FIG. 20 shows an illustration of professionally-administered treatment according to some embodiments.

FIG. 19 shows an illustration of professionally-administered treatment according to some embodiments. At 1900, a user obtains and takes a diagnostic test, such as, for example, a Covid-19 test. At 1901, the result is negative, the user is finished with the process and no further action is taken. If, however, at 1901, the test result is positive, a testing platform may send the user information about professionally-administered treatment (e.g., monoclonal antibody treatment). The information provided to the patient may include treatment sites, information about eligibility, and so forth. At 1903, an interested user travels to a treatment location and receives treatment if a provider determines that treatment is appropriate. Under the process depicted in FIG. 19, determining whether the user is eligible for treatment and placing orders for treatment are outside the scope of the remote testing and treatment process. Instead, a user is provided with information that helps them locate treatment sites and providers who can order treatment.

FIG. 20 shows an illustration of professionally-administered treatment according to some embodiments. At 2000, a user obtains and takes a diagnostic test such as, for example, a Covid-19 test. At 2001, the patient may test positive and meet the criteria for treatment, may test negative and have been exposed and meet the criteria for treatment, or may test negative and either not have a known exposure, not meet the treatment criteria, or both. If a user meets the treatment criteria and either tests positive or tests negative but has a known exposure, the patient's personal information, test results, and other information such as, for example, any questionnaires or the like that the user completed may, at 2002, be sent to a prescription partner (PP) for review. The prescription partner, upon determining that treatment is appropriate for the user, may at 2003 complete a Drug Order Form (for example, for monoclonal antibody treatment) and then, at 2004, send the Drug Order Form to a treatment site. At 2005, an interested user travels to the treatment site and receives treatment.

Prescription Medicine Order Fulfillment and Delivery Coordination

Figure 21:
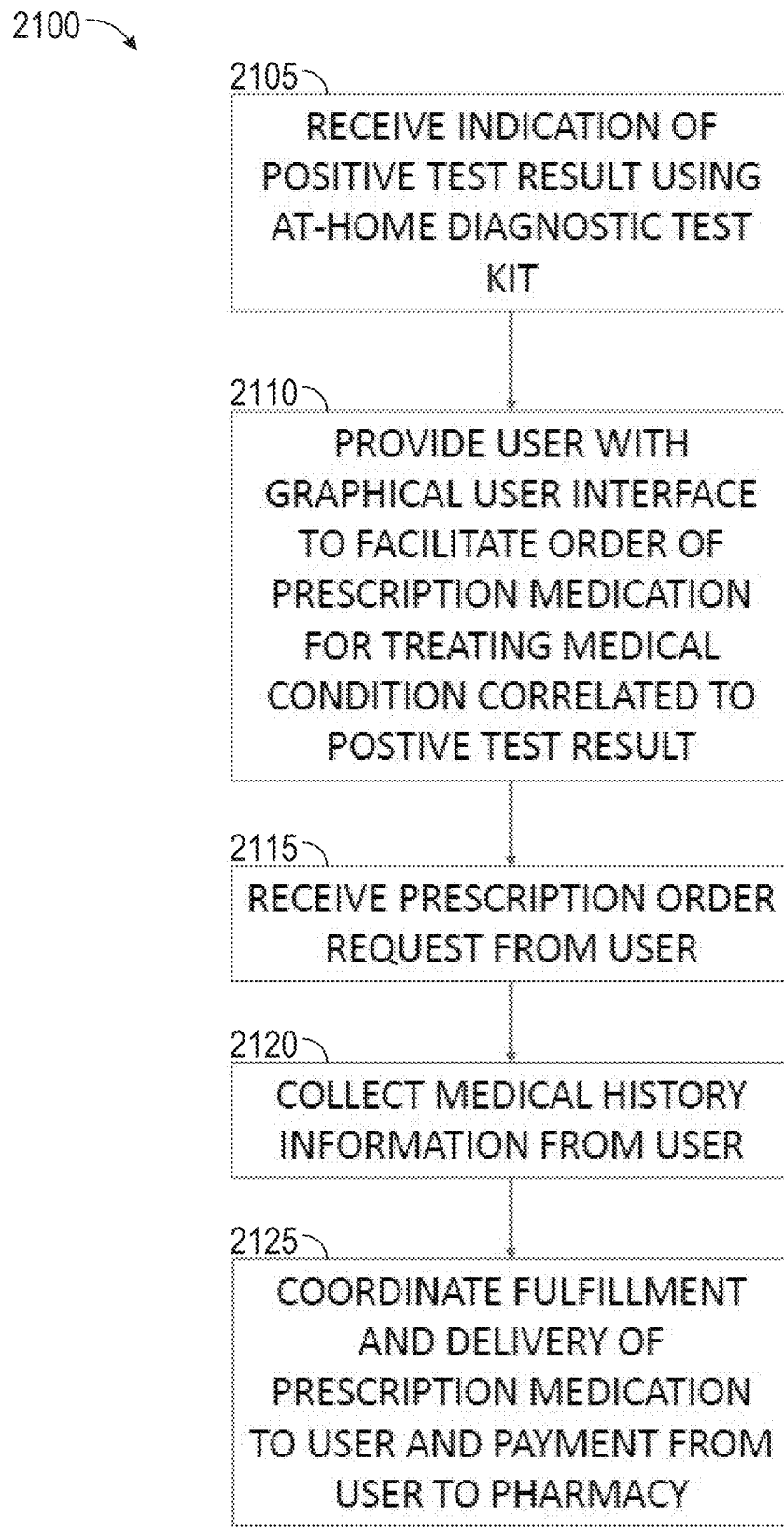
FIG. 21 illustrates an example flowchart of a method for facilitating ordering, fulfillment, and or delivery of prescription medication following a test result indicative of a medical condition that can be treated with prescription medication according to some embodiments described herein.

FIG. 21 illustrates an example flowchart of a method 2100 for facilitating ordering, fulfillment, and or delivery of prescription medication following a test result indicative of a medical condition that can be treated with prescription medication according to some embodiments described herein. At Block 2105, the remote health testing and diagnostic platform (e.g., platform 4202 shown in FIG. 42) receives an indication of a test result using an at-home diagnostic test kit (e.g., medical diagnostic test kits 115 in medical diagnostic test kit container 100) that the user has a particular medical condition (e.g., UTI, STI, influenza, COVID-19). In some embodiments, the indication of the test result may correspond to a test result as interpreted and submitted by the user and/or a proctor.

Figure 23A:
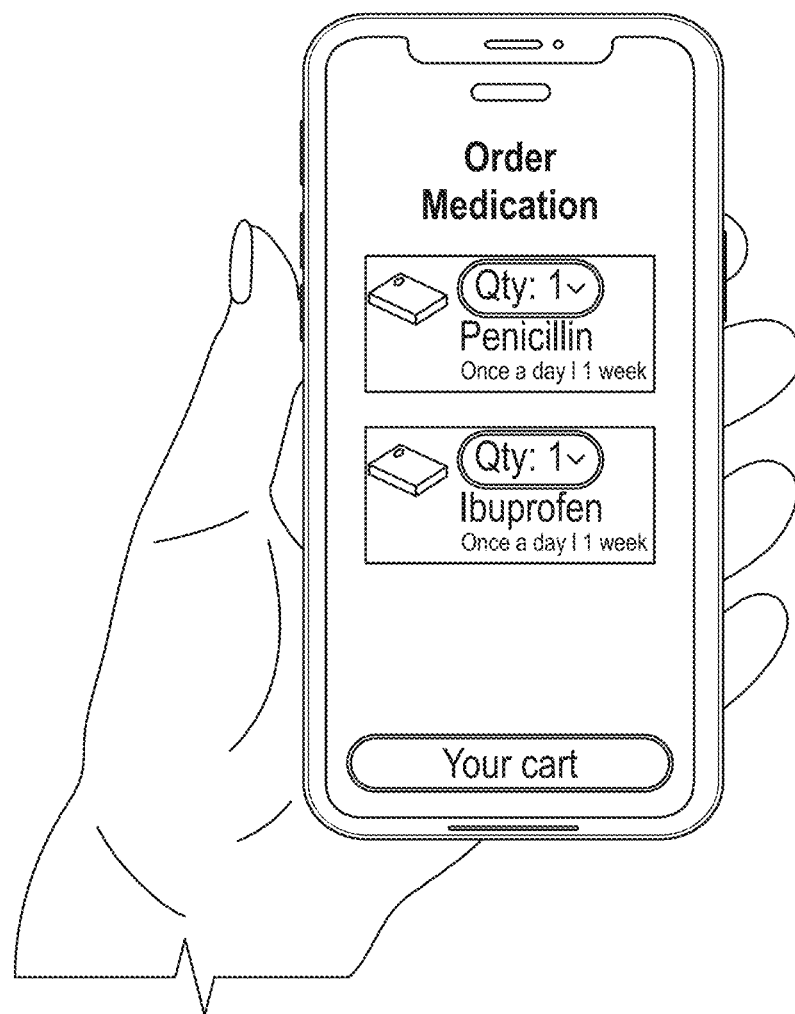
FIGS. 23A and 23B illustrate examples of screen displays and graphical user interfaces that may be displayed to a user on a user device, such as a mobile phone, to facilitate ordering of prescription medication and tracking of delivery of the prescription medication according to some embodiments described herein.

At Block 2110, the user is provided with a graphical user interface on a display screen of a user device (e.g., smart phone, laptop, tablet, smartwatch) that allows the user to initiate ordering of a prescription medication for treating the medical condition correlated to the test result obtained using the at-home diagnostic test kit 115. For example, the graphical user interface may include user-selectable graphics or text links (e.g., buttons) to facilitate ordering, such as shown in FIG. 23A.

At Block 2115, a prescription order request is received from a user (e.g., via input data received from the user-selectable graphics or text links (e.g., buttons) of the graphical user interface on the user device (e.g., smartphone or tablet)). At Block 2120, medical history information may be collected from the user to facilitate screening to be performed by a pharmacy provider or prescription medication fulfillment center.

At Block 2120, the remote health testing and diagnostic platform may coordinate fulfillment and delivery of requested prescription medication to the user and may coordinate payment from the user to the pharmacy or other prescription medication provider.

Figure 22:
FIG. 22 illustrates an example flowchart of a method for facilitating ordering, fulfillment, and or delivery of prescription medication, with steps broken down by the entity performing the steps according to some embodiments described herein.
Figure 22:
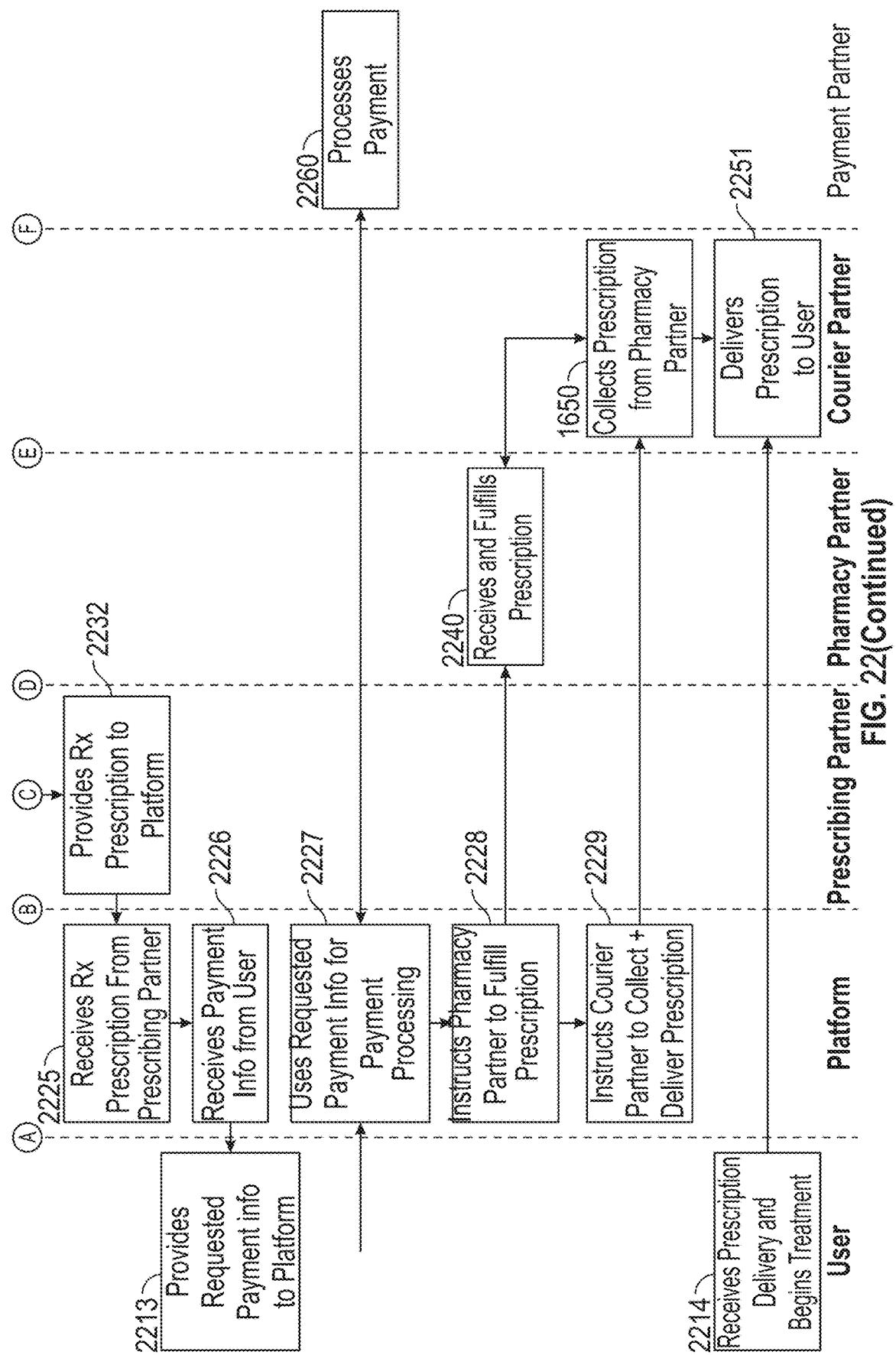

FIG. 22 illustrates an example flowchart of a method 2200 for facilitating ordering, fulfillment, and or delivery of prescription medication, with steps broken down by the entity performing the steps according to some embodiments described herein.

In some implementations, the entirety of the method 2200 can be performed in under an hour (e.g., between 30 minutes and 60 minutes, between 20 minutes and 45 minutes, between 10 minutes and 30 minutes, or overlapping ranges thereof). In some implementations, the methods disclosed herein can enable a user to receive a diagnosis and treatment for a health condition in an easy, rapid, safe, and affordable manner.

At Block 2210, a user who is interacting with the remote health testing and diagnostic platform (e.g., platform 4202 shown in FIG. 42) through a user device 110 (e.g., smartphone, tablet, laptop, etc.) for the purposes of taking a diagnostic test for a given medical condition (e.g., COVID-19, influenza A/B, UTI, strep throat, etc.) has tested positive for the given health condition (e.g., as indicated by diagnostic testing materials such as diagnostic test kits 115).

At Block 2220, the remote health testing and diagnostic platform verifies that the user has tested positive for the given medical condition. For instance, a live proctor may observe (e.g., by way of a camera on the user device 110) the diagnostic test that was taken by the user to interpret the test results, and may further verify that the test was taken correctly and therefore that the results yielded are valid. In some implementations, verification may include review of a virtual test pass or digital health pass (e.g., test pass 980) by the prescriber partner or pharmacy partner.

At Block 2221, the remote health testing platform provides the user with an opportunity to order prescription medication for treating the given medical condition (e.g., by way of a prompt presented to the user through a graphical user interface displayed on the user device 110 or through an electronic mail notification or text message notification via a telecommunications network). An example of a graphical user interface or e-commerce portal that may be provided for the user at this juncture is depicted in FIG. 23A.

At Block 2211, the user elects to order prescription medication for treating the given medical condition and, at Block 2222, the remote health testing and diagnostic platform receives user input data indicative of the user's decision to do so.

At block 2223, the remote health testing and diagnostic platform directs the user to a prescreening test for the prescription treatment that they will receive. For instance, in some examples, at this juncture the remote health testing and diagnostic platform may present the user with one or more questions to obtain information regarding whether the user has any known allergies to medications and/or any other information that may be of pertinence or relevance in the prescription fulfillment process, such as described in connection with FIG. 3E.

At Block 2212, the user completes the prescreening process (e.g., finishes submitting answers to questions posed by the remote health testing platform). At Block 2224, the remote health testing and diagnostic platform sends data including (i) data indicating the user's test results and (ii) data indicating the results of the user's prescreening to a prescriber partner. For example, the data indicating the user's test results may include images of the user's diagnostic testing materials, information supplied by the proctor, or a combination thereof. In some examples, the remote health testing and diagnostic platform also sends additional information about the user (e.g., name, date of birth, location, medical history, etc.) to the prescriber partner at this juncture. The data may include a digital health pass or test completion pass (e.g., test pass 980 described above)

At Block 2230, the prescriber partner receives and reviews the data associated with the user as sent by the remote health testing and diagnostic platform. At Block 2231, a licensed healthcare professional associated with the prescriber partner may write a prescription for treating the user's condition based on a review of the data sent by the remote health testing platform. For instance, if the licensed healthcare professional determines that the data provided by the remote health testing and diagnostic platform indicates that the user has the flu, then the licensed healthcare professional may write the user a prescription for Tamiflu. Similarly, a determination that the user has strep throat may lead the licensed healthcare professional to write the user a prescription for Amoxicillin, and a determination that the user has a UTI may lead the licensed healthcare professional to write the user a prescription for Cipro. In some examples, the licensed healthcare professional may write prescriptions for different medications based on any of a variety of factors including the user's allergies, possible interactions with other medications the user is taking, the availability of certain medications, and the like.

At Block 2232, the prescriber partner provides the prescription to the remote health testing and diagnostic platform, which in turn receives the prescription from the prescriber partner at Block 2225. In some implementations, the user may be connected with or given the option to connect with a licensed healthcare professional or other medical professional (e.g., via a remote telehealth appointment) at one or more points in the method 2200 as described above to receive guidance, medical advice, and the like.

At Block 2226, the remote health testing and diagnostic platform requests payment information from the user. At Block 2213, the user provides the requested payment information to the remote health testing and diagnostic platform. In some implementations, the payment information provided by the user at Block 2213 may include information regarding the user's credit or debit card, payment preferences, insurance information, and the like.

At Block 2227, the remote health testing and diagnostic platform uses the payment information received from the user for payment processing. In some implementations, one or more of the operations of Block 2227 are performed in coordination with a payment partner that processes payment for the fulfilment of the user's prescription at Block 2260.

In some embodiments, some or all of steps of Blocks 2213, 2226, 2227, and 2260 may be performed at different points in time and/or in a different order.

At Block 2228, the remote health testing and diagnostic platform instructs a pharmacy partner (e.g., Walgreens, CVS, Target, etc.) to fulfill the prescription for treating the user's condition. At Block 2229, the remote health testing and diagnostic platform instructs a courier partner (e.g., Uber) to collect the user's prescription medication as fulfilled by the pharmacy partner and deliver said prescription directly to the user. The courier partner may be affiliated with the pharmacy partner or may be unaffiliated with the pharmacy partner.

Figure 23B:
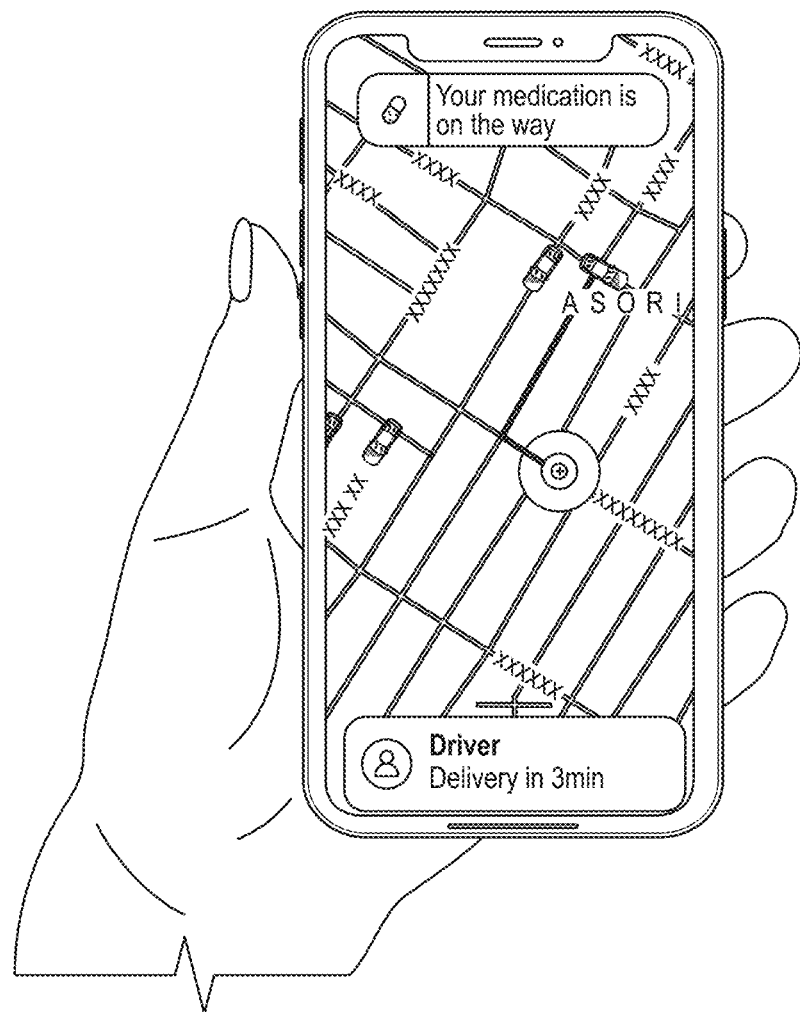

At Block 2240, the pharmacy partner fulfills the prescription for treating the user's condition. At Block 2250, the courier partner collects the prescription as fulfilled by the pharmacy partner. At Block 2251, the courier partner delivers the prescription directly to the user and, at Block 2214, the user receives the delivered prescription and begins treating their medical condition. In some implementations, the user may be provided with information regarding the status of the delivery, expected time of arrival, and/or the current location of the courier through an interface similar to that which is depicted in FIG. 23B. In some implementations, users may have the option to have test kit orders and/or prescription drug orders delivered to them via a shipping service or a courier service for rapid same day delivery.

FIGS. 23A and 23B illustrate examples of screen displays and graphical user interfaces that may be displayed to a user on a portable computing device (e.g., smartphone or tablet) to facilitate ordering of prescription medication and tracking of delivery of the prescription medication according to some embodiments described herein.

In some implementations, one or more of the exchanges between the user and the remote health testing and diagnostic platform as described above with reference to FIGS. 22, 23A and 23B may be made through and/or facilitated by an inline frame or "iFrame" HTML element of a web site or web application. In at least some of these implementations, the website or web application may be hosted by an entity other than that which maintains the remote health testing and diagnostic platform, such as a pharmacy, courier, or e-commerce business. Such an iFrame may effectively enable a website, web application, or components thereof that are hosted by the entity that maintains the testing platform to be embedded in the website or web application that is hosted by this other entity. In this way, users of the website or web application hosted by another entity, e.g., a pharmacy or e-commerce business, can quickly and seamlessly connect with the testing platform to order test kits, among other things. In some cases, test kit orders and/or prescription drug orders may be fulfilled at least in part by the other entity. For instance, if the other entity is a pharmacy, then test kit orders and/or prescription drug orders may be made available to users for pickup at their nearest pharmacy branch. Similarly, if the other entity is an e-commerce business, then test kit orders and/or prescription drug orders may be delivered to users by leveraging the business's existing supply chain and logistics infrastructure.

As an example, the website for "Duncan's Pharmacy" may include an iFrame element that enables users of the website to interface with the entity that maintains the testing platform without having to manually navigate away from and/or back to the Duncan's Pharmacy website.

Federated Testing Using a Health Testing and Diagnostics Platform

As more businesses and services begin to employ rapid testing measures (e.g., rapid COVID-19 testing measures) to ensure the health and safety of their patrons, it is becoming increasingly beneficial to provide such patrons with testing experiences that are easy to navigate and more naturally woven into the registration/reservation processes associated with such businesses and services. However, most businesses and services do not have the means necessary to distribute health testing and diagnostic kits and oversee the testing process in accordance with regulations. As such, many businesses and services may stand to benefit from leveraging the services of a dedicated health testing and diagnostic platform for providing such rapid testing measures.

While using a dedicated health testing and diagnostic platform for providing such rapid testing may ensure that health and diagnostic tests are properly distributed to and conducted by patrons, tasking patrons with using the services and testing platform of another business entity and reporting their test results back to the corresponding business or service may place undue burden on patrons and render testing measures unreliable. Thus, it may be desirable to provide a method and mechanism for integrating the services provided by the health testing and diagnostic platform into, for example, the registration/reservation processes associated with such businesses and services. This may provide a relatively simple and seamless process for patrons and facilitate and improve public health and safety.

As described herein, federated testing techniques are leveraged to provide for more seamless integration between an application or website that is associated with a business or service (the partner platform) and the services of a dedicated testing platform. As used herein, federated testing refers to integration and linking of the services of a dedicated testing platform with a business or service which is referred to herein as a partner. As an illustrative, yet non-limiting example, a business that organizes and holds events (the partner) may utilize the services of a dedicated testing platform to provide rapid testing of patrons purchasing tickets for an event. During ticket purchase, for example, on a website or application provided by the partner, the user may be automatically directed to the testing platform to perform a rapid test. The testing platform may proctor the rapid test and determine and store the result. The user may then be automatically redirected back to the website or application provided by the partner to complete the transaction. The website or application provided by the partner can retrieve the test results from the testing platform.

By leveraging such techniques, users may be able to easily interface with such a dedicated testing platform through the application or website of a given business or service (the partner) and are relieved of the burden of having to report their test results back to the given business or service. Furthermore, in some implementations, such techniques may also provide for testing and/or reporting with enhanced user security and/or privacy as will be described in more detail below.

In some examples, the secure delegated access or federated testing techniques described herein may function in a manner similar to those corresponding to the OAuth (e.g., OAuth 1.0, OAuth 2.0, etc.) or OpenID authorization standards. However, unlike such standards, which often involve the exchange of an access token for user account information (e.g., username, password, name, date of birth, etc.) via an application programming interface (API), the secure delegated access or federated testing techniques that are described herein can involve the exchange of an access token for test result information (e.g., an indication of whether user tested positive or negative for COVID-19, the date on which test was conducted, etc.) via an API. Moreover, in some embodiments, the dedicated testing platform may be completely naive to any user account information (e.g., username, password, name, date of birth, etc.), and may instead store test results in association with an arbitrary identifier that is generated by the partner application.

Figure 24A:
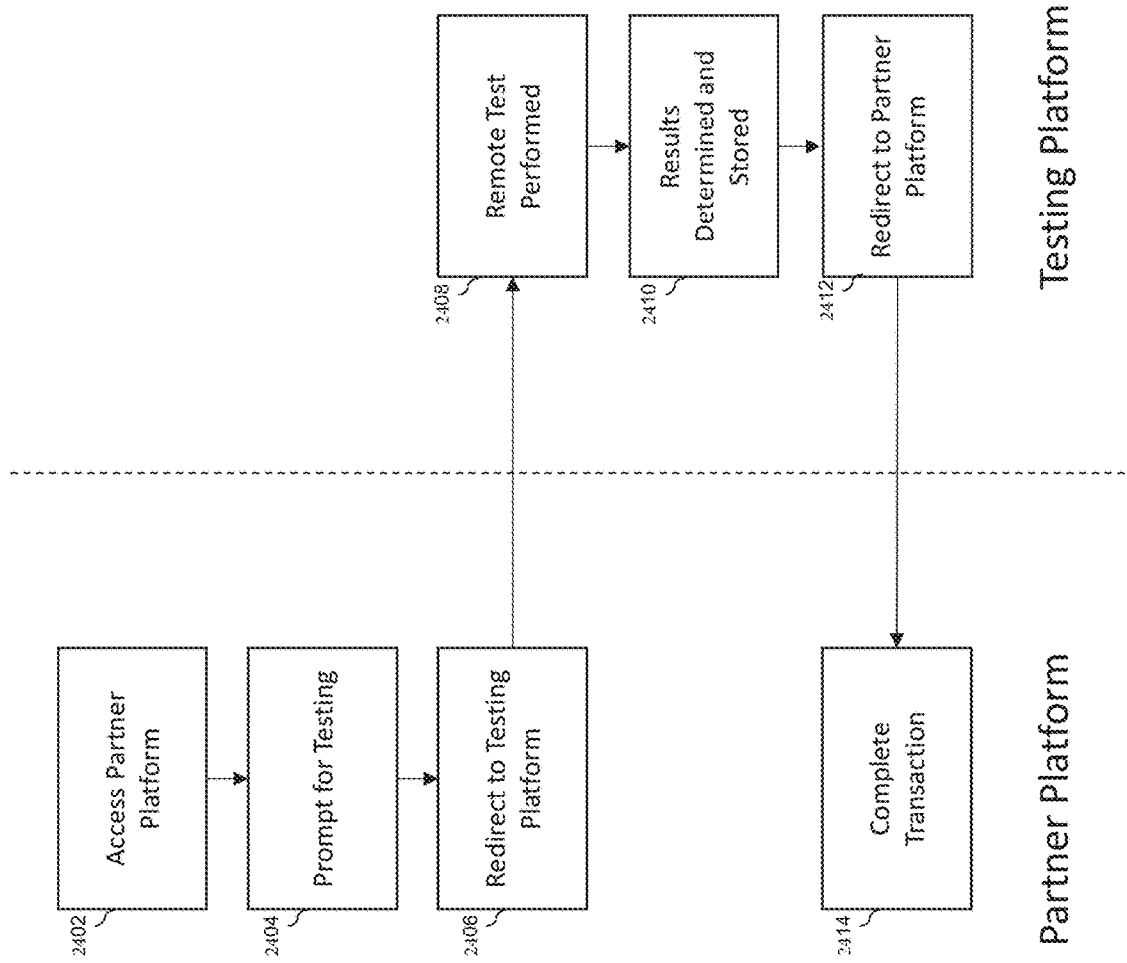
FIG. 24A is a flowchart illustrating an example method for federated testing using a health testing and diagnostics platform according to some embodiments described herein.

FIG. 24A is a flowchart illustrating an example method for federated testing using a health testing and diagnostics platform according to some embodiments described herein. The method allows for relatively seamless integration of the services provided by a dedicated health testing and diagnostic platform (referred to as the testing platform) into a business or other service (referred to as the partner platform). In general, the partner platform does not include the necessary infrastructure for providing rapid testing. Accordingly, the partner platform can be integrated with and leverage the services of the testing platform in a manner that is simple and convenient for users and that improves health and safety.

At 2402, a user accesses a partner platform. The partner platform may be a website or application provided by the partner. In some embodiments, the user accesses the partner platform via a user device. The user device may comprise, for example, a personal computer, a cellular phone, a smartphone, a laptop, a tablet computer, an e-reader device, an audio player, or another device capable of connecting to and communicating over a network, whether wired or wireless. In some embodiments, the user may access the partner platform from a remote location, such as the user's home. In other embodiments, the user may access the partner platform in person. For example, the partner may comprise a hotel or other event, and the user may access the partner platform when arriving at the hotel or event.

At 2402, the user may initiate a registration or other transaction via the partner platform. The partner platform may, if desired, gather relevant information about the user. For example, the partner platform may prompt the user to create a username and password associated with the partner platform and may collect other relevant user information as well, such as the user's name, address, date of birth, etc.). Such user information can be stored by the partner platform for future use.

If the registration or other transaction initiated by the user via the partner platform at 102 is one for which the partner wishes to ensure that the user has completed a rapid test (or some other type of test) prior to completing the transaction, at 2404, the user may be prompted to complete a rapid test. For example, if the partner platform comprises an application selling tickets for events, the partner may wish to ensure that all those that purchase tickets and attend the events have completed a rapid test prior to attending the event. Accordingly, at 2404, the user can be prompted, within the partner platform, to complete a rapid test. In some instances, completion of the rapid test may be necessary in order to continue with the registration or other transaction initiated by the user. At 2404, the user may be notified that such testing is required and given the option to proceed with the rapid test.

In some embodiments, performing the rapid test may require the use of a test kit, which includes various materials associated with the test. In such instances, access to the test kit may be provided by the partner or through the partner platform. For example, if the user is in person with the partner, the partner may immediately provide the user with the test kit. This may be the case, for example, at a hotel. At check in, the hotel can provide the user with the test kit and allow the user to take the rapid test before completing the check in process. If the user is remote from the partner, the partner platform may include a mechanism by which the user can request a test kit. The kit may be provided to the user through the mail, for example. In some embodiments, test kits may be commercially available, such that the user may purchase the test kit from a third party. In some examples, test kits may be obtained from one or more entities associated with the testing platform.

At 2406, the partner platform can redirect the user to the testing platform. At this stage, the user may be directly and seamlessly linked to the testing platform such that the testing platform can administer and evaluate the results of the test. In some embodiments, when the user is redirected to the testing platform, certain information may also be sent from the partner platform to the testing platform. Such information can include, for example, the type of test to be performed, a partner identifier that the testing platform can be used to identify the partner, a user identifier associated with the user, and/or a redirect link that will be used to redirect the user back to the partner platform after testing is complete. In some embodiments, the user identifier can identify the user in a manner such that the user's identity is only known to the partner platform. This can increase the user's privacy and security in using the testing platform.

At 2408, the test can be administered by the testing platform. The test may be completed remotely, such that the user does not need to visit a healthcare professional in person to take the test. In some embodiments, the test can be supervised by a proctor associated with the testing platform.

The proctor can ensure that the test is completed correctly and analyze the results of the test. At 2410, the results of the test are determined (for example, by the proctor) and stored for future use. In some embodiments, the results are stored in a database associated with the testing platform and associated with the user identifier provided by the partner platform. In this way, the testing platform can be naïve to the particular users taking the test and may only be aware of and store the test results in conjunction with the user identifier that can only be used by the partner platform to associate a particular user with his or her identity. This may provide several benefits to the user. For example, some users may be hesitant to share their medical results with the testing platform for fear that the testing platform may share those results with others. However, where the testing platform does not even know the true identity of the user, this concern can be greatly alleviated. Additionally, such a system may protect the user in the event of a security breach. Security breaches are increasingly common in which hackers gain access to user data that would otherwise be private. If test results are only stored in the testing platform in a manner that cannot be directly linked to a user's identity, the risk associated with such security breaches can be minimized.

In some embodiments, the testing platform may provide the user with the option to provide his or her true identity. In such cases, the user's test results can be stored in a manner that is associated with the user's true identity. In some instances, this may also be beneficial to the user. For example, if the user has recently completed a rapid test for use by a first partner platform and is now using a second partner platform that also requires the same test, the testing platform may be able to provide the results of the first test to the second partner platform without requiring the user to retake the test. Furthermore, in some embodiments, the testing platform may explicitly ask the user for permission to share some or all of the test results back with the partner at 2408 or 2410. For example, at such a juncture, the testing platform may prompt the user for permission to share some or all of the test results back with the partner, as identified using a partner identifier supplied to the testing platform by the partner platform at 2406. In some examples, the user may have completed a test using the test platform prior to initially accessing the partner platform at 2402. In these examples, the testing platform may not administer a test at 2408-2410, but may instead explicitly ask the user for permission to share some or all of the previously-obtained test results back with the partner at 108 or 110.

FIGS. 26-31, for example, which are described in more detail below, outline an example of taking a rapid and remote test using the testing platform.

At 2412, upon completion of the test, the user can be redirected back to the partner platform to continue with the original transaction, at 2414, provided by the partner (e.g., using a redirect link supplied to the testing platform by the partner platform at 2406). As described, the method of FIG. 24A, provides a mechanism for integrating the services provided by the partner platform with the services provided by the testing platform. The user is seamlessly guided between the two such that the burden placed on the user is greatly reduced. In some embodiments, such as one or more of those described in further detail below with reference to FIG. 25, when the user is redirected to the partner platform at 2412, certain information may also be sent from the testing platform to the partner platform. Such information can include, for example, an access token generated by the testing platform and stored in association with the user's test results, the user identifier (e.g., as supplied by the partner platform to the testing platform at 2406), or a combination thereof. In some embodiments, one or both of such a user identifier and access token may be ephemeral in nature. That is, in some embodiments, the partner platform may periodically change the user identifier that is associated with a given user, the testing platform may periodically change the user identifier that is associated with a given user's test results, or a combination thereof.

Figure 24B:
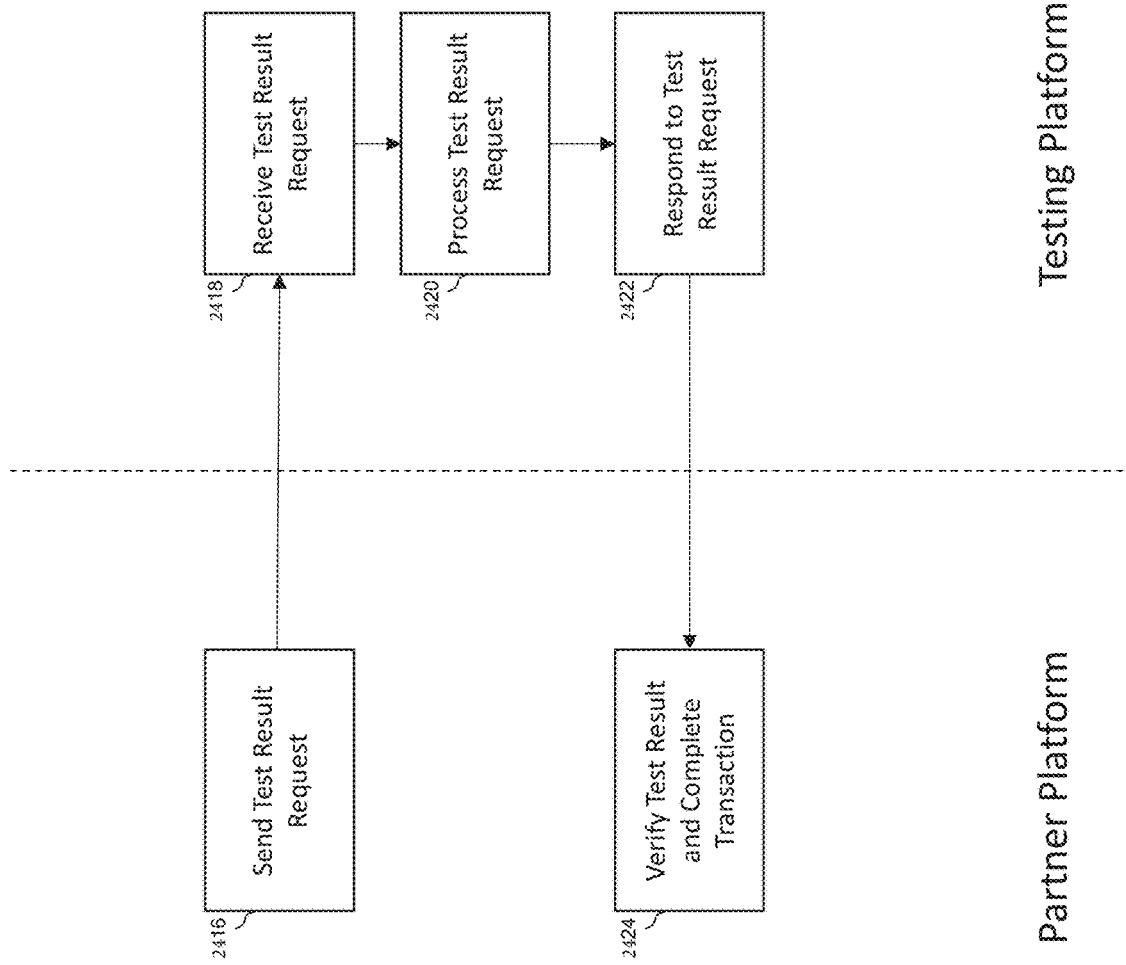
FIG. 24B is a flowchart illustrating an example method for results retrieval according to some embodiments described herein.

FIG. 24B is a flowchart illustrating an example method for results retrieval according to some embodiments described herein. In some instances, the method of FIG. 24B can be a continuation of the method of FIG. 24A. At 2416, the partner platform sends a test result request to the testing platform. The test result request can include a user identifier that, within the partner platform, is associated with a particular user. At 2416, the partner platform queries the testing platform whether results are available associated with the user identifier. In some embodiments, the test result request sent by the testing platform at 2416 may include an access token that is similar or equivalent to that of the access token described above with reference to FIG. 24A and/or the access token described in further detail below with reference to FIG. 25. At 2418, the rest result request is received by the testing platform.

At 2420, the test result request is processed by the testing platform. Processing the request may include, for example, searching a database of stored test results for the user identifier to determine whether any results exist that are associated with the user identifier. For embodiments in which the test result request sent by the testing platform at 2416 includes an access token, at 2420, the database may be queried in a similar manner using the access token in place of or in addition to the user identifier. At 2422, the testing platform responds to the test result required. For example, if test results are found that are associated with the user identifier and/or access token, such results can be communicated back to the partner platform. The results can include, for example, the result of the test (e.g., a positive or negative diagnosis) as well as other information, such as the type of test performed, information about the test kit used, the date on which the test was taken, the time at which the test was taken, etc. In some embodiments, the response to the test result request does not include the user's true identity because, as noted above, the user's true identity may not be known to the testing platform. If the testing platform does not have any information associated with the provided user identifier and/or access token, the testing platform response can communicate this to the partner platform. If the test result request sent by the testing platform at 2416 includes an access token and, as mentioned above, the access token is ephemeral in nature, the testing platform may determine whether the access token included in the test result request is still valid at 2418 or 2420, and may only retrieve test results for transmission to the partner platform in response to determining that the access token is valid. Other rules may additionally or alternatively be employed by the testing platform to selectively determine whether test results are to be provided to the partner platform, whether any pieces of data are to be selectively omitted from the test results that are provided to the partner platform, and the like.

At 2424, the response from the testing platform is received by the partner platform. The partner platform can then continue to process the user's transaction based on the results provided by the testing platform. For example, continuing the example where the partner platform is a ticket seller, in the event that the testing platform returns a result that indicates that the user has tested negative for a disease (e.g., COVID-19), the partner platform can then allow the user to purchase tickets for an event.

Figure 25:
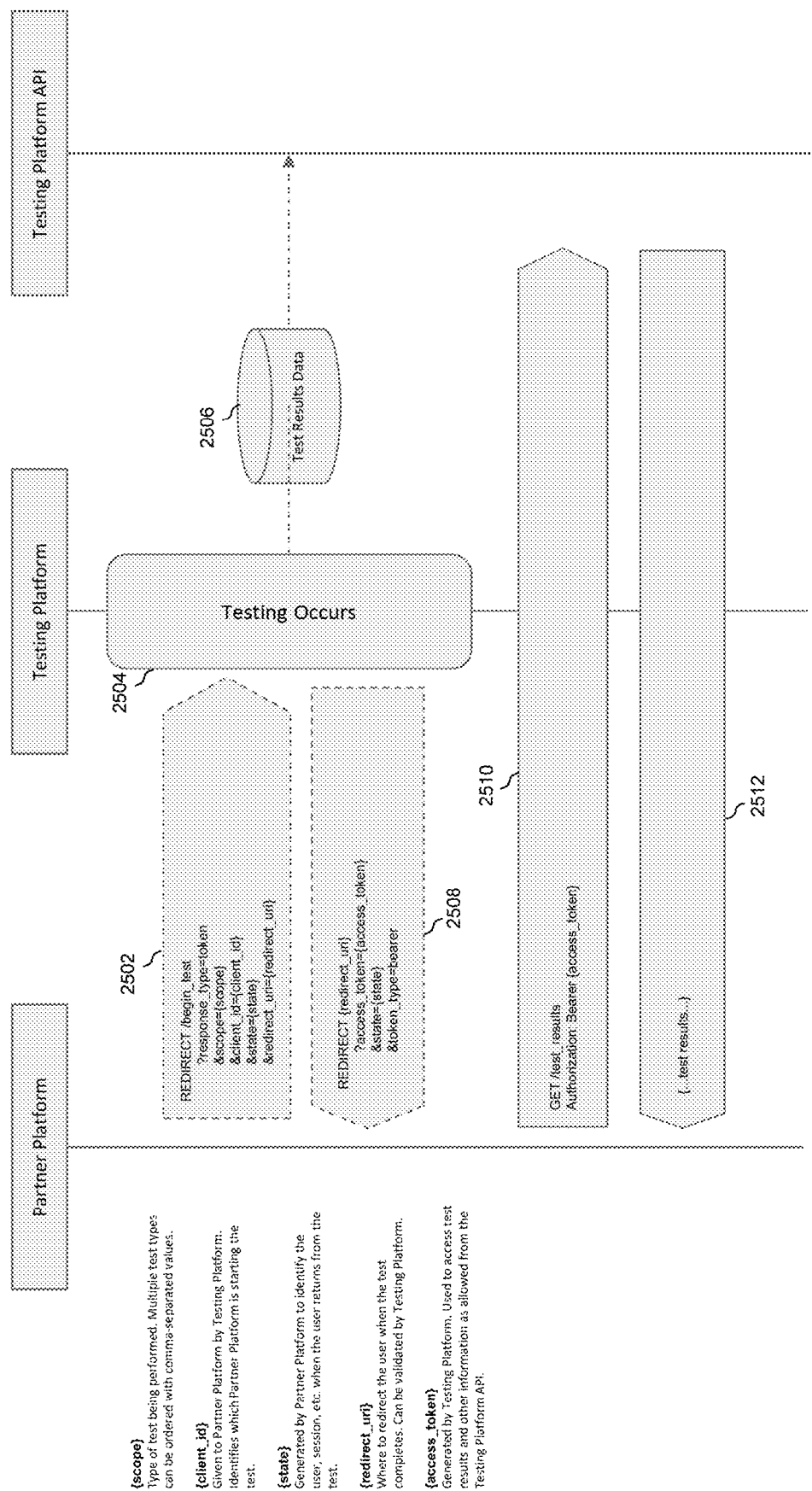
FIG. 25 is a flow diagram illustrating example steps and processes for federated testing using a health testing and diagnostics platform according to some embodiments described herein.

While FIGS. 24A and 24B have illustrated an example method for federated testing in a general manner, FIG. 25 provides a more specific example, illustrating data flow between the partner platform and the testing platform. With reference to FIG. 25, the user begins a transaction using the partner platform. At 2502, during the transaction on the partner platform, the user is redirected to the testing platform to perform a test. As shown, the user is redirected to the testing platform and various information is sent along with the user from the partner platform to the testing platform. Such information can include for example, the type of test to be performed (as indicated by the variable {scope}). The testing platform can be configured to administer a wide variety of remote tests and diagnostics, and the partner platform can provide information to the testing platform about which test is to be performed. Such information can also include information that identifies the partner platform (as indicated by the variable {client_id}). A plurality of partner platforms can each link to and leverage the services of the testing platform. When a partner platform enters into a relationship with the testing platform, the testing platform may assign the partner platform an identifier that allows the testing platform to distinguish the partner platform from other partner platforms that also use the testing platform's services. The information may also include information that is generated by the partner platform and is associated with the user's state (as indicated by the variable {state}). Such information include a user identifier, which as described above may identify the user within the partner platform but may not, in some cases, provide the user's actual identity within the testing platform. Such information can also include information about the user's session or transaction with the partner platform such that the session can be resumed after testing, once the user is returned to the partner platform. Additionally, the partner platform may provide a redirect link (as indicated by the variable {redirect_url}) which indicates where to send the user after completing the test.

At 2504, the user completes the test using the testing platform. In some embodiments, the testing platform may explicitly ask the user for permission to share some or all of the test results back with the partner at 2502 or 2504. At 2506, the test results are stored, for example, in a database associated with the testing platform. As noted previously, examples of testing using the testing platform are provided below with respect to FIGS. 26-31 and 41. At 2508, once the test is completed, the user is redirected back to the testing platform, using, for example, the redirect link provided at 2502. Along with the redirect, the testing platform may send information associated with the user's state back to the testing platform such that the user's session with the testing platform can be resumed. The testing platform may also send an access token (as indicated by the variable {access_token}) back to the testing platform. The access token can be generated by the testing platform and used to access test results.

At 2510, the partner platform can request the test results from the testing platform by, for example, providing the access token to an API associated with testing platform. The API can retrieve test results associated with the access token from the stored database and return them to the partner platform at 2512.

To further illustrate federated testing using a health testing and diagnostics platform, a more concrete example use case will now be described with the understanding that this example is provided by way of illustration and should not be construed as limiting. Many other use cases are possible. In this example, federated testing techniques can be used during hotel check in, in an effort to assure that those arriving at the hotel are free from a disease (such as COVID-19). When the user enters the hotel lobby, the user may be provided with a testing kit (e.g., COVID-19 test kit) by the concierge. In some embodiments, the user may be provided with the test kit before arriving at the hotel. For example, the user may receive the test kit through the mail. The user may then access the hotel website or application (e.g., the partner platform of FIGS. 24-25) to complete check in. In some embodiments, the user accesses the partner platform by scanning a QR code on the testing kit box. The user may sign into the partner platform (e.g., using their reservation info).

The hotel's website or application can then prompt the user to use the testing platform to take a test. The user may provide an indication of their desire to proceed to the testing platform and to take the test and, in response, the hotel website or application may redirect the user to the testing platform and send information to the testing platform. The information may include, for example, (i) data indicating the type of test being performed, (ii) data identifying the hotel, (iii) an identifier generated for the user by the hotel, (iv) data indicating the address (associated with the hotel website/app) to which the user is to be redirected following testing.

The user can then take the test using the testing platform. For example, the user may participate in a proctored session as described in more detail below. In some embodiments, the testing platform optionally explicitly asks the user for permission to share some or all of the test results back with the hotel website or application. Upon completion of the test, the testing platform stores the test results and an access token generated by the testing platform in association with the test results to a database, redirects the user to an address specified by the hotel website or application, and sends the hotel website or application information including (i) the access token and (ii) the identifier generated for the user by the hotel.

At some later point in time (which can occur nearly immediately or some time later), the hotel website or application can send a request to an API in communication with the database of the testing platform. The request can specify the access token and request test results stored in association with the access token. Upon receiving the request from the hotel website or application, the API of the testing platform can use the access token to determine whether there are any test results stored in association therewith and, if so, further determine whether the hotel website or application has permission to access said test results using the access token. In response to determining that (i) there are test results stored in association with the access token, and (ii) the hotel website or application has permission to access said test results using the access token, the API can retrieve the test results from the database, and send the retrieved test results to the hotel website or application. Finally, the hotel can take some action based on the test results (e.g., if the user tests negative—the hotel may check the user in and provide them with a room key, or if the user tests positive—the hotel may cancel the user's reservation and provide them with a refund, etc.). Although primarily described within the context of hotels (e.g., hotels, motels, bed and breakfasts, etc.) and events (e.g., sporting events, concerts, conferences, etc.), it is to be understood that one or more of the partners described herein may correspond to any of a variety of businesses and/or services including dating platforms, airlines, cruise lines, pharmacies, restaurants, rental and chartering services, and the like. Similarly, although primarily within the context of tests and test kits for COVID-19, one or more of the tests and test kits described herein may correspond to tests and test kits for any of a variety of viruses, diseases, and health conditions.

Example Remote Testing Platforms

FIGS. 26-31 provide additional detail regarding providing testing using the testing platform. The testing platform can be configured to facilitate remote health testing via remote connection of patients and medical providers. Remote medical testing provides various benefits over in-person visits to medical professionals. For example, remote medical testing provides both safety and convenience to patients and medical providers. Additionally, because of advancements in medical and logistics technology, especially as described herein, remote testing can now be extremely fast. In some cases, diagnostic tests can be administered and read within seconds. Other tests may require a cure time before being read or may require delivery to a laboratory to receive results, but results can still be received within days in most cases.

A health testing and diagnostic platform is provided to connect medical providers (such as remotely located medical providers) with patients and to generate a unique, private testing environment. In some embodiments, the testing environment may facilitate administration of a medical test to a patient with the guidance of a proctor. In some embodiments, the proctor may comprise uncertified personnel, certified medical personnel, and/or a proctor for monitoring an algorithm such as computer software, which may administer a medical test. In some embodiments, the computer software is not administering the medical test but rather is monitoring the medical test for abnormalities or deviations or inconsistencies in the administration or performance or procedure of the medical test that is being administered by the uncertified personnel and/or certified medical personnel and/or medical personnel and/or the like. In some embodiments, the patient may be provided with step-by-step instructions for test administration by the proctor within a testing environment. The platform may display unique, dynamic testing interfaces to the patient and proctor to ensure proper testing protocols and/or accurate test result verification.

In some embodiments, the platform may provide a testing environment comprising a private communication channel (such as over the internet) between a proctor and a patient. In some embodiments, the testing environment may comprise one or more unique user interfaces that may facilitate seamless testing, submission and verification. In some embodiments, the platform may provide for automatic transmission of verified test results to users, relevant authorities, and third-parties (such as the partner platform described above).

In some embodiments, proctors may be enabled to initiate testing sessions via a virtual waiting room and interpret test results using tools provided by the one or more unique user interfaces of the platform. In some embodiments, proctors may be enabled to manage more than one test session concurrently via unique multi-session user interfaces generated by the platform, which assist with management and administration of multiple concurrent test sessions.

Figure 26:
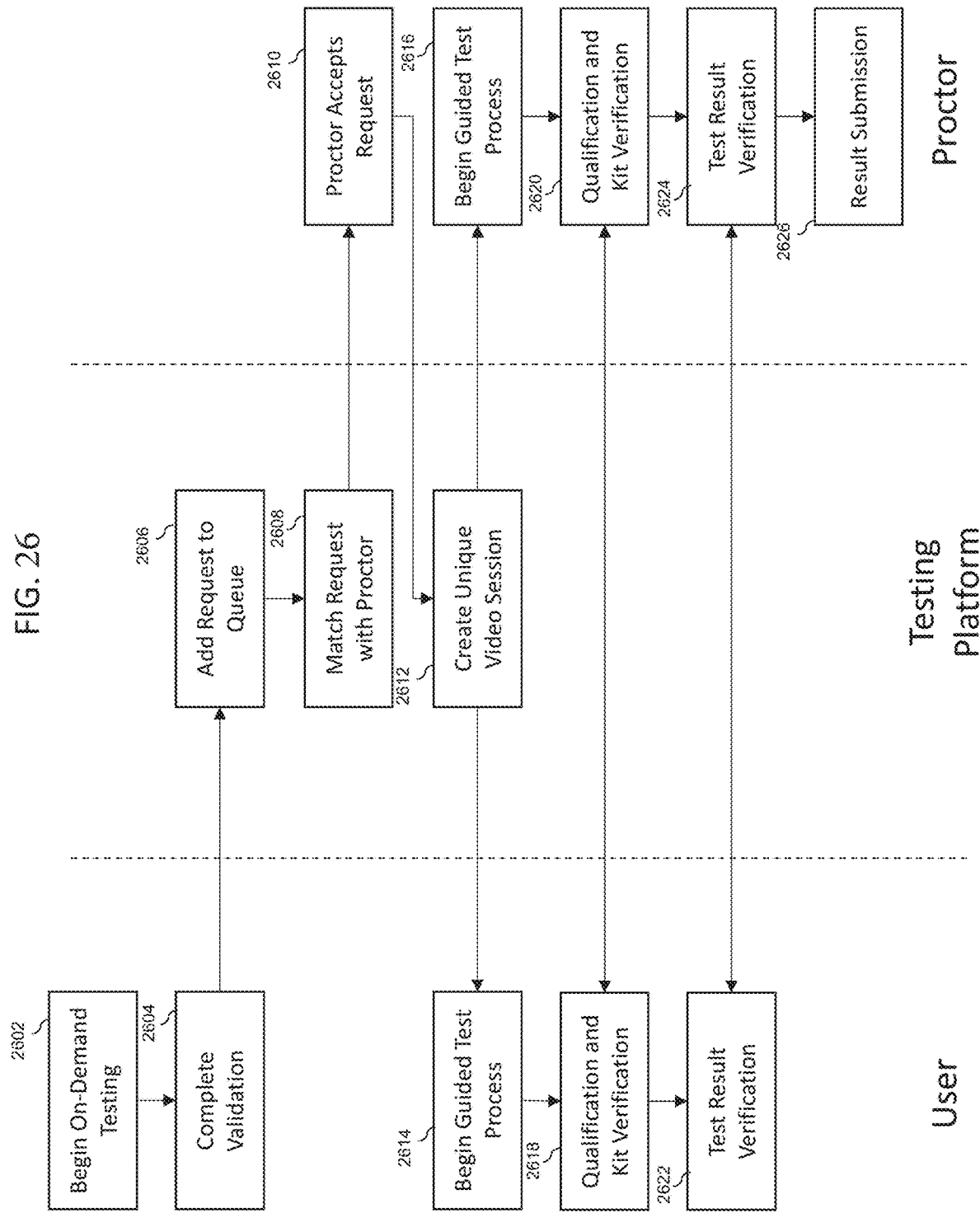
FIG. 26 illustrates an example flowchart of an on-demand testing protocol with a proctor according to some embodiments described herein.

FIG. 26 illustrates an example flowchart of an remote testing protocol according to some embodiments described herein. Such remote testing can be used, for example, at 2408 and 2410 of FIG. 24A and at 2504 of FIG. 25. In some embodiments, once a test kit has been received and activated by a patient, the patient may access the testing platform via a user device in order to initiate an on-demand testing session at 2602. Accessing the testing platform can include being redirected from a partner platform as described above. At 2604, a validation may be performed to verify that the user is ready for testing. In some embodiments, initiation of the testing session by the patient may cause the platform to place the patient in a virtual waiting room, where the patient's testing session will be queued at 2606 pending a match with an available medical provider proctor at 2608 In some embodiments, after the proctor has been matched with the patient or upon manual selection of the patient by the proctor, the proctor may review the patient information and accept the request to begin the testing session at 2610. Acceptance of the request may initiate a unique, one-way or two-way video session between the patient and the proctor at 2612 provided by the platform. In some embodiments, the video session may involve a guided test process at 2614 for the patient on a user device and at 2616 for the proctor using a proctor device, which could be a mobile device, laptop, desktop, or other computer device. As a first step in the testing session, the proctor and patient may follow provided on-screen steps to ensure that the patient is verified and qualified at 2618, 2620, as well as to verify the that the test to be used matches the test information stored in the user profile upon test activation. After verification and qualification, the proctor may guide the patient through a series of steps comprising a testing protocol in order to achieve a test result. In some embodiments, a test result may be verified by the proctor and/or patient at 2622, 2624. In some instances, test result verification involves a visual inspection of the test kit by the proctor to determine and manually submit the test result. In some embodiments, the verified test result is submitted by the proctor and stored within a test database of the platform at 2626.

Figure 27:
FIG. 27 illustrates an example pre-testing confirmation interface according to some embodiments described herein.

FIG. 27 illustrates an example pre-testing confirmation interface according to some embodiments. The pre-testing confirmation interface may be displayed to a patient who has indicated that the patient is ready to begin testing. In some embodiments, the pre-testing confirmation interface may comprise various verification questions that are designed to ensure that the patient has the time and materials necessary to being a testing session. For example, it may be required that the patient has at least 20 minutes to administer the test, as well an unopened test package received via mail or otherwise properly obtained. Within the pre-testing confirmation page, the patient may also need to verify personal information, such as their date of birth, in order to proceed to the virtual waiting room and to a testing session.

FIG. 28 illustrates an example pre-testing virtual waiting room according to some embodiments provided herein. In some embodiments, the pre-testing virtual waiting room may be displayed to a patient after completing pre-testing verification and confirmation. In the virtual waiting room, the patient may await dynamic connection with a proctor, who will oversee a testing session with the patient. In some embodiments, once a proctor has selected to begin a test with the patient or is automatically assigned to the patient, a unique activation code may be transmitted to the patient via short message service (SMS), text message, electronic mail (E-mail), voice call, or another electronic communication channel.

FIG. 29 illustrates an example unique code submission interface according to some embodiments provided herein. In some embodiments, a patient may be directed to the unique code submission interface once the patient has been matched with a proctor. In some embodiments, the match may occur after the patient enters a virtual waiting room. In some embodiments, the unique code submission interface may allow the patient to enter a unique activation code for entering a private one-way or two-way communication channel with a proctor. In some embodiments, the unique code submission may initiate testing session between the patient and the proctor.

Figure 30:
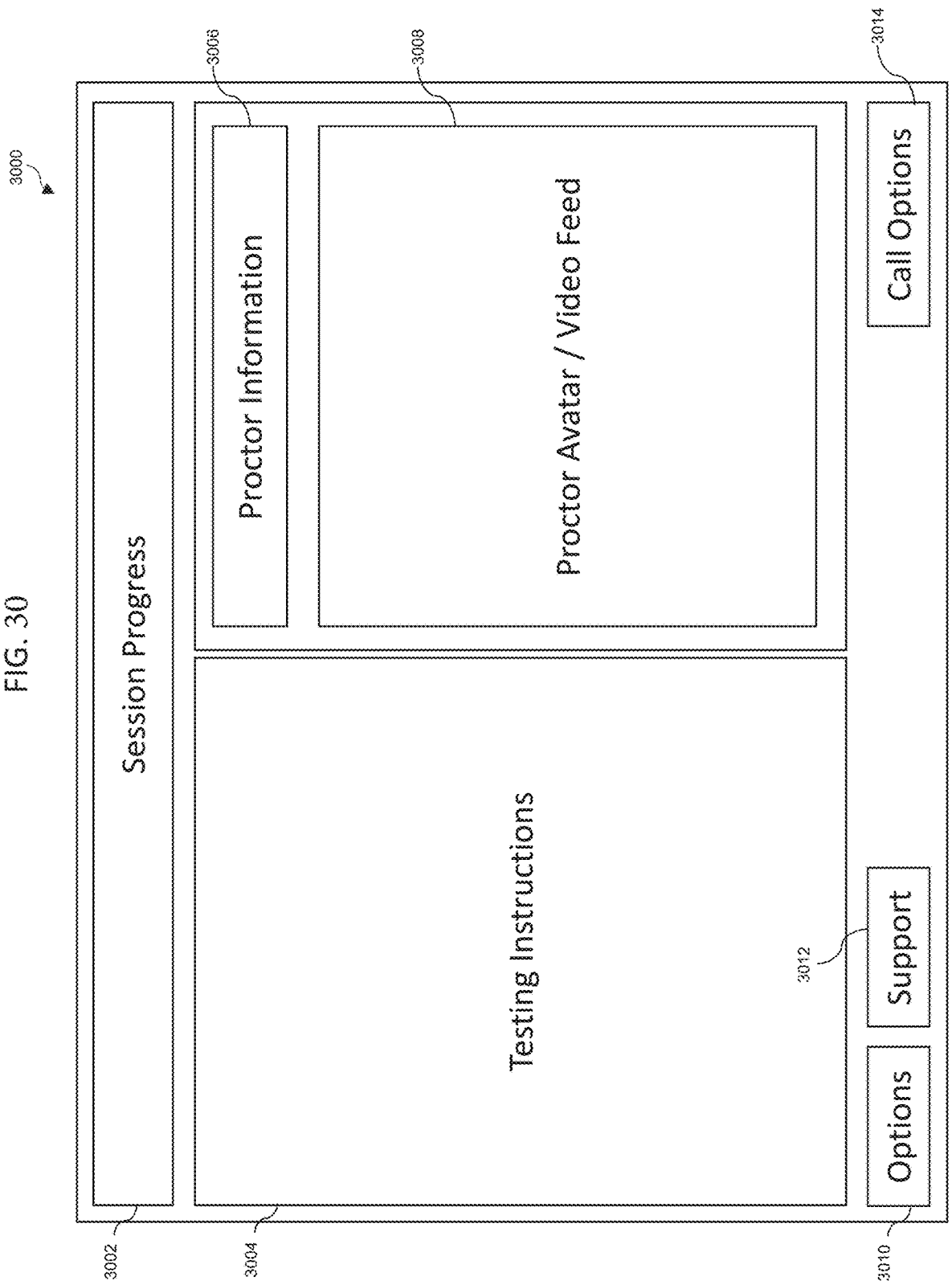
FIG. 30 illustrates an example patient testing interface according to some embodiments described herein.

FIG. 30 illustrates an example patient testing interface according to some embodiments provided herein. The example testing interface 3000 may be displayed to a patient for facilitating one or more medical tests on the patient and provides instructions and tools for self-administering the test and connecting with a proctor, who oversees and provides guidance during the test. The interface may be designed to accurately record a patient test result and to allow the patient to understand the exact step-by-step procedure that must be followed to achieve a successful test result.

In some embodiments, the example testing interface 3000 may comprise a session progress indicator 3002. The session progress indicator 3002 may provide a visual and/or audible indicator of the progress of a testing session. For example, the session progress indicator 3002 may show a step number, a timer, a timeline, or other indicator of progress. The session progress indicator 3002 may assist a patient in determining the current status of the testing session.

In some embodiments, the example testing interface 3000 may comprise testing instructions 3004. In some embodiments, the testing instructions 3004 may comprise step-by-step instructions that the patient must follow in relation to a provided at-home test kit in order to self-administer the test and achieve a valid test result. In some embodiments, the testing instructions 3004 may be read by a patient in addition to audible instructions provided by the platform or manually by a proctor. The proctor may be heard by the patient via a secure communication channel and in some embodiments, may be visible in a live proctor video feed 3008. In other embodiments, a virtual proctor avatar may be shown instead of the proctor video feed. In some embodiments, a prerecorded video may be displayed rather than a live proctor video feed.

In some embodiments, proctor information 3008 may be displayed and provide information to the patient regarding the proctor that is overseeing the testing session, including, for example, the proctor's name, certifications, and a photograph of the proctor, among others.

In some embodiments, the example testing interface 3000 may also comprise one or more options 3010, a support link 3012, and one or more call options 3014. In some embodiments, the options 3010 may comprise general platform options, including accessibility options, video options, and other miscellaneous options. In some embodiments, the support link 3012 may connect the patient to an administrator or other support personnel, in the event that such support is needed. For example, if there is an emergency with the proctor or patient, or there is an issue with testing, the support link 3012 may allow a third-party to join the testing session. The call options 3018 may, for example allow a patient to mute their device microphone or end the testing session.

Figure 31:
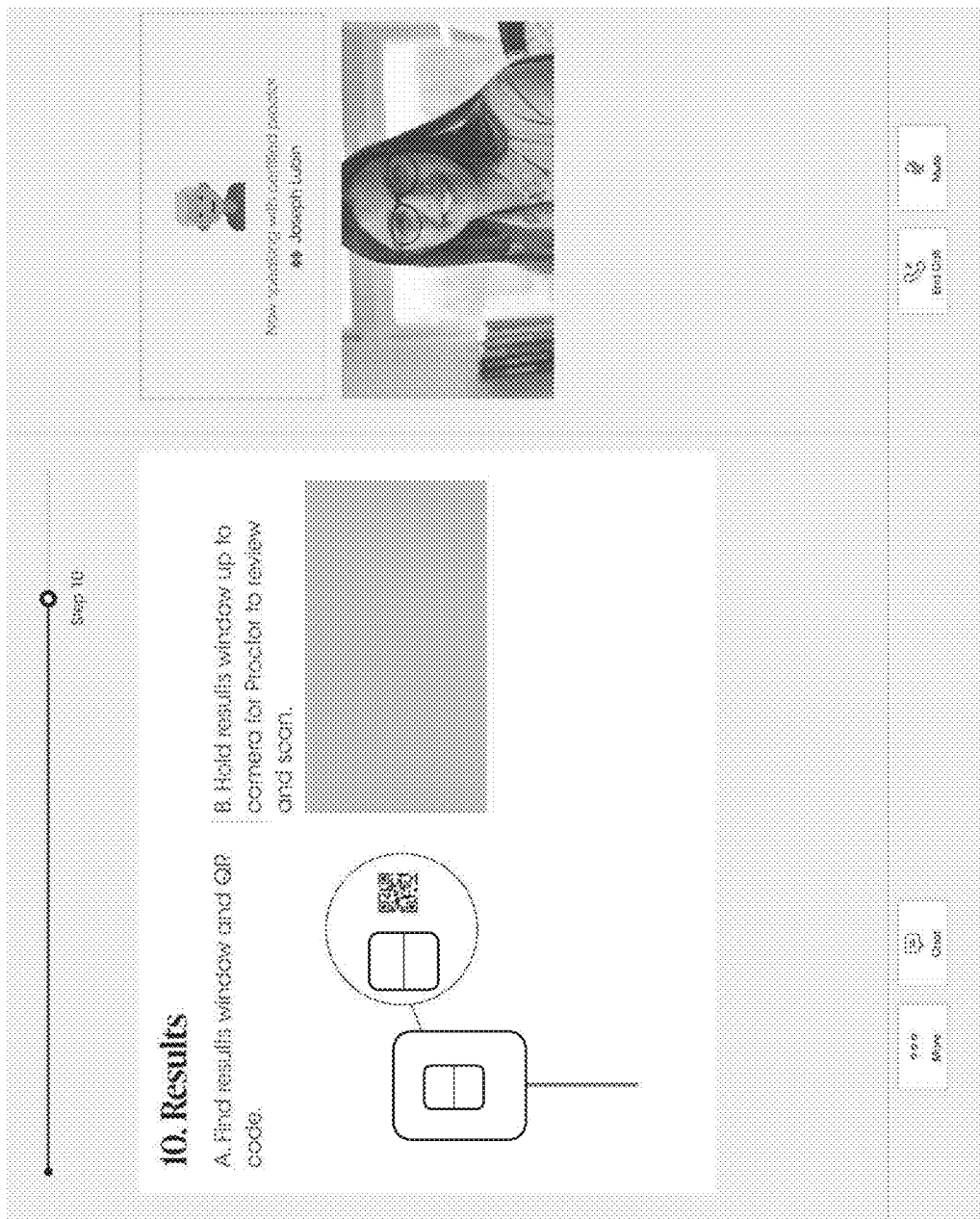
FIG. 31 illustrates an example patient testing interface according to some embodiments described herein.

FIG. 31 illustrates another example patient testing interface according to some embodiments described herein. In some embodiments, the patient testing interface may comprise directions to register a medical test using a camera on the user device. For example, some commercially available diagnostic tests comprise a QR code comprising a data matrix that has an encoded ID. In some embodiments, the platform may perform a scan through the user camera to read the data matrix. In some embodiments, the read data may be sent automatically to the test provider through, for example, an application programming interface. In some embodiments, the delivery and patient data and all other pertinent information may be retrieved from the test provider to verify that the test and patient in the testing session match with the platform records. In some embodiments, the user may be directed to display or scan the code multiple times throughout a testing session in order to verify that the same test is being used throughout an entire session. For example, scanning the code at the start of the testing session, immediately before and after critical testing steps, and/or at the end of the testing session can prevent a user from switching tests midway through the testing session. In some embodiments, the data matrix can also be read, such that a unique code is obtained, which can be compared against all previous codes read by the platform. If a duplicate code is read, the test may be discarded.

In some embodiments, the testing interface may comprise a video feed comprising an image/video of the patient or a plurality of images/videos of a plurality of patients. In some embodiments, software, such as machine learning or artificial intelligence software, or non-machine learning or artificial intelligence algorithms (for example, image segmentation analysis, pattern recognition, or the like) or otherwise, may be used to detect elements within the video feed. These elements may include, for example, a patient, a patient reference element, a test, and a test reference element. In some embodiments, the software may be configured to monitor the video feed to ensure proper test protocol and completion. For example, in some embodiments, the software may utilize image or video recognition algorithms to periodically or continuously measure one or more relative distances and/or movements of the patient reference element and the test reference element. In some embodiments, the patient reference element may comprise the patient's nostril, nose, lip, mouth, eye, ear, or any other body part. In some embodiments, the testing reference element may comprise a line or other visual indicator on the test. In some embodiments, by measuring a horizontal and/or vertical distance and/or movement between the patient reference element and the test reference element, the software may compare such values against predetermined threshold values to verify proper testing protocols are satisfied, for example, minimum/maximum distance traveled or reached, minimum/maximum number of motions and/or rotations performed. In other embodiments, machine learning and/or artificial intelligence may be used to interpret the patient video feed 1506 to verify testing procedures are completed properly.

In some embodiments, a multi-session interface may be configured to manage a scenario where a proctor is managing more than one testing sessions simultaneously. In some embodiments, the multi-session interfaces may comprise multiple views that can be displayed, each view representing a one-to-one with a patient. As such, in some embodiments, the proctor is able to interface with a single patient at a point in time, but manage more than one patient testing sessions simultaneously, and switch between those sessions seamlessly. In some embodiments, the multi-session interfaces described herein may facilitate isolated audio/video sessions between multiple patients simultaneously through use of single-channel audio, on-screen session progress indicators, and proctor prompts.

In some embodiments, the multi-session testing interfaces described herein may allow for concurrency of about 2 to about 20 patient testing sessions for a single proctor. In some embodiments, the multi-session testing interfaces may comprise a workflow timeline that identifies patient testing progress for pending testing sessions, such that a proctor can immediately understand the progress of each pending session and switch between each isolated session as needed. For example, for some disease testing, there may be a testing cure time during which the patient and proctor are waiting for the test results. During this time, the multi-session testing interface may allow a proctor to switch an active session to another patient at a different point in the testing process such that multiple sessions can be managed simultaneously. The multi-session interfaces may introduce a supply line of isolated patient video sessions such that the patient sessions are stacked efficiently and proctor availability is maximized. In some embodiments, the multi-session interfaces may comprise a management tool that allows proctors to track the concurrent session timeline and to understand the upcoming timing requirements of each isolated session and the sessions collectively.

In some embodiments, each patient testing session enables a separate audio/video channel such that patients are isolated from each other and cannot hear or see other patient testing sessions, while the proctor may activate each individual patent testing session to communicate directly with each patient. Thus, the audio/video channels for each patient are segmented into separate feeds such that individual sessions are distinctly managed separately with separate session IDs and in such a way that none of the patients can talk to each other or are even aware that multiple sessions are occurring concurrently. In some embodiments, a proctor may activate a specific patient testing session through an activation mechanism on the proctor's screen, such as by selecting a patient video feed. The activation mechanism will open the audio and/or video channel with the specific patient for which the patient testing session has been chosen. This configuration minimizes the risk of exposing sensitive medical or personal data between patients; only the proctor may communicate with each patient. Furthermore, the multi-session interfaces described and shown herein facilitate efficient session switching through visual prompts that allow a proctor to understand the point at which each testing session is currently progressed.

In some embodiments, the multi-session interfaces may comprise individual patient mute mechanisms, which may close the communication channel with an individual testing session, as well as a global mute mechanism, which may close all communication channels between the proctor and all pending testing sessions. In some embodiments, only one patient testing communication channel may be opened at a time, such that a proctor may only communicate with a single patient at a single point in time. For example, opening a communication with one patient may automatically close (e.g., mute) a communication channel with all other patients to ensure that privacy between patients is maintained.

For example, a proctor view can be separated into a main session (e.g., the upper portion of the screen) and one or more secondary sessions (e.g., shown in a lower toolbar of the screen below the main session). In some embodiments, the proctor may have an open communication channel to the main session, while the secondary sessions remain muted. In some embodiments, the proctor may be enabled to exchange the main session with one of the secondary sessions by selecting one of the secondary sessions. Selecting one of the secondary sessions may cause display of that secondary session as the main session, and relegate the previous main session to the secondary session toolbar. In some embodiments, the multi-session interfaces may comprise one or more visual cues to indicate to the proctor the status of each patient session and to alert the proctor if attention is needed for any given session. For example, in the illustrated embodiment, such visual cues include an elapsed testing time for each patient, a countdown timer, and a question indicator.

Another example multi-session testing interface may comprise a multi-window interface. In some embodiments, the multi-window interface may comprise one or more testing interfaces. However, in some embodiments, the multi-session testing interface may be enabled to track and manage multiple testing interfaces concurrently. The interface may be segmented into separate feeds such that individual sessions are distinctly managed separately with separate session IDs and in such a way that none of the patients can talk to each other or are even aware that multiple sessions are occurring concurrently. For example, selecting one window of the one or more windows may open a secure communication channel with the patient of the selected window, and closing any other open communication channels. Also, each window may comprise one or more visual or auditory indicators of test status, such that a proctor can more easily manage the one or more patient test sessions occurring concurrently. In some embodiments, the multi-session testing interface may comprise individual testing sessions, each opened in a separate browser window.

Another example multi-session testing interface may comprise one or more patient video feeds. In some embodiments, the patient video feeds may comprise individual concurrent testing sessions with individual patients. In some embodiments, the individual testing sessions may be automatically highlighted or manually selected by a proctor in order to interact with the patient subject of the highlighted session. In some embodiments, the highlighted session may also pop-out or otherwise enlarge relative to the other sessions, such that the proctor may access relevant information. In some embodiments, a proctor may use the interface to monitor a computer algorithm, which may be autonomously administering the tests to patients in patient video feeds. In some embodiments, individual sessions may be highlighted by the algorithm for proctor intervention into the testing session. In some embodiments, the proctor may manually intervene in one or more testing sessions by selecting the desired patient video feed.

Another example multi-session testing interface may comprise a timeline comprising one or more steps or stages $S_n$, wherein n is an integer representing the stage number in a sequence of stages comprising the test protocol. For example, the interface can include a timeline that comprises S1, S2, and S3 representing three stages of a testing protocol. In some embodiments, the interface may comprise one or more patient video feeds. The patient video feeds may be located within the interface in such a way as to indicate the testing stage at which the patient is currently undergoing. For example, in the illustrated embodiments, patient 1 (P1) is at stage 1 (S1), patient 2 (P2) is at stage 2 (S2), and patient 3 (P3) is at stage 3 (S3). In some embodiments, the testing interface may be utilized to allow a proctor to monitor one or more concurrent testing sessions. The testing interface may allow the proctor to easily understand the stage at which each testing session is currently undergoing. In some embodiments, the patient video feeds may change location upon completion of each testing stage, such that the interface is automatically and dynamically updated.

As described previously, the testing platform described herein can be configured to allow for a plurality of users to perform remote health and diagnostic testing under the supervision of one or more proctors. As users access the platform, they can be matched with certain proctors based on various criteria selected to improve the users' testing experience and/or to improve the efficacy of the proctors. In some embodiments, users accessing the platform are placed in a user pool and proctors accessing the platform are placed in a proctor pool. Various criteria can be determined for each of the users and for each of the proctors. These criteria can then be analyzed to match or assign users to certain proctors.

Users may be matched with or assigned to proctors based at least in part on one or more of a variety of different factors. Such factors may include, for example, the languages spoken by the users and the proctors, user disabilities and/or special needs, user and proctor location, types of tests to be taken or administered, a user's level of technical proficiency, proctor availability, strength of network connection, and/or a level of testing, verification, or scrutiny desired or required.

For example, users may be matched or assigned to a proctor based on a language spoken by the user. The testing platform may be provided in multiple languages and available all over the world. Accordingly, users accessing the platform may speak a variety of different languages. To facilitate testing, proctors may be provided in languages that correspond to the languages of the user. When an English-speaking user accesses the platform, they may be assigned to an English-speaking proctor. When a Spanish speaking user accesses the platform, they may be assigned to a Spanish speaking proctor. This can ensure that the proctored testing session can run as smoothly as possible as communication barriers between the users and the proctors can be reduced.

In some embodiments, the language desired by the user for the proctored testing session may be indicated by the user. For example, when accessing the platform, the user may create a user profile in which the user's language preference is indicated. In some embodiments, multi-lingual users may indicate that they can speak more than one language and may even indicate a proficiency for each language. When matching such users to proctors, each language and proficiency may be evaluated in view of the available proctors in order to find a matching proctor as quickly as possible. For example, if a user indicates that he or she is a native Spanish speaker but is also fluent in English, the platform may first check to see whether a Spanish speaking proctor is available. If a Spanish speaking proctor is available, the user may be matched to the proctor. If a Spanish speaking proctor is not available, the platform may then check whether an English-speaking proctor is available, and if so, match the user with the English-speaking proctor.

In some embodiments, the platform may attempt to automatically determine the user's language. For example, the platform may analyze the user's network connection (e.g., the user's IP address) in an effort to determine where the user is geographically located. If, for example, the user's IP address is associated with a typically English-speaking geographical location, the user may be initially presented with an English-speaking proctor. If the user's IP address is associated with a typically Spanish speaking geographical location, the user may be initially presented with a Spanish speaking proctor. Other factors may also be analyzed in an effort to automatically determine the user's language. For example, an estimate of the user's language may be made based on a top-level domain associated with the testing platform's website accessed by the user. For example, if a user accesses the testing platform at www.[testingplatform].mx (.mx being the top-level domain associated with Mexico), the testing platform may make an initial determination that the user likely speaks Spanish. In such cases where the platform attempts to automatically determine the user's language, the user may be given the option to change to a more preferred language in the event that the automatically determined language is incorrect.

Proctors may also be associated with profiles that provide information about the proctors that is used to match the proctors to the users. A proctor profile can include information about which languages are spoken by each proctor as well as a proficiency score for each language. In some embodiments, proctors can specify which languages they speak as well as their proficiency in each language. In some embodiments, proctors may be required to take language tests to ensure that they are sufficiently proficient to provide a proctored test in a given language. In some embodiments, the platform may analyze proctor performance and adjust a proctors proficiency score for each spoken language. For example, a proctor may indicate that he or she is fluent in English and Spanish. The platform may thus assign both English speaking users and Spanish speaking users to the proctor. The platform may analyze the proctor's proficiency in providing proctored testing sessions in English and Spanish. For example, the platform may track an average testing session length for both the English and Spanish sessions. Upon determination that the proctor takes sufficiently longer to provide a proctored testing session in one language when compared to the other, the platform may lower the user's proficiency score for the slower session language. Additionally or alternatively, the platform may evaluate testing accuracy for each of the proctor's spoken languages. For example, if it is determined that tests administered by the proctor in Spanish generally are more accurate than tests administered by the proctor in English, the platform may assign more Spanish speaking users to the proctor. As a result, the platform may assign more users who speak the proctor's faster language to the proctor in the future. In some embodiments, in addition to or in place of comparing the proctor's proficiency against itself (e.g., comparing the proctor's English proficiency against his or her Spanish proficiency), the platform may also compare the proctor's proficiency against that of other proctors. In this way, the platform can dynamically balance matching users to proctors in the most efficient manner.

Another factor that may be considered by the platform in matching or assigning users to proctors can be disabilities or special needs of the users. For various reasons, some users may require special accommodations in order to take a test. The platform can consider the users' needs and provide the user with a proctor equipped to provide the necessary accommodations. As one example, a user that is hard of hearing or deaf can be assigned to a proctor that is proficient in sign language or to a proctor that is proficient in communicated with the user through text. Users accessing the platform may provide information about any special needs or disabilities as well as desired or necessary accommodations that must be made to facilitate the testing session. Similarly, proctor profiles can store information about skills or accommodations that a proctor can provide. Similar to the proctor language information described above, a proctor's ability to accommodate a disability or special need can be evaluated by the platform. For example, testing session duration and/or accuracy of test results can be analyzed and used to rebalance proctor assignment over time such that that proctors can be assigned and matched to users in a manner that maximizes the overall efficiency of the system.

In some embodiments, the platform may match users to proctors based on the location and/or time zone of the users and proctors. This may improve the testing experience by matching users to proctors that are close to them geographically or in the same time zone.

In some embodiments, proctors and users can be matched based on the type of test to be taken. As noted above, the platform may be configured to allow for a wide variety of remote health tests or other diagnostics. While users accessing the platform may generally do so in order to take a specific kind of test, proctors may be able to administer more than one type of test. For example, a proctor may be able to provide a proctored testing session for a first type of test and also to provide a proctored testing session for a second type of test. Proctor profiles may include a list of each type of proctored testing session that can be provided by a given proctor. In some embodiments, proctors may need to take specific training and/or receive certain verifications to provide different types of proctored testing sessions.

In some embodiments, proctors that are certified or otherwise able to provide different types of proctored testing sessions can be evaluated by the platform such that users are assigned to the proctor in an efficient manner. For example, if both a proctor A and a proctor B are capable of administering a first type of proctored testing session and a second type of proctored testing session, the platform may evaluate proctor A and B's proficiency with each type of testing session and match users accordingly. For example, the platform may determine that proctor A provides the first type of proctored testing session more quickly than proctor B does. The platform may then assign users taking a test associated with the first type of proctored testing session to proctor A and assign users taking a test associated with the second type of proctored testing session to proctor B.

Another factor that can be considered by the platform in assigning users to proctors may be the users' technical ability or proficiency. As an example, an older user may not be as technically proficient as a younger user. Certain proctors may have more proficiency in providing proctored testing sessions to such older users. Accordingly, the platform may assign such older users to such proctors. In some embodiments, the users themselves may provide an indication of their technical proficiency. For example, during user account creation or a pre-qualification survey, the user may input a technical proficiency score or a comfort score associated with using the remote testing platform. In some embodiments, the platform may make a determination about a user's technical proficiency based factors observable by the system. For example, the system may make a determination about a user's technical proficiency based on an amount of time take by the user to set up his or her account or to complete the pre-qualification survey. As another example, the platform may make a determination about the user's technical proficiency based on the user's age or other factors. In some embodiments, the system may automatically administer a short test to the user to determine technical proficiency, for example, by checking whether the user is able to operate his or her webcam, microphone, and speakers.

As before, the platform may continually or periodically evaluate proctor proficiency in providing proctored testing sessions to less technically proficient users. For example, the platform may analyze elapsed session times or test result accuracy for various proctors and assign less technically proficient users to proctors that can most efficiently and accurately administer tests to such users.

The platform may also consider the strength of users' and proctors' network connections in determining how to assign and match the users and proctors. For example, the platform may evaluate or determine an internet speed, latency, and/or reliability of the network connection for each user and proctor. This information can be used to match proctors and users in a manner that ensures that a stable connection between a user and proctor can be maintained during a testing session.

In some embodiments, the platform may also consider a level of testing verification or scrutiny that is required or desired in determining how to assign and match users to proctors. For example, in some instances, a certain level of proctor scrutiny or involvement may be required to complete and validate a test result. For example, government or other regulatory bodies may require certain steps to be completed in order to validate a test. In such cases, users can be matched with proctors that are capable of providing the needed level or scrutiny. In other example, users may request a certain level or proctor involvement or scrutiny. For example, a user that is generally unsure or uncomfortable with remote testing procedures may request a more involved proctoring session.

Accordingly, users who require or desire a proctoring session with additional verification measures or a higher level of testing scrutiny may be matched with proctors who conduct one-on-one proctoring sessions and/or can provide additional verification services. As one example, users who need verified passes in order to comply with CDC rules or laws may be matched with proctors capable of providing such services. As another example, in some embodiments, users may pay for a premium membership/service for the platform that automatically communicates the users' test results to user-specified entities. For example, the platform can provide users with a with a TSA Pre-Check-like pass service where the user provides additional verification information and performs additional verification processes with the proctor in exchange for a pass that allows users to "skip the line" or otherwise more seamlessly travel or access various venues and other locations.

The system may also consider proctor availability in matching users and proctors. As noted above, the platform may consider various factors in matching users and proctors to improve the efficiency and accuracy of the platform. In some embodiments, however, the most efficient proctors may not be available. Accordingly, the platform can further consider proctor availability. For example, in some embodiments, it may be faster to assign a user to a less proficient proctor with a shorter wait time, rather than assigning the user to more proficient proctor with a longer wait time.

The platform may dynamically match proctors and users upon consideration of one or more of the factors described above as well as others. Further, the platform may continually or periodically evaluate the efficiency and accuracy of proctors based on each of these factors and use this information to continually rebalance and recalibrate the platform to maximize efficiency. For example, the platform may adjust how users are assigned to proctors to reduce testing session times and/or improve testing session accuracy by assigning proctors to users in the most efficient manner.

Additionally, the order in which users are placed in queues for meeting with proctors may be determined based at least in part on one or more of a variety of factors. As noted above, in some instances, a user may be placed into a waiting room while waiting for a proctor to be assigned or while waiting for an assigned proctor to become available. The order in which users are matched to proctors and/or assigned to available proctors may also be considered by the system. For example, in some embodiments, a level of testing urgency or priority associated with each of the various users that are to meet with proctors may be considered. The level of testing urgency or priority that is associated with a given user may be a function of one or more of a variety of parameters. These factors may include, for example, how soon the user will be boarding a flight, whether the user is crossing a state or international boarder, how at-risk the user may be, how symptomatic the user may be, the user's current test pass status, the user's occupation or other status, the time spent waiting in queue, and/or a user's membership tier associated with the user platform, among others.

For example, a user that is about to board a flight or travel across state lines or other boarders may be given an advantageous place in the queue in an effort to assure that the travel can be completed. As another example, a more at-risk user may be given an advantageous place in the queue to minimize his or wait time. An at-risk user may be one that has a pre-existing condition or is elderly. For example, the elderly and people with certain health conditions may be placed ahead of others in the queue in order to ensure that they can be tested as soon as possible. As another example, a more symptomatic user may be given an advantageous place in the queue. People who are exhibiting worrisome symptoms may be placed ahead of others in the queue so that they can receive the medical attention they might need sooner. This can improve health outcomes for the particular patient as well as minimize the spread of a contagious disease to others.

A user's place in queue may be assigned in part based upon whether or not the user has a test pass that is currently valid and/or the amount of time remaining until expiration of a user's current test pass. For example, people who do not have test passes that are currently valid and people who have test passes that will be expiring shortly may be placed ahead of others in the queue. The user's occupation or other status may also be considered in determining queue placement. For example, doctors or medical personnel may be placed ahead of others in the queue. Additionally, time spent waiting in queue may also be considered. For example, users who have not been waiting for very long may be placed behind users in the queue who have been waiting for a while. In some embodiments, the platform may provide premium memberships or services that can affect a user's placement in the queue. For example, users that pay for a premium membership or service may be placed ahead of others in the queue.

The user-proctor matching and user queuing techniques and features described above have generally been presented in the context of assigning users to proctors for proctored based testing sessions. However, in some embodiments, different proctors may be provided for different portions of a proctored testing session. Accordingly, the user-proctor matching and user queuing techniques and features described above can be implemented at different stages in proctored testing session along the process. For example, a user may be shifted to different proctors throughout a test, with different proctors providing different stages or steps in the process. Proctors can be evaluated for proficiency and accuracy in providing the different stages of the tests (in some embodiments, for different types of users), and users and proctors can be matched accordingly.

In some embodiments, some phases or steps in a testing process may require more direct supervision, while other stages may require less supervision. In some embodiments, during stages that require more direct supervision a lower ratio of proctors to users may be used, while in stages that require less supervision a higher ratio or proctors to users may be used. Proctors can be evaluated to determine whether they are more proficient in proctoring the steps that involve supervision of a higher number of users or in proctoring the steps that involve supervision of a lower number of users, and the platform may match users and proctors accordingly.

First Aid Guidance

Figure 32:
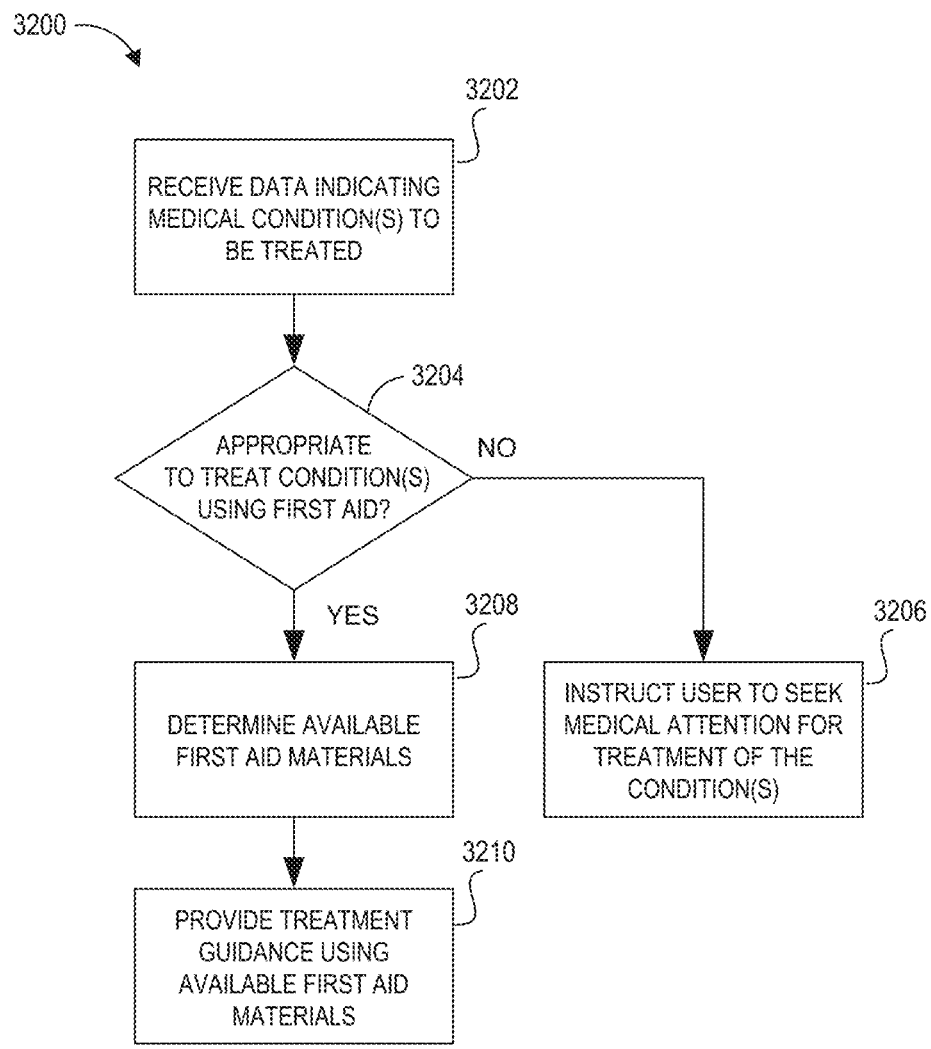
FIG. 32 is a flowchart illustrating an embodiment of a system-side method for providing first aid guidance according to the present disclosure.

FIG. 32 is a flowchart illustrating an embodiment of a method 3200 for providing first aid guidance according to the present disclosure. The method 3200 illustrated in FIG. 32 represents system-side or server-side steps of the method. For example, the method 100 illustrated in FIG. 32 represents steps that can be performed by a first aid guidance system while interacting with a user. The user may be a user in need of first aid (e.g., an injured person) or a user that is providing first aid to another. The user may provide inputs into the system and receive responses from the system. In some embodiments, the method 3200 may be a computer-implemented method. A computer-implemented method can be performed using a computer system, such as, for example, the computer systems described below with reference to FIG. 41. In some embodiments, the computer-implemented method can be performed on a user device, such as a personal computer, a cellular phone, a smartphone, a laptop, a tablet computer, an e-reader device, an audio player, AR glasses or goggles, or another device capable of connecting to and communicating over a network, whether wired or wireless.

While FIG. 32 represents the method 3200 from the system- or server-side, FIG. 33 (described further below) illustrates a corresponding example method 3300 from the user-side. Additionally, in some embodiments, one or more of the method steps illustrated in FIG. 32 can be omitted and/or rearranged in other embodiments. Some examples of method steps that can be omitted or rearranged are described below, although the described examples do not provide an exhaustive list and those of ordinary skill in the art, upon consideration of this disclosure, will appreciate that other modifications to the method 3200 are possible. In some embodiments, additional method steps (e.g., method steps that are not illustrated in FIG. 32) may also be included. FIG. 34 (described further below) illustrates another method 3400 that includes several additional method steps. Those of ordinary skill in the art, however, will appreciate that other method steps (e.g., beyond those illustrated in the figures) may also be included.

In general, the method 3200 is configured for providing first aid guidance to a user. That is, the method 3200 can receive information about a medical condition in need of treatment (and optionally, also receive information about first aid materials that are available to the user) and provide guidance to the user for providing first aid for the medical condition. In some embodiments, the guidance may be specific to or tailored based on the first aid materials that are available to the user. These and other features and advantages of the method 3200 will now be described in more detail with reference to the method steps illustrated in FIG. 32.

The method 3200 may begin at 3202, at which the system receives data indicating one or more medical conditions to be treated. The data can be provided by a user accessing the system on a user device, such as a personal computer, a cellular phone, a smartphone, a laptop, a tablet computer, an e-reader device, an audio player, AR-glasses or goggles, or another device capable of connecting to and communicating over a network, whether wired or wireless. In some embodiments, the system is configured as a web-based application that is accessed using the user device. In some embodiments, the system comprises an application installed on the user device. In some embodiments, the system comprises an application installed on the user device that is configured to communicate with a backend system (e.g., a system located on a remotely located server) over a network, such as, for example, the internet.

At 3202, the data indicating the one or more medical conditions to be treated can be provided to the system in a wide variety of ways. For example, the system can receive user input(s) specifying one or more medical conditions to be treated, for example, through one or more text entry fields of a graphical user interface (GUI) that is presented to the user on the user device. The user may be presented with one or more prompts that ask the user to describe the medical condition to be treated and corresponding text entry fields into which the user can input his or her response. User responses input into the text entry fields can be analyzed by the system to determine the medical condition to be treated. In some embodiments, users may provide inputs into the text entry fields using natural language and the system can include a natural language algorithm or module that parses the user inputs to determine the medical condition to be treated from the user inputs.

In some embodiments, the system may be configured to, in response to receipt of some user inputs, follow up with additional prompts and corresponding text entry fields to gather additional information about the medical condition to be treated. For example, the system may first ask the user to describe the medical condition in need of treatment. The user may provide a reply indicating that the injury to be treated is a cut. The system may then respond to the user with additional prompts configured to gather additional information about the cut. For example, the system may prompt the user to input the location of the cut, a description of the cut (e.g., length, depth, etc.), amount of bleeding, or other information. In this way the system can gather the needed information to provide accurate guidance for treating the medical condition.

In some embodiments, the one or both of the prompts and/or text entry fields can be replaced with audio communications. For example, the system may audibly ask the user to describe the medical condition in need of treatment (e.g., using speakers of the user device) and/or allow the user to speak his or her descriptions of the medical condition to be treated. Spoken descriptions of the medical condition to be treated can be captured, for example, using a microphone on the user device. The system may process the spoken descriptions (e.g., using a speech-to-text algorithm) so that information about the medical condition to be treated can be extracted from the user's audio or voice inputs. In some embodiments, use of audio or voice to receive information from or input information into the system can be beneficial as it can allow the user to access the system in a hands-free manner. This can, for example, free up the user's hands to perform first aid or accomplish other tasks, as necessary.

As another example, at 3202, the data indicating the one or more medical conditions to be treated can be provided to the system through a series of drop down (or other similar) menus that can be provided to the user on a graphical user interface on the user device. For example, the user may be asked to select the medical condition to be treated from among a plurality of general options provided to the user. In some embodiments, based on the initial medical condition selected by the user, further sets of options can be presented to the user in order to gather additional information about the medical condition. For example, if the user selects "cut" as from among an initial set of options, further sets of options can be provided wherein the user can select a location of the cut, a length of the cut, a level of bleeding, and/or other types of information describing the cut. Use of a tiered system of drop-down options, for example, can allow the system to quickly and efficiently gather the information needed in order to determine the medical condition to be treated, while also minimizing the work required by the user. For example, the user can quickly select the relevant information from among the lists of options presented. Although described in the context of drop-down menus, such tiered systems of options can be presented in other manners as well, such as nested checkable lists or others.

As another example, at 3202, the data indicating the one or more medical conditions to be treated can be provided to the system in the form of one or more images or videos. For example, using a camera on the user device, the user may take one or more images or videos of an injury. The system can analyze these images or videos to determine the medical condition to be treated, for example, using computer vision and/or machine learning. In some embodiments, the images or videos can be transmitted to a remotely located healthcare professional who can review the images or videos to determine the medical condition in need of treatment.

In some embodiment, the system can receive multiple types of data from the user regarding the medical condition. For example, the system can receive a plurality of text data, voice data, selected option data, image data, and/or video data, and the system can determine the medical condition to be treated based on the plurality of data sources.

Upon receiving data indicating the medical condition to be treated at 3202, the method 3200 can move to decision state 3204. At decision state 3204, a determination is made as to whether it is appropriate to treat the condition(s) indicated at 3202 using first aid. Some medical conditions (e.g., complicated and/or life-threatening conditions) may need to be addressed by a doctor or other medical professional, while other medical conditions (e.g., minor injuries) can be treated at home using common first aid materials. At decision state 3204, the system may effectively determine whether the medical condition specified at 3202 falls into the former or the latter category. For example, the system may maintain and/or have access to a list of conditions that can be treated at home using commonly available first aid kit materials. The medical condition determined at 3202 can be compared against this list of conditions to determine the specified medical condition(s) is suitable for at-home first aid treatment or whether the user should seek professional medical care.

In some embodiments, there may also be a severity component to the aforementioned list of conditions. For example, in some such embodiments, the determination as to whether certain wound-related conditions might be "treatable at home" or could be better addressed by professional care may depend on one or more factors such as how much blood has been lost, how much time has passed since the incident occurred that caused the injury, how long/deep a cut is, what a cut was caused by, and the like. Additional factors that could be taken into consideration in determining whether different conditions might be "treatable at home" or could be better addressed by professional care may include symptoms, such as whether or not the patient is feeling nauseated, has feeling in the affected area, is losing consciousness, and so on. Information concerning one or more of the aforementioned factors may be gleaned by the system at 3202. In addition, factors pertaining to the user's accessibility to professional medical care may also be taken into account at 3204. For instance, the system may take the distance or estimated travel time to/from nearest healthcare professional from the user's location, the country or region where the user(s) is/are located, and the like in account at 3204. Other factors that may be considered at this juncture include conditions specific to the users such as known or unknown allergies, disabilities, immune deficiencies, and so on.

In the event that a determination is made that it is not appropriate to treat the condition(s) indicated at 3202 using at-home first aid, the method 3200 moves from decision state 3204 to 3206, at which the user is instructed to seek medical attention for treatment of the condition(s). At 3206, the system can instruct the user to consider seeking professional medical attention for treatment of the specified medical condition(s), for example, by way of a prompt that is displayed to the user through the GUI of the user device. For example, the system may indicate to the user that the medical condition is potentially serious and likely requires professional treatment. For instance, the system may proceed from decision state 3204 to 3206 in a situation where the user has specified that they would like to receive first aid guidance for treating a compound fracture, which is a condition that is best treated by a medical professional.

In some embodiments in which the medical condition determined at 3202 is sufficiently serious, the method may, at 3206, provide the user with an option for contacting emergency services. For example, at 3206, the method may provide the user with a button that can be selected to automatically call 9-1-1. In some embodiments, at 3206, the method 3200 may additionally call or notify a specified emergency contact of the user with information concerning the user's condition, whereabouts, and the like. Additionally, in some embodiments, in some embodiments, metadata that may be helpful in treating the specified medical condition may also be obtained by the system and routed to the appropriate emergency service personnel at 3206. Examples of such metadata can include GPS data, pictures taken of injuries (e.g., during the aforementioned diagnosis process), name/contact information for the user whose phone/device was used, and the like. The provision of such metadata by the system may be especially useful in situations where users may not have a continuously reliable cellular or wireless broadband connection (e.g., the user is on a boat that is drifting in and out of areas of cellular coverage, the user is in a foreign country, etc.).

In other embodiments, in which the medical condition determined at 3202 does not require calling emergency service but is still sufficiently serious such that at-home first aid will not likely not be able to properly address the situation, the method 3200 may, at 3206, prompt the user to visit an emergency room, urgent care, doctor's office, or other healthcare clinic to receive appropriate treatment. In some embodiments, at 3206, the method 3200 may also provide the user with a set of initial treatment steps that should be taken before seeking professional care. For example, the user may be prompted to apply a bandage to a cut before going to a healthcare professional to receive stitches. Additionally, in some embodiments, the method 3200 may, at 3206, provide the user with a button that can be selected to automatically call and/or schedule an appointment at one or more of the aforementioned medical care facilities, call or notify a specified emergency contact of the user, or a combination thereof.

Returning to decision state 3204, in the event that a determination is made that it is appropriate to treat the condition(s) indicated at 3202 using first aid, the method 3200 moves from decision state 3204 to 3208, at which available first aid materials are determined, and to 3210, at which first aid guidance is provided to the user. For instance, the system may proceed to 3208 and 3210 in a situation where the user has specified that they would like to treat a minor cut, wound, or splinter, which are conditions that can often be effectively treated using materials commonly found in first aid kits.

In some embodiments, method step 3208 can be omitted, and the method 3200 can proceed directly from decision state 3204 to 3210, which is described further below. However, for other embodiments that include this step, method step 3208 will now be described. It is noted that method step 3208 can occur at other time points and the method 3200 should not be construed as being limited to having method step 3208 occur only at the illustrated position. For example, method step 3208 can occur before, after, or concurrent with method step 3202 and/or decision state 3204. At 3208, the system determines which first aid materials are available to the user. The specific first aid materials that are available to the user can be used by the system to provide tailored first aid guidance to the user at 3210 (described below). In the event that 3208 is omitted, the method 3200 can proceed to 3210 at which first aid guidance can be provided without specific reference to the first aid materials that are available to the user.

At 3208, the determination of first aid materials that are available to the user can be made in a wide variety of ways. For example, in some embodiments, the system may seek to determine whether the user has a first aid kit on hand, and if so, what kinds of materials are included in the first aid kit. In some such embodiments, at 3208, the system may instruct the user to retrieve their first aid kit and/or specific materials from said first aid kit. In embodiments, the system may determine whether the user possesses a first aid kit based on user input. The user input regarding the first aid kit can be provided in any manner, including any of the ways described above with reference to 3202 for receiving information about the type of medical condition to be treated. For example, information regarding any available first aid kit or other first aid materials can comprise text data (e.g., data entered into a text entry field), voice data (e.g., user spoken information captured by a microphone), selected option data (e.g., user selections from drop down or other menus), image data, and/or video data (e.g., images or videos captured of the user's first aid kit and/or other first aid materials).

According to some embodiments, the user may be prompted (e.g., through a text entry field or dropdown menu of a GUI that is presented to the user on the user device) with a question asking whether the user is in possession of a first aid kit. In the event that the user does possess a first aid kit, the method may, at 3208, further determine the contents of the user's first aid kit based on one or more of the following:

(1) Data indicating the make (and/or model) of the user's first aid kit. In some embodiments, such information can be obtained through user input (e.g., received through a text entry field or dropdown menu of a GUI that is presented to the user on the user device) specifying the manufacturer of the first aid kit. For example, the user may be asked to type in (or otherwise provide data) indicating the make (and/or model) of the user's first aid kit. As another example, the user may be asked to select his or her first aid kit from among a plurality of options. Alternatively or additionally, the data indicating the make (and/or model) of the user's first aid kit can be provided in the form of one or more images of the first aid kit as captured by a camera on the user device. For example, the user could take an image or video of the exterior of the first aid kit and the system can analyze the image or video to determine the make and/or model of the first aid kit. In some embodiments, analysis of the image to determine the make and/or model of the first aid kit can involve computer vision and/or machine learning configured to read packaging of labeling information on the first aid kit. In some embodiments, analysis of the image to determine the make and/or model of the first aid kit can involve interpreting a machine-readable code included on the first aid kit. For example, the first aid kit can include a barcode, QR code, or other type of machine-readable code. The system can analyze the image to read the machine-readable code and extract information about the make and/or model of the first aid kit there from. An example will be described in more detail below with reference to FIG. 36. Once the make and/or model of the first aid kit is determined, the system can determine the likely contents of the first aid kit through the use of a database that stores makes and/or models of first aid kits and their contents. In some embodiments, a healthcare professional or other trained professional may assist with the capture and/or interpretation of the aforementioned data and thus play role in the determinations that are made at 3208.

(2) Data indicating the contents of the first aid kit. In some embodiments, it is not necessary to determine the make and/or model of the first aid kit. Rather, the contents of the first aid kit can be determined. Information about the contents of the first aid kit can be provided to the system via user input in any form, such as any of the forms previously described. For example, the user input can be received in response to presenting the user with a first aid kit "checklist" of first aid materials. The user may work his or her way through a checklist, providing indications of whether each item on the list is contained in the first aid kit or otherwise in the user's possession. Alternatively or additionally, the user may specify, using text or voice, the first aid materials at hand. Alternatively or additionally, the user may capture one or more images of the contents of the first aid kit using a camera on the user device. For example, the user may provide an image or video of the interior of the first aid kit and/or first aid materials belonging to the first aid kit. An example will be described in more detail below with reference to FIG. 37. In some embodiments, the user may capture an image of the contents of the first aid kit while the materials are still positioned within the kit (e.g., a picture of an open first aid kit). In some embodiments, the user may be prompted to remove the contents of the kit and lay them out, such that the contents can be more easily seen within the image. In some embodiments, at least some of the first aid materials or items described herein need not expressly belong to or originate from a commercial kit purchased by the user, but may instead correspond to first aid materials or items purchased or otherwise obtained on an individual basis by the user. Similarly, in some embodiments, first aid materials or items described herein as being in the user's possession and/or used to together to treat a medical condition may include materials or items belonging to or originating from one first aid kit, materials or items belonging to or originating from another, different first aid kit, materials or items obtained by the user in isolation from any first aid kit, or a combination thereof. The system can analyze the image, for example, using computer vision and/or machine learning to determine the available first aid materials.

In embodiments of the method 3200 that include determination of the first aid materials available to the user (e.g., method step 3208), this information can be used together with the data indicative of the medical condition to be treated (e.g., the data collected at 3202) to provide tailored first aid guidance to the user. For example, the method 3200 can, at 3210, provide specific treatment instructions to the user for how to treat the specified medical condition using the available materials. As noted above, however, method step 3208 need not be included in all embodiments.

From 3208, the method 3200 moves to 3210, at which treatment guidance for treating the condition(s) indicated at 3202 is provided to the user. In some embodiments, the treatment guidance is specific to the use of available first aid materials determined at 3208. In other embodiments, the treatment guidance can be generic with respect to the use of commonly available first aid materials. The first aid guidance that is provided at 3210 may be text-based, audio-based, video-based, augmented reality (AR)-based, or a combination thereof. For some embodiments, the purpose of the guidance is to provide the user with step-by-step instructions for treating the specified medical condition(s) using first aid materials that they may have on hand (if previously determined).

For example, the user may be presented, for example, on the display of the user device, with a written set of steps to be followed in order to treat the medical condition. In some embodiments, the system may be configured to audibly provide the steps to be followed. Use of audio instructions can be advantageous as it allows the user to access the instructions in a hands-free manner that allows the user to perform first aid. In some embodiments, the system may provide the user with one or more images or videos that illustrate the first aid steps to be taken. Use of images or video can increase the user's comfort level in following the instructions as it can be, in some instances, easier to understand and/or follow picture or video-based instructions. An example of such guidance will be described in more detail below with reference to FIG. 39.

Figure 38:
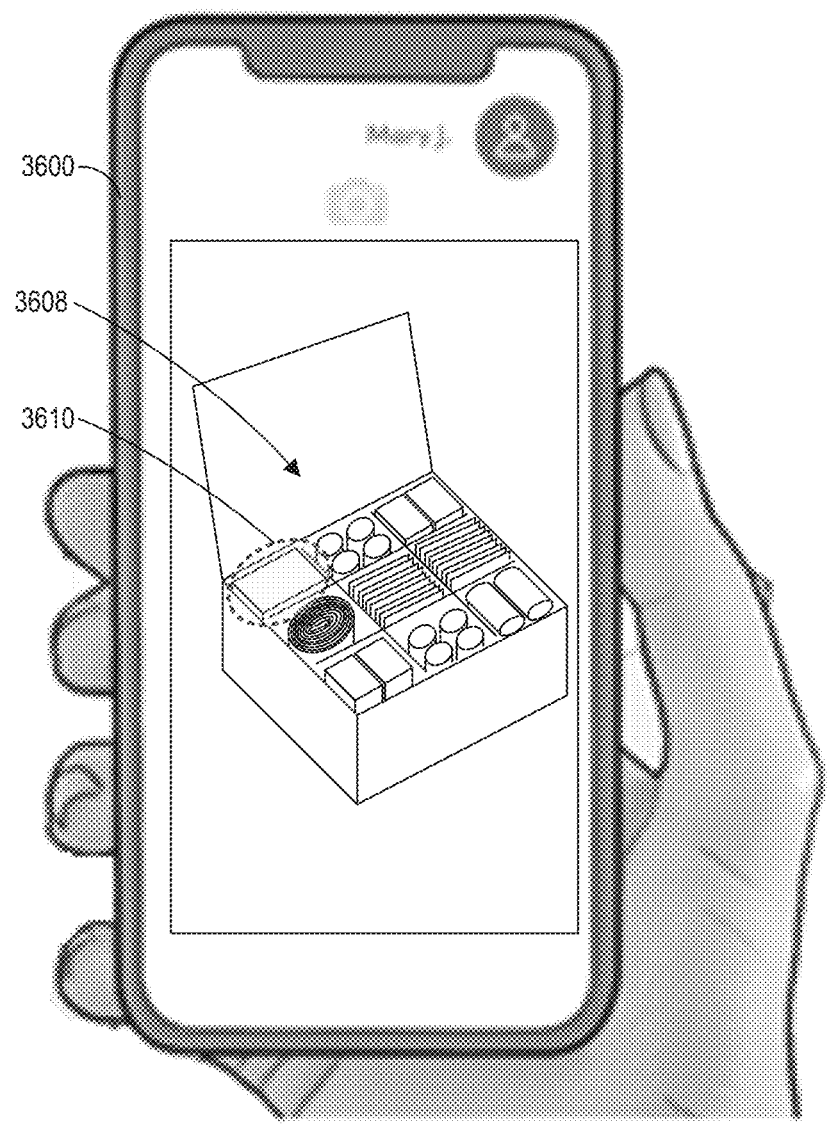
FIG. 38 illustrates an example of providing augmented reality guidance to a user on a user device, such as a mobile phone, as part of a method or system for providing first aid guidance according to embodiments described herein.

In some embodiments, the system may utilize AR in order to further communicate the first aid guidance to the user. For example, instructions and/or other indicators can be overlayed onto images and/or video (whether live or prerecorded) captured using cameras on the user device. For example, as part of the first aid guidance, the system may instruct the user to retrieve a specific set of one or more first aid materials for treating the specified medical condition(s), for example, by way of a prompt that is displayed to the user through the GUI. Using AR, the system may highlight the location of the specific set of one or more first aid materials to be retrieved in an image of the user's first aid kit or an image of the user's first aid materials. An example is shown in FIG. 38, which is described in more detail below. In some embodiments, the system may highlight the location of the first aid materials to be retrieved in the image or video that was provided at 3208 to determine the available first aid materials. In some embodiments, the system may highlight the location of the first aid materials to be retrieved in a live image or video of the first aid kit or materials. For example, the user may point the camera of the user device at the first aid kit, causing a live image of the first aid kit to be displayed on the screen. Using AR, the live image can be augmented to highlight or otherwise indicate the location of materials to be retrieved.

AR-based guidance need not be limited to retrieval of first aid materials. Additionally or alternatively, AR can be used to enhance the first aid instructions provided to the user. For example, AR can be used to superimpose instructions for bandaging a cut on a hand onto an image of video (whether live or prerecorded) of the injured hand. Additional examples of how AR can be used to enhance the provision of first aid instructions to users include leveraging AR to show users (A) how to apply stitches to a large cut (e.g., how to thread a needle, the expected length of stitching that will be needed, what the final stitching pattern/distribution/density/insertion points should be for the size and type of wound as interpreted by the system, showing 3D visuals of how to use the appropriate knots to tie the stitching off, etc.), (B) how and where to inject an epinephrine autoinjector ("EpiPen"), including how to open the EpiPen case, where on the body or leg to inject it, indicate (potentially via a timer or countdown) how long to hold in place during the injection phase, etc., (C) how much gauze and tape to use to adequately cover a scrape depending where it is on a user's appendages, torso, etc. (maximizing coverage while minimizing material waste), (D) how to use an eye washer to flush a user's eye (how much fluid to use to fill the cup, how and where to apply the cup to the eyes and tip back the head to rinse, how long to hold with head tipped back, etc.), (E) how to apply a butterfly bandage (what orientation to apply it across the wound, how to remove and stick the bandage, how many should be used based on the size of the wound), (F) how to use tweezers to remove a splinter (how to orient the tweezers to get under the splinter), (G) how much burn cream to apply to a burn based on its degree/severity and size, the location of desired coverage directly on or around the burn (visualizing cream directly on the wound and around it within some reasonable margin), and roughly how much of the burn cream bottle to use for the size of the wound (e.g., draw an AR dotted line indicator directly on the tube of cream to indicate how much of it will be needed for the burn in question), (H) how to apply a splint to a broken arm or leg (e.g., position a sturdy stick or pole along the limb, tie it to the limb securely, what knots to use, etc.), (I) how to tie a tourniquet (knots, position, length of ribbon, appropriate tightness), and/or (J) how clean a cut with antiseptic spray (visualizing a bottle of antiseptic spray over the location of the cut with animations of the bottle being pumped and spraying out antiseptic fluid with textual indication of the number sprays of antiseptic that are to be applied). Other AR-based first aid guidance experiences are possible and within the scope of the instant application.

In some embodiments, at 3210, the system may, additionally or alternately, link the user to existing resources (e.g., websites, videos, etc.) that can be leveraged for purposes of providing the user with first aid guidance. For example, the system may maintain a database of links to external resources that provide guidance on how to treat various medical conditions using first aid materials. When appropriate, the system may link the user to these materials to provide further guidance and instruction for treating the medical condition. In some embodiments, at least a portion of such resources may correspond to content originally developed by, for, or in connection with the entity that maintains the system described with reference to FIG. 1 or an entity associated therewith.

In some embodiments, the system may connect the user with a proctor or other healthcare professional who can help provide the user with such guidance and answer questions that the user may have. For example, the system may provide the user with an option to connect to a live healthcare professional who can walk the user through providing first aid. In some embodiments, audio and/or video channels between the user and the healthcare professional can be provided. These features will be described in more detail below with reference to FIG. 35.

As described above, the method 3200 provides an effective mechanism for providing first aid guidance to a user by, for example, determining the medical condition to be treated, verifying that use of at-home first aid is appropriate for the specified condition, determining available first aid materials, and providing treatment guidance for treating the medical condition using the available materials. Many users may be uncomfortable providing first aid as they may not know what needs to be done to treat various medical conditions. Through the use of the method 3200, these users can be provided with simple guidance that can make providing first aid a better experience. This can improve the users' confidence in their ability to provide first aid as well as improve treatment outcomes for those receiving the first aid.

Figure 33:
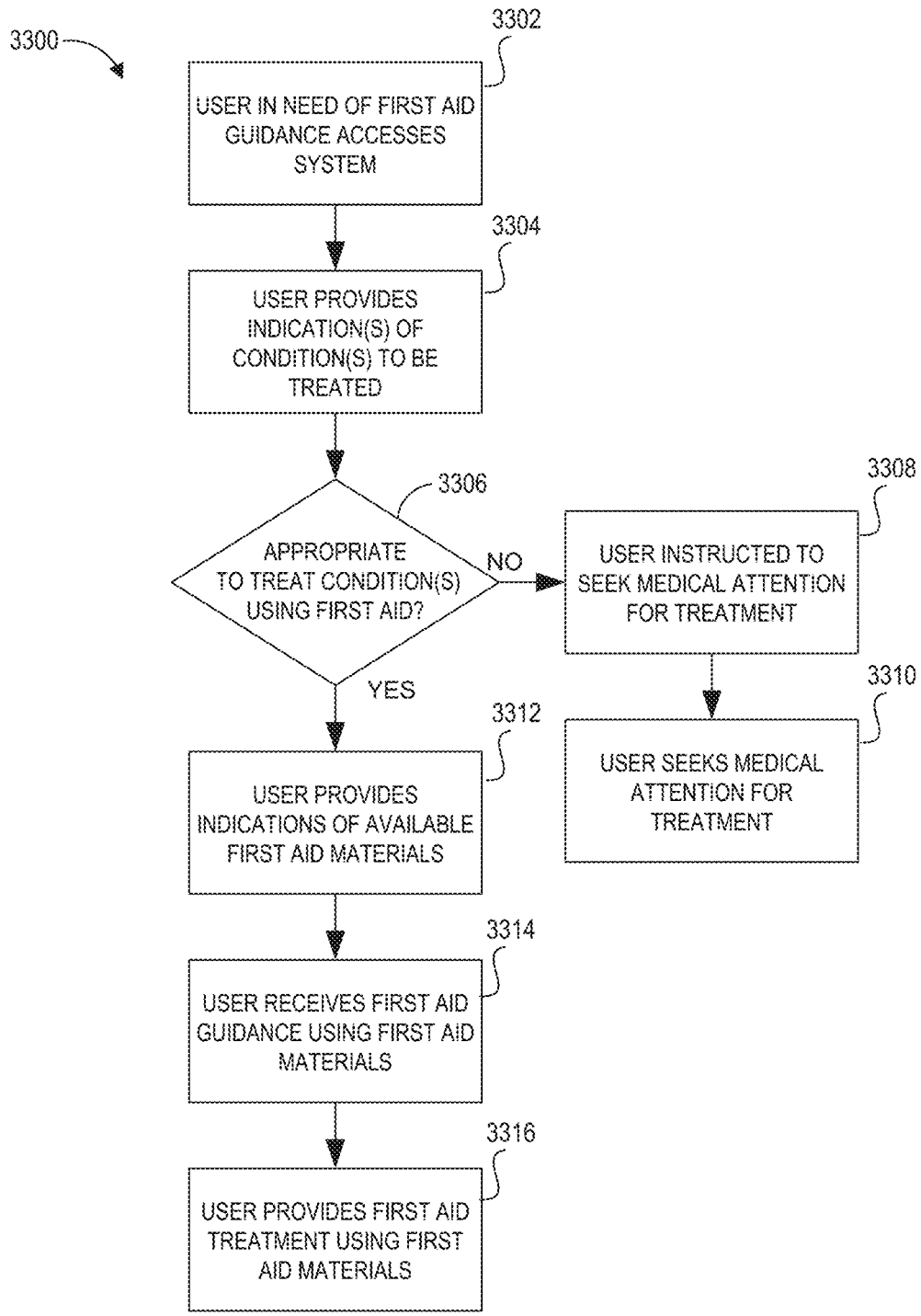
FIG. 33 is a flowchart illustrating an embodiment of a user-side method for providing first aid guidance according to the present disclosure.
Figure 34:
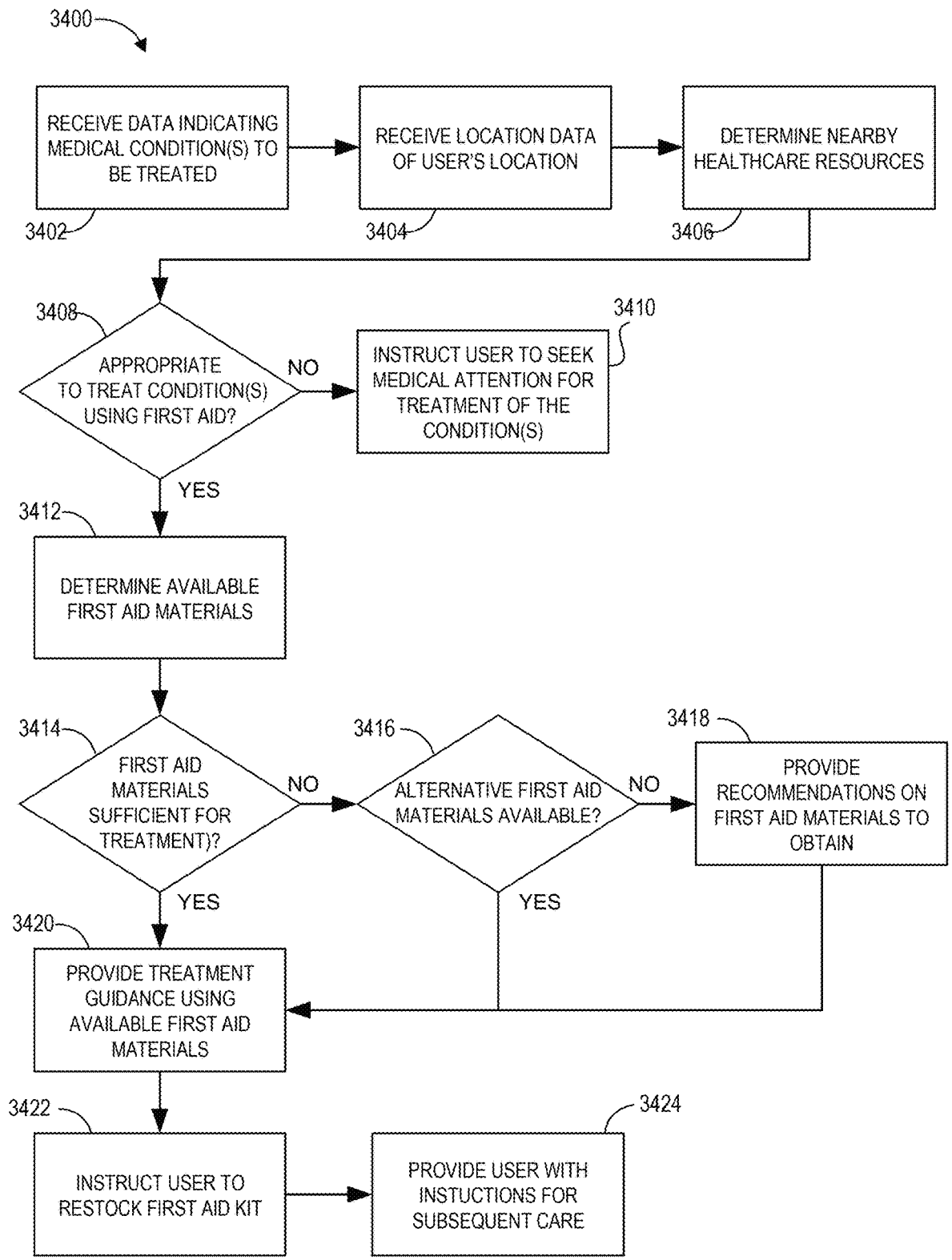
FIG. 34 is a flowchart illustrating another embodiment of a system-side method for providing first aid guidance according to the present disclosure.

FIG. 33 is a flowchart illustrating an embodiment of a user-side method 3300 for providing first aid guidance according to the present disclosure. The user-side method 3300 of FIG. 33 generally corresponds to the system-side method 3200 of FIG. 32, but is presented from the perspective of the user (e.g., a person accessing a first aid guidance system as described herein). The method 3300 begins at 3302, at which a user in need of first aid guidance accesses a first aid guidance system. The user may be a person in need of first aid (e.g., a user performing first aid on his or herself) or a person that will perform first aid on another. The user may access the system in a wide variety of ways. For example, the user may access the system using a user device, such as a personal computer, a cellular phone, a smartphone, a laptop, a tablet computer, an e-reader device, an audio player, AR-glasses or goggles, or another device capable of connecting to and communicating over a network, whether wired or wireless. The system may be available to the user as, for example, a web-based application that is accessed using the user device, an application installed on the user device, or as an application installed on the user device that is configured to communicate with a backend system (e.g., a system located on a remotely located server) over a network, such as, for example, the internet. In some embodiments, the user accesses the first aid guidance system by scanning a machine-readable code included on a first aid kit. For example, a first aid kit can include a machine-readable code (e.g., a bar code or QR code) that links the user to the first aid guidance application.

In some embodiments, such a machine-readable code may be provided on a component of a first aid kit itself, such as the exterior packaging of a bandage or bottle of ointment. For situations in which the user launches or is already running an app or web app that is associated with the system on their user device, in some embodiments, the app or web app may leverage one or more image or speech recognition techniques at or immediately prior to 3302. For example, the app or web app may leverage one or more image or object recognition techniques to recognize a first aid kit or wound/injury shown in one or more images captured by a camera of the user device at 3302 and may proceed to 3304 or 3306 in response thereto. For instance, upon pointing the camera at a burn wound, the system may recognize the injury and subsequently present the user with audible or textual questions of relevance (e.g., "Do you need help treating a second degree burn?" and "Do you have a first aid kit or some burn cream handy?"). As another example, the application or web application may leverage one or more speech recognition techniques to listen for and recognize specific utterances of the user (e.g., "Hey, help me treat a cut!") at 3302, and may proceed to 3304 or 3306 in response thereto. In some embodiments, the app or web app may not be running or open on the user device and may instead be indirectly accessed by the user at 3302 with speech via a third-party system (e.g., an OS- or browser-level speech recognition system).

After accessing the system at 3302, the method 3300 moves to 3304, at which the user provides indication(s) of the condition(s) to be treated. The indication(s) can be provided as described above with reference to method step 3202 of the method 3200 of FIG. 32. Next, the method 3300 moves to decision state 3306, at which it is determined whether it is appropriate to treat the specified condition(s) using at-home first aid. This process has been described above with reference to decision state 104 in FIG. 32. If, at 3306, it is determined that at-home first aid is not appropriate (e.g., due to the severity or complexity of the condition in need of treatment), the method 3300 moves to 3308, at which the user is instructed to seek medical attention for treatment. As described above with reference to 3206 of FIG. 32, the user may be provided with instructions to visit an emergency room, urgent care, doctor's office, or other healthcare clinic to receive appropriate treatment. At 3310, the user can follow the instructions provided at 3308 to seek medical attention for treatment.

Returning to decision state 3306, if it is determined that at-home first aid is appropriate, the method 3300 can move to 3312, at which the user may provide indications of available first aid materials. The indications of available first aid materials can be provided as described above with reference to 3208 of the method 3200 of FIG. 32. In some embodiments, the method step 3312 can be omitted (as described above with reference to method step 3208 of FIG. 32), and the method 3300 can move directly from decision state 3306 to 3314. Whether passing through 3312 or not, at 3314, the user receives first aid guidance. The first aid guidance can be provided in a wide variety of ways, including any of the ways previously described with reference to 3210 of FIG. 32. At 3316, the user provides first aid according to the guidance received at 3314.

FIG. 34 is a flowchart illustrating another embodiment of a system-side method 300 for providing first aid guidance according to the present disclosure. In some respects, the method 3400 is similar to the method 3200; however, the method 3400 also includes additional detail and steps that can be included in some embodiments of a first aid guidance system of method. In some embodiments, the method 3400 may be a computer-implemented method. A computer-implemented method can be performed using a computer system, such as, for example, the computer systems described below with reference to FIG. 41. In some embodiments, the computer-implemented method can be performed on a user device, such as a personal computer, a cellular phone, a smartphone, a laptop, a tablet computer, an e-reader device, an audio player, AR-glasses or goggles, or another device capable of connecting to and communicating over a network, whether wired or wireless. In some embodiments, one or more of the method steps illustrated in FIG. 34 can be omitted and/or rearranged in other embodiments. Some examples of method steps that can be omitted or rearranged are described below, although the described examples do not provide an exhaustive list and those of ordinary skill in the art, upon consideration of this disclosure, will appreciate that other modifications to the method 3400 are possible.

The method 300 begins at 3402, at which data indicating the medical condition(s) to be treated is received, for example, from the user. Method step 3402 may be similar to 3202 of FIG. 32 (described above). At 3404, the system can receive location data indicative of the user's location. Although illustrated following 3402, 3404 can occur at other times during the method 3400. For example, 3404 can occur before, concurrent with, or after 3402. In some embodiments, 3404 occurs immediately after 3402. In other embodiments, additional steps may occur between 3402 and 3404. At 3404, the system receives location data indicative of the user's location. Such information can be provided by the user. For example, the user may enter his or her address via a text entry box or by speaking the address. Such information can be provided by the user device. For example, the user device may include a global positioning system (GPS) component that can determine the location of the device and provide the location to the system at 3404. As will be described in more detail below, the user's location may be used in various other steps of the method 3400.

For example, at 3406, the system may determine whether any healthcare resources are located nearby to the user. Such healthcare resources can include, for example, treatment facilities (e.g., hospitals, emergency rooms, urgent care facilities, doctors' offices, or other healthcare clinics) and/or facilities or retail establishments that sell or provide first aid treatment materials (e.g., drug stores, etc.). For example, the system may, upon receiving the user's location at 3404, generate a list of nearby healthcare resources at 3406 that are located within a certain distance (e.g., 1 mile, 5 miles, 10 miles, 50 miles, etc.) of the user. As will be described in more detail below, this information may be used in various other steps of the method 3400. Although illustrated immediately following 3404, 3406 can occur at other times during the method 300. For example, 3406 need not immediately follow 3404.

In the illustrated embodiment, the method 3400 moves from 3406 to decision state 3408. Decision state 3408 involves determining whether it is appropriate to treat the condition determined at 3402 using at home first aid. In some embodiments, decision state 308 can be similar to decision state 3204 described above with reference to FIG. 32. In some embodiments, decision state 3408 can also consider, for example, the user's location (determined at 3404) and the available nearby healthcare resources (determined at 3406). For example, in some instances, a severe medical condition may not be suitable for at-home treatment due to severity and/or complexity. However, if no suitable healthcare facilities are located in proximity to the user, at-home treatment (at least initially) may be the only option. Accordingly, in some embodiments, decision state 3408 may consider the user's location and the availability of nearby healthcare resources in addition to the nature of the condition to be treated in determining whether at-home first aid treatment is suitable.

If, at decision state 3408, it is determined that it is not appropriate to treat the condition using first aid, the method 3400 can move to 3410, at which the user is instructed to seek medical attention for the treatment of the condition. Method step 3410 can be similar to 3206 of FIG. 32 (described above). In some embodiments, 3410 can also involve providing the user with a list of suitable nearby treatment facilities. For example, the user may be instructed to visit a nearby emergency room for treatment and can be provided with the address and/or GPS guidance from the user's location to the hospital. In some embodiments, where emergency services (e.g., 9-1-1 services) are necessary, the user's location (determined at 3404) can be provided directly to emergency services, such that an ambulance (or other resources as appropriate) can be routed to the user.

Returning to decision state 3408, if it is determined that it is appropriate to treat the condition using first aid, the method 3400 can move to 3412, at which available first aid materials can be determined. Method step 3412 can be similar to 3208 of FIG. 32 (described above).

From 3412, the method 3400 can move to decision state 3414. At decision state 3414, the system can determine whether the first aid materials available to the user are sufficient to treat the condition indicated at 3402. For example, the system may maintain a database of first aid supplies necessary to treat various conditions. The system can crosscheck the available first aid materials and the medical condition against the database to determine whether the user is in possession of sufficient materials.

From decision state 3414, if it is determined that the user is not in possession of sufficient materials, the method 3400 can move to decision state 3416, at which the system assesses whether the user is in possession of any alternative first aid materials that would be suitable for providing the necessary treatment. As one example, at 3412 it can be determined that the user's first aid kit does not include gauze. At 3414, it can be determined that without gauze, the user is not in possession of the ideal materials for treating a given condition that is generally treated by applying a gauze bandage. At 3416, the system can assess whether the user has any alternative items, including items not in the first aid kit, that could make a suitable substitute for the missing gauze. For example, at 3416, the system can assess whether the user has any paper towels, rags, cloths, etc., that could be substituted for the missing gauze. At 3416, the user may be prompted to provide information about any additional materials available that may be suitable replacements for the missing first aid materials. This information can be provided in any of the ways previously described, including text-entry, voice-entry, photo- or video-entry, etc.

In some embodiments, the exchanges of information between the user and the system at this juncture can be led by the user in a bottom up fashion in which the user indicates to the system the first aid items that are in their possession (e.g., the user specifies that they have bandages, scissors, and antibiotic ointment), can be led by the system in a top down fashion in which the system prompts the user with questions regarding whether they possess specific first aid items (e.g., the system asks the user if they have gauze in possession and, if not, if they happen to have a shirt, sock or bandana that they could spare), or a combination thereof.

From decision state 3416, if the user does not have access to any suitable alternative first aid materials, the method 34400 can move to 318, at which the system can provide the user with recommendations on first aid materials to obtain. In some embodiments, 3418 provides the user with a list of first aid materials to acquire to treat the condition specified at 3402. In some embodiments, 3418 also provides the user with nearby options for where such materials can be obtained. Such nearby options can be determined, for example, at 3406 (e.g., from the nearby healthcare resources). In some embodiments, the user is provided with one or more links to online retailers that can sell and ship the first aid materials to the user. In some embodiments, the first aid materials can be sold by the system to the user.

From decision state 3414 (in the event that the user possesses sufficient first aid materials), from decision state 3416 (in the event that the user has found available alternative materials), or from 3418 (after obtaining the recommended materials), the method 3400 can move to 3420 at which first aid treatment guidance is provided to the user. Method step 3420 can be similar to 3210 of FIG. 32 (described above).

In some embodiments, the method 3400 can then move to 3422, at which the user is instructed to restock his or her first aid kit. At 3422, the user may be provided with a list of materials to obtain and can also be provided with a list of options from where the materials can be obtained in a manner similar to that which has been described above with reference to 3418. In some embodiments, users may have the option to have the materials delivered to them via a shipping service or a courier service for rapid same day delivery.

In some embodiments, the method 3400 then moves to 3424 at which the user is provided with instructions for subsequent care. For example, the system may instruct the user to change the bandage after a given period of time. In some embodiments, the instructions provided at 3424 can be provided in the form of alerts or notifications on the user device. For example, the system may alert the user two days later to change the bandage and provide instructions for doing so.

Figure 35:
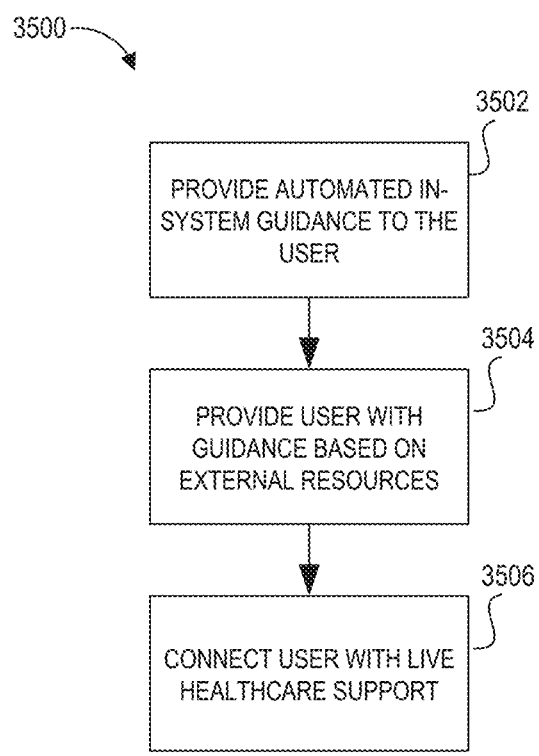
FIG. 35 illustrates an embodiment of an escalation method that can be used in some embodiments of the methods and systems for providing first aid guidance as described herein.

FIG. 35 illustrates an embodiment of an escalation method 3500 that can be used in some embodiments of the methods and systems for providing first aid guidance as described herein. The method 400 indicates that first aid guidance can be provided to the user (e.g., at 3210 of FIG. 32, 3314 of FIG. 33, or 3420 of FIG. 34) in a variety of ways. For example, at 3502, automated in-system guidance can be provided to the user in the form of text-based, audio-based, video-based, and/or AR-based guidance. Such guidance can be provided to the user through a GUI on a display of the user device. At 3504, the user may be linked to external resources that can provide additional detail and instruction. For example, the user can be linked from the system to resources located outside the system (e.g., resources generally available on the internet) where the user can find additional relevant treatment information. At 3506, the user can be connected with live healthcare support. For example, the user can be linked (via an audio and/or video connection) with a live healthcare professional who can walk the user through providing first aid. In some embodiments, one or more of the operations that are similar or equivalent to those described with reference to state 3506 may also be performed immediately prior to, during, or immediately subsequent to one or more of those described above with reference to states 3204-3206 of FIG. 32, 3306-3310 of FIG. 33, and 3408-3410 of FIG. 34. That is, in some embodiments, the system may task a live healthcare professional with determining or confirming whether the medical condition(s) specified by the user can or should be treated using first aid, connecting the user with a live healthcare professional who may be able to help the user determine whether emergency help is needed, and the like.

Figure 36:
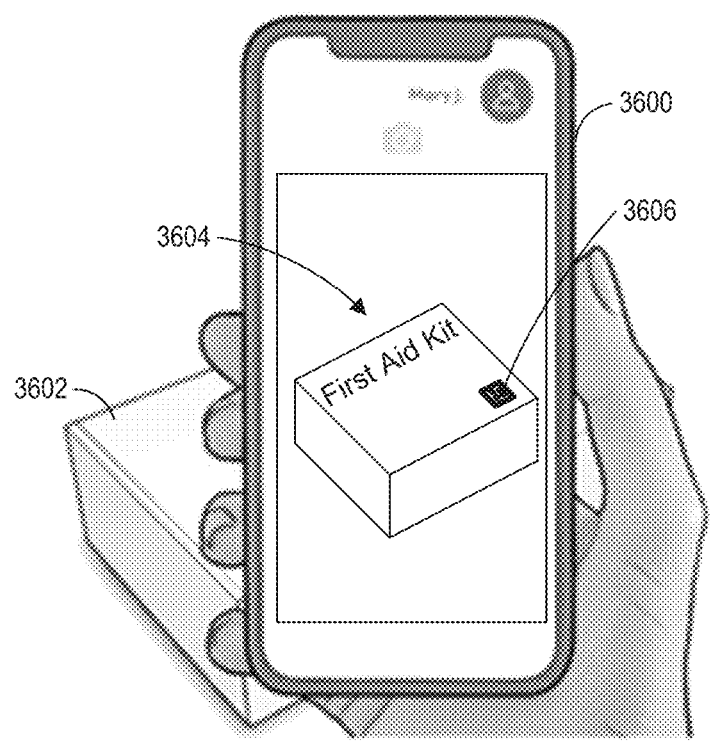
FIG. 36 illustrates an example of determining available first aid materials in a first aid kit using a user device, such as a mobile phone, as part of a method or system for providing first aid guidance according to embodiments described herein.

FIG. 36 illustrates an example of determining available first aid materials in a first aid kit 3602 using a user device 3600, such as a mobile phone, as part of a method or system for providing first aid guidance according to embodiments described herein. In the illustrated example, the user takes an image 3604 of his or her first aid kit 3602 using a camera on the mobile device. In some embodiments, the image can be analyzed, for example, using computer vision and/or machine learning, to recognize the make and/or model of the first aid kit 3602. In some embodiments, the first aid kit 3602 or contents of first aid kit 3602 may be recognized based on logos, labels, brand names, promotional text, or other text printed or otherwise provided on their exterior or packaging.

A list of the contents of the first aid kit 3602 can then be retrieved from an appropriate database. In FIG. 36, the first aid kit 3602 includes a machine-readable code 3606 (e.g., a bar code or QR code) printed thereon. In some embodiments, the make and/or model of the first aid kit 3602 can be determined by scanning the machine-readable code 3606. Once the make and/or model of the first kid 3602 is determined from the machine-readable code 3606, the contents of the first aid kit 3602 can then be retrieved from an appropriate database. Although the machine-readable code 506 is illustrated in FIG. 36 as an optical machine-readable code, other types of machine-readable codes (e.g., near field communication (NFC) and/or radio frequency identifiers (RFID) codes, among others, can also be used.

Figure 37:
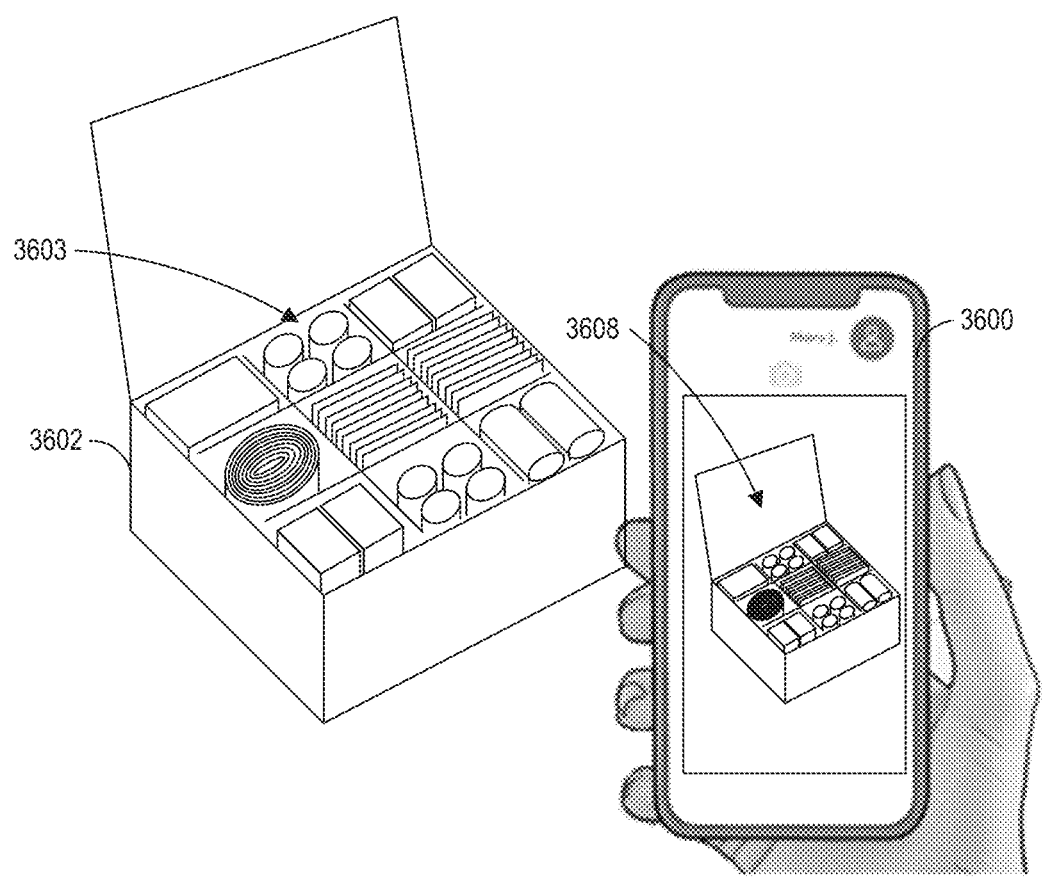
FIG. 37 illustrates another example of determining available first aid materials in a first aid kit using a user device, such as a mobile phone, as part of a method or system for providing first aid guidance according to embodiments described herein.

FIG. 37 illustrates another example of determining available first aid materials in a first aid kit 3602 using a user device 3600, such as a mobile phone, as part of a method or system for providing first aid guidance according to embodiments described herein. In the illustrated example, the user captures an image 3608 of first aid materials 3603 within the first aid kit 3602 using a camera on the user device 3600. The image can be analyzed, for example, using computer vision and/or machine learning, to recognize and determine which first aid materials are present in the image. Although FIG. 37 illustrates that in some embodiments the image 3608 can be captured with the first aid materials 3603 positioned within the first aid kit 3602, in other embodiments, the user may be instructed to remove the first aid materials 3603 from the kit 3602 before capturing the image. For example, the user may be instructed to lay the materials 3603 out in an array before capturing the image. As another example, the user may capture a plurality of images (e.g., an image of each different material 3603 in the first aid kit 3602). This may facilitate recognizing the first aid materials 3603 within the image(s).

FIG. 38 illustrates an example of providing augmented reality (AR) guidance to a user on a user device 3600, such as a mobile phone, as part of a method or system for providing first aid guidance according to embodiments described herein. In the illustrated example, AR guidance 3610 has been used to highlight the location of an item to be retrieved from the first aid kit in an image 3608 of the first aid kit. Use of AR guidance 3610 to overlay instructions or other guidance onto images (whether real time or not) can increase the clarity of the first aid guidance provided by the system. AR guidance 3610 can be used in other circumstances as well. AR-guidance 3610 can overlay first aid instructions onto an image or video of the person to be treated so as to show, for example, where and how to apply the first aid.

Figure 39:
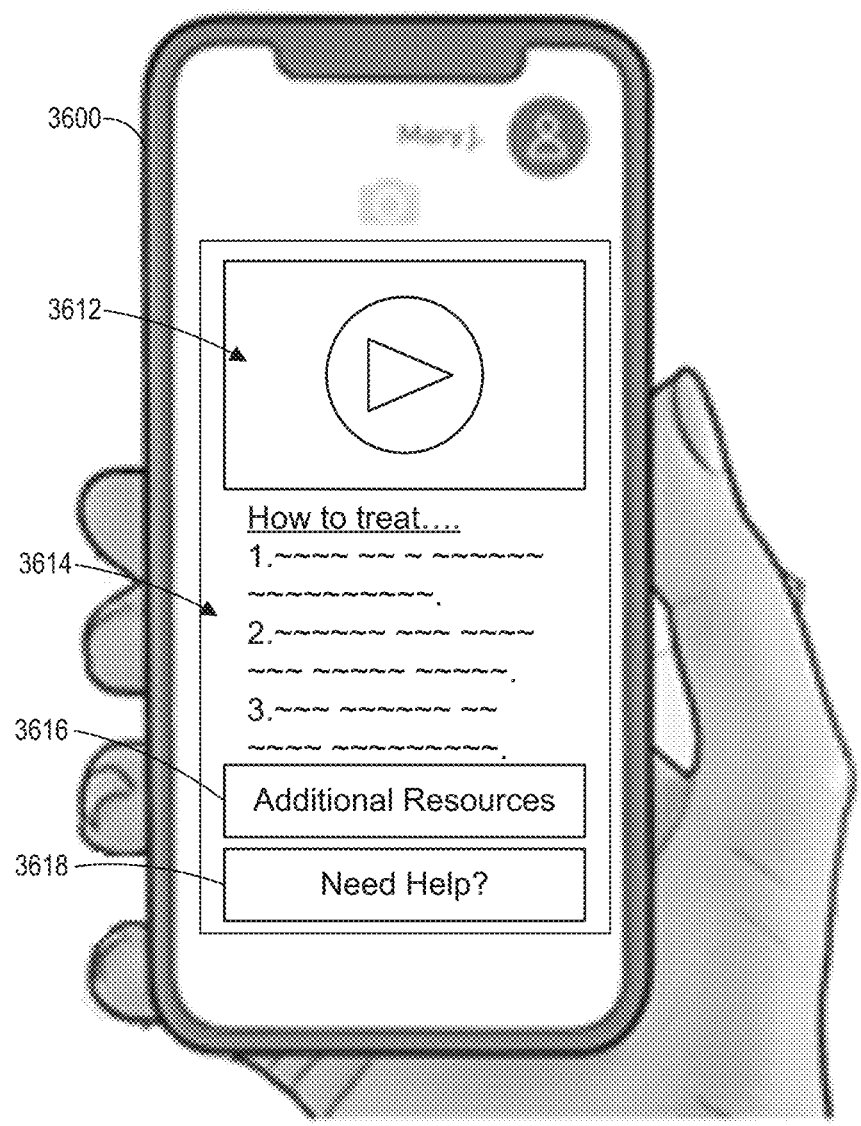
FIG. 39 illustrates an example of providing first aid guidance to a user on a user device, such as a mobile phone, as part of a method or system for providing first aid guidance according to embodiments described herein.

FIG. 39 illustrates an example of providing first aid guidance to a user on a user device 3600, such as a mobile phone, as part of a method or system for providing first aid guidance according to embodiments described herein. In the illustrated embodiment, a GUI is provided to the user on the user device 3600. In the illustrated embodiment, the guidance includes image or video guidance 3612, text-based guidance 3614, links to external resources 3616, and links to additional help sources 3618. In some embodiments, one or more of elements 3612 to 3618 may include or be presented in conjunction with AR guidance, such as AR guidance 3610 as described above with reference to FIG. 38. Not all of these features need be included in all embodiments and the arrangement and positioning of these elements in the illustrated example should not be construed as limiting. In some embodiments, the links to additional help sources 3618 can connect the user with a live healthcare professional who can provide immediate assistance and/or connect the user with emergency (e.g., 9-1-1 services) as appropriate.

The first aid materials, items, and first aid kit contents as described herein may include, but are not limited to, one or more of the following: absorbent compress dressings, activated charcoal, adhesive bandages of assorted sizes, adhesive cloth tape, alcohol pads, antibacterial wipes, antibiotic ointment, aloe, antihistamines, antiseptic spray or wipe packets, aspirin or other over-the-counter anti-inflammatory medication, cotton balls or swabs, diagnostic test kits, emergency blankets, epinephrine autoinjector ("EpiPen"), eye drops, eye patches, eye wash, face mask, face shield, flash light, breathing barriers (with one-way valves), burn gel dressings, hand sanitizer or cleaner, hydrogen peroxide, instant cold compresses, non-latex gloves, hydrocortisone ointment, gauze roll bandages, plastic bags, roller bandages, safety pins, scissors, splints, sterile gauze pads of assorted sizes, sterile water, sting relief stick or pad, syrup of Ipecac, oral thermometers, tissues, triangular bandages, towels, and tweezers. In some embodiments, one or more of the first aid kits described herein may correspond to a group of one or more first aid materials or items that are sold together and/or are stored or transported by a user in a common receptacle or otherwise together. Alternatively, in some embodiments, one or more of the first aid kits described herein may correspond to a first aid item together with its corresponding packaging, receptacle, and/or other complementary components.

Figure 40:
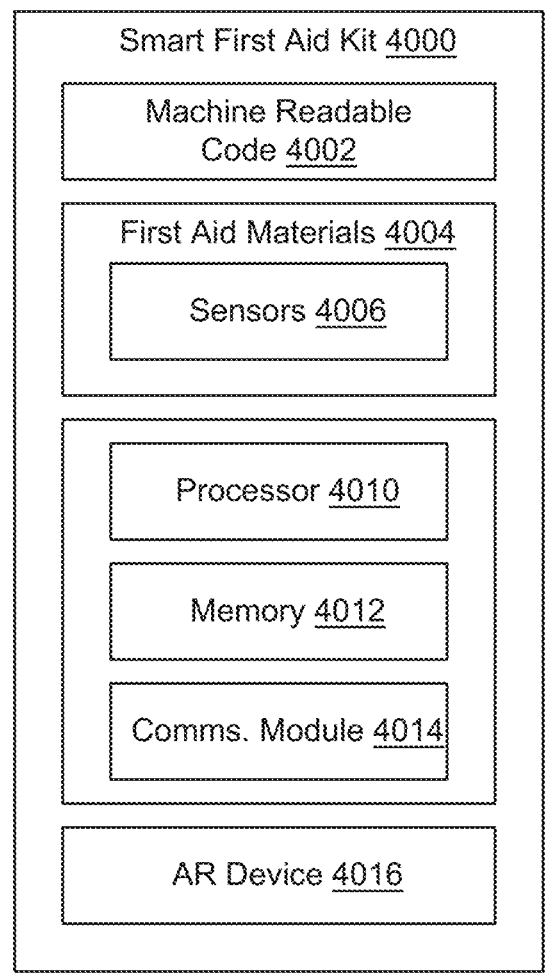
FIG. 40 is a block diagram illustrating components of a smart first aid kit that can be used in some of the embodiment of systems and methods for providing first aid guidance as described in the present disclosure.

FIG. 40 is a block diagram illustrating components of a smart first aid kit 4000 that can be used in some of the embodiment of systems and methods for providing first aid guidance as described in the present disclosure. In the illustrated embodiment, the smart first aid kit 4000 includes a machine-readable code 4002. The machine-readable code 4002 can be configured to be scanned by a user device to, for example, provide a link to an application for providing first aid guidance for providing first aid using the materials of the first aid kit 4000. The machine-readable code 4002 can take a number of different formats including any of the machine-readable formats described above.

In the illustrated embodiment, the smart first aid kit 4000 also includes a supply of first aid materials 4004. The first aid materials 4004 can be similar to those first aid materials that are included in other (e.g., non-smart) first aid kits. However, as shown in FIG. 40, in some embodiments, the first aid materials 4004 can include sensors 4006 which allow the smart first aid kit 4000 to determine whether the first aid materials 4004 are present in the kit. For example, if the user uses all of the band aids in the kit, the kit may determine, based on the output of the sensors 4006 that no more band aids remain. This information can be used to instruct the user to obtain more band aids to restock the first aid kit 4000 as well as during first aid guidance provided to the user. For example, if the kit 4000 knows that it does not include band aids, the first aid guidance provided to the user can be modified to not include instructions to use band aids for treatment.

In the illustrated embodiment, the smart first aid kit also includes a processor 4010, a memory 4012, and a communications module 4014. These components can enable the smart aid kit to, for example, determine the contents of the kit based on the sensors 4006 and/or communicate information about the contents of the kit with external devices, such as the user device and/or the first aid guidance application. In some embodiments, the smart first aid kit 4000 includes a box, container, or other receptacle for carrying first aid materials. In at least some of these embodiments, the machine readable code 4002 may be provided on a surface of the receptacle. Furthermore, in some of these embodiments, one or more components of sensors 4006, processor 4010, memory 4012, and/or communications module 4014 may be integrated into the receptacle or attached to a surface thereof.

In some embodiments, the smart first aid kit 4016 can include an AR device 4016. For example, in some embodiments, the AR device 4016 can comprise AR glasses or goggles that can be worn while providing first aid using the kit and onto which instructions for providing first aid can be overlaid. In some embodiments, the AR device 4016 can correspond to the user device that is described above as being used to scan the machine-readable code 4002, or may take the form of any of the other user devices described herein. In at least some of these embodiments, the AR device 4016 may be optionally stowed in the abovementioned receptacle, but may not be physically coupled thereto. Furthermore, in some of these embodiments, one or more components of sensors 4006, processor 4010, memory 4012, and/or communications module 4014 may correspond to components of the aforementioned the AR device 4016 and/or other user device or may otherwise not be physically coupled to the abovementioned receptacle.

Computer Systems

Figure 41:
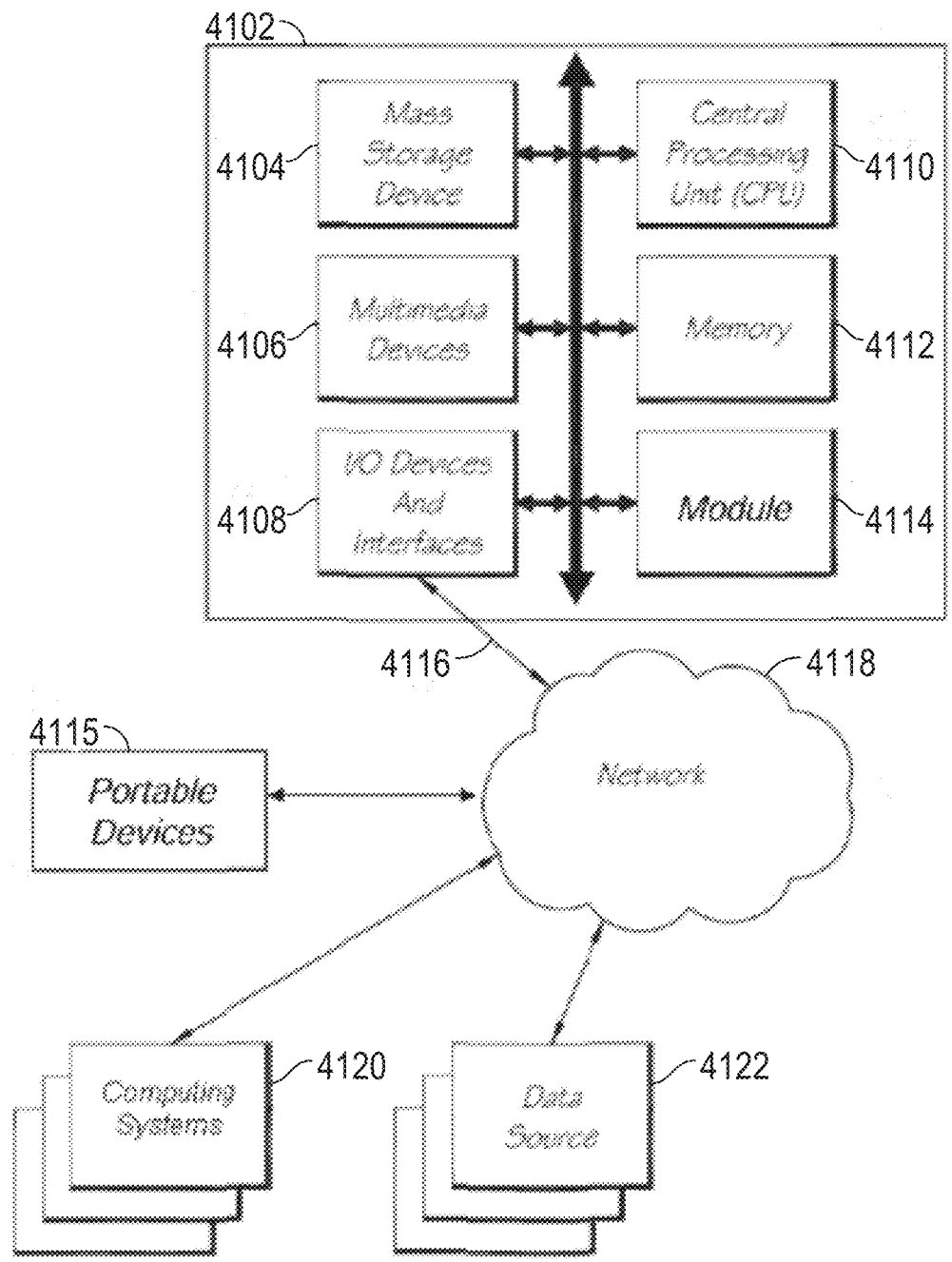
FIG. 41 is a block diagram illustrating an example embodiment of a computer system configured to run software for implementing one or more embodiments of the systems, methods, and devices disclosed herein.

FIG. 41 is a block diagram depicting an embodiment of a computer hardware system 1800 configured to run software for implementing one or more embodiments of the health testing and diagnostic systems, methods, and devices disclosed herein.

In some embodiments, the systems, processes, and methods described herein are implemented using a computing system, such as the one illustrated in FIG. 41. The example computer system 4102 is in communication with one or more computing systems 4120 and/or one or more data sources 4122 via one or more networks 4118. While FIG. 41 illustrates an embodiment of a computing system 4102, it is recognized that the functionality provided for in the components and modules of computer system 4102 may be combined into fewer components and modules, or further separated into additional components and modules.

The computer system 4102 can comprise a health testing and diagnostic module 4114 that carries out the functions, methods, acts, and/or processes described herein (e.g., via health testing and diagnostic platform 4202 shown in FIG. 42). The health testing and diagnostic module 4114 is executed on the computer system 4102 by a central processing unit 4106 discussed further below.

In general, the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 4102 includes one or more processing units (CPU) 4106, which may comprise a microprocessor. The computer system 4102 further includes a physical memory 4110, such as random access memory (RAM) for temporary storage of information, a read only memory (ROM) for permanent storage of information, and a mass storage device 4104, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1802 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 4102 includes one or more input/output (I/O) devices and interfaces 4112, such as a keyboard, mouse, touch pad, and printer. The I/O devices and interfaces 4112 can include one or more display devices, such as a monitor, that allows the visual presentation of data to a user. More particularly, a display device provides for the presentation of GUIs as application software data, and multi-media presentations, for example. The I/O devices and interfaces 4112 can also provide a communications interface to various external devices. The computer system 4102 may comprise one or more multi-media devices 4108, such as speakers, video cards, graphics accelerators, and microphones, for example.

The computer system 4102 may run on a variety of computing devices, such as a server, a Windows server, a Structure Query Language server, a Unix Server, a personal computer, a laptop computer, and so forth. In other embodiments, the computer system 4102 may run on a cluster computer system, a mainframe computer system and/or other computing system suitable for controlling and/or communicating with large databases, performing high volume transaction processing, and generating reports from large databases. The computing system 4102 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 4102 illustrated in FIG. 41 is coupled to a network 4118, such as a LAN, WAN, or the Internet via a communication link 4116 (wired, wireless, or a combination thereof). Network 4118 communicates with various computing devices and/or other electronic devices. Network 4118 is communicating with one or more computing systems 4120 and one or more data sources 4122. The health testing and diagnostic module 4114 may access or may be accessed by computing systems 4120 and/or data sources 4122 through a web-enabled user access point.

Connections may be a direct physical connection, a virtual connection, and other connection type. The web-enabled user access point may comprise a browser module that uses text, graphics, audio, video, and other media to present data and to allow interaction with data via the network 4118.

Access to the health testing and diagnostic module 4114 of the computer system 4102 by computing systems 4120 and/or by data sources 4122 may be through a web-enabled user access point such as the computing systems' 4120 or data source's 4122 personal computer, cellular phone, smartphone, laptop, tablet computer, e-reader device, audio player, or another device capable of connecting to the network 4118. Such a device may have a browser module that is implemented as a module that uses text, graphics, audio, video, and other media to present data and to allow interaction with data via the network 4118.

The output module may be implemented as a combination of an all-points addressable display such as a cathode ray tube (CRT), a liquid crystal display (LCD), a plasma display, or other types and/or combinations of displays. The output module may be implemented to communicate with input devices 4112 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 4102 may comprise a physical or logical connection established between a remote microprocessor and a mainframe host computer for the express purpose of uploading, downloading, or viewing interactive data and databases on-line in real time. The remote microprocessor may be operated by an entity operating the computer system 4102, including the client server systems or the main server system, an/or may be operated by one or more of the data sources 4122 and/or one or more of the computing systems 4120. In some embodiments, terminal emulation software may be used on the microprocessor for participating in the micro-mainframe link.

In some embodiments, computing systems 4120 who are internal to an entity operating the computer system 4102 may access the health testing and diagnostic module 4114 internally as an application or process run by the CPU 4106.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

In some embodiments, one or more features of the systems, methods, and devices described herein can utilize one or more application programming interfaces (API) to access data, communicate with other computing systems and interact with external software components. In some embodiments, an API may be utilized to retrieve test result information (e.g., an indication of whether user tested positive or negative for COVID-19, the date on which test was conducted, etc.).

The computing system 4102 may include one or more internal and/or external data sources (for example, data sources 1822). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 4102 may also access one or more databases 4122. The databases 4122 may be stored in a database or data repository. The computer system 4102 may access the one or more databases 4122 through a network 4118 or may directly access the database or data repository through I/O devices and interfaces 4112. The data repository storing the one or more databases 4122 may reside within the computer system 4102.

FIG. 42 is a block diagram illustrating an example embodiment of a computer system configured to run software for implementing one or more embodiments of the health testing and diagnostic systems, methods, and devices disclosed herein. In some embodiments, the various systems, methods, and devices described herein may also be implemented in decentralized systems such as, for example, blockchain applications. For example, blockchain technology may be used to maintain user profiles, proctor profiles, test results, test site databases, and/or financing databases or ledgers, dynamically generate, execute, and record testing plan agreements, perform searches, coordinate inventory tracking and reordering of medical diagnostic test kits, coordinate generation of virtual test completion passes, coordinate augmented reality content display, conduct patient-proctor matching, determine pricing, coordinate prescription medication order, fulfillment, and delivery, and conduct any other functionalities described herein.

In some embodiments, a remote health testing and diagnostic platform 4202 may be comprised of a registration and purchase module 4204, a testing module 4206, an analytics module 4208, and a reporting module 4210. The health testing and diagnostic platform 4202 may also comprise a user profile database 4212, a proctor database 4214, a test database 4216, and/or a site database 4218. The health testing and diagnostic platform 4202 can be connected to a network 4220. The network 4220 can be configured to connect the health testing and diagnostic platform 4202 to one or more proctor devices 4222, one or more user devices 4224, one or more pharmacy systems 4226, one or more third-party provider systems 4228 (e.g., payment providers, prescriber providers, courier service providers), and/or one or more government systems 4230.

The registration and purchase 4204 may function by facilitating patient registration through one or more registration interfaces and in conjunction with the user database 4212, store user registration data. The testing module 4206 may be configured to allow a user to initiate and complete a medical test or visit with a proctor through a series of pre-testing and testing interfaces, as described herein. The analytics module 4208 may be configured to dynamically analyze patient tests across a given population stored in the test database 4216 and provide structured data of the test results. The reporting module 4210 may function by dynamically and automatically reporting test results to government entities, patients, and third parties using one or more interfaces, such as one or more application programming interfaces. Each of the modules can be configured to interact with each other and the databases discussed herein.

Additional Embodiments

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will also be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein, but are to be accorded the widest scope consistent with this disclosure, the principles and the novel features disclosed herein.

What is claimed is:

1. A drug testing system comprising:
    a drug test kit adapted to facilitate user completion of a drug test comprising:
        a test reference element; and
        a test kit container bearing a machine-readable code on an external surface thereof, the machine-readable code configured to be imaged by a camera of a user computing device to enable:
            providing a fiducial point from which a coordinate frame for an augmented reality presentation can be established using the camera and a display of the user computing device;
            causing the user computing device to display a user-selectable graphic on the display of the user computing device that, when selected by a user, causes a software application stored on the user computing device to access a webpage that enables initiation of the augmented reality presentation that includes display of augmented reality content relating to the drug test kit;
        causing a computing system to establish an electronic video conference session between a proctor device and the user computing device, wherein:
            during the electronic video conference session, a proctor views, on the proctor device, a live video of the user taking the drug test,
            the live video is captured using the camera of the user computing device of the user, and
            the drug test results in a drug indicator indicating a result of the drug test that is viewable by the proctor in the live video;
        causing the computing system to receive an indication that the drug indicator indicates that the user has tested positive for the drug based on the drug test, wherein the indication is provided by the proctor using the proctor device and based on the proctor viewing the live video; and
        causing the computing system to verify that testing procedures associated with the drug test are completed properly by analyzing monitored video frame data associated with the live video received from the user computing device to determine at least one of:
            that a swab used by the user during the drug test was inserted into an orifice at a proper insertion depth,
            that a testing solution used during the drug test was correctly applied by the user to a test card associated with the drug test,
            that the test card remains undisturbed during a predetermined dwell time associated with the drug test, and
            that a horizontal or vertical distance between a patient reference element and the test reference element remains under a predetermined threshold value;
        wherein the computing system comprises an electronic storage medium storing computer-executable instructions and one or more processors configured to execute the computer-executable instructions.

2. The system of claim 1, wherein the machine-readable code is further configured to enable causing the computing system to transmit the indication to a third party.

3. The system of claim 1, wherein the machine-readable code is further configured to enable causing the computing system to display information regarding the indication to the user on the user computing device.

4. The system of claim 1, wherein the machine-readable code is further configured to enable causing the computing system to display information regarding the indication to the proctor on the proctor device.

5. The system of claim 1, wherein the augmented reality content provides instructions for performing at least one step of the drug test.

6. The system of claim 1, wherein the drug test is provided in the drug test kit, wherein the drug test kit further comprises a plurality of drug tests, and wherein each of the plurality of drug tests is for testing for a different drug.

7. The system of claim 1, wherein the drug test is provided in a medical diagnostic test kit that comprises a plurality of medical diagnostic test kits.

8. A method for proctored examination for a drug test_provided within a drug test kit comprising a test reference element and a test kit container bearing a machine-readable code on an external surface thereof, the method comprising, in response to the machine-readable code being imaged by a camera of a user computing device:

providing a fiducial point from which a coordinate frame for an augmented reality presentation can be established using the camera and a display of the user computing device;

causing the user computing device to display a user-selectable graphic on the display of the user computing device that, when selected by a user, causes a software application stored on the user computing device to access a webpage that enables initiation of the augmented reality presentation that includes display of augmented reality content relating to the drug test kit;

causing a computing system to receive a user request from the user computing device of the user for the proctored examination for a drug;

causing the computing system to establish an electronic video conference session between a proctor device and the user computing device, wherein:

during the electronic video conference session, a proctor views, on the proctor device, a live video of the user taking the drug test, the live video is captured using a camera of the user computing device of the user, and the drug test results in a drug indicator indicating a result of the drug test that is viewable by the proctor in the live video;

causing the computing system to receive an indication that the drug indicator indicates that the user has tested positive for the drug based on the drug test, wherein the indication is provided by the proctor using the proctor device and based on the proctor viewing the live video; and causing the computing system to verify that testing procedures associated with the drug test are completed properly by analyzing monitored video frame data associated with the live video received from the user computing device to determine at least one of:

that a swab used by the user during the drug test was inserted into an orifice at a proper insertion depth, that a testing solution used during the drug test was correctly applied by the user to a test card associated with the drug test, that the test card remains undisturbed during a predetermined dwell time associated with the drug test, and that a horizontal or vertical distance between a patient reference element and the test reference element remains under a predetermined threshold value.

9. The method of claim 8, wherein the method further comprises causing the computing system to transmit the indication to a third party.

10. The method of claim 8, wherein the method further comprises causing the user computing device to display information regarding the indication to the user on the user computing device.

11. The method of claim 8, wherein the method further comprises causing the proctor device to display information regarding the indication to the proctor on the proctor device.

12. The method of claim 8, wherein the augmented reality content provides instructions for performing at least one step of the drug test.

13. The method of claim 8, wherein the drug test is provided in the drug test kit, wherein the drug test kit further comprises a plurality of drug tests, and wherein each of the plurality of drug tests is for testing for a different drug.

14. The method of claim 8, wherein the drug test is provided in a medical diagnostic test kit that comprises a plurality of medical diagnostic test kits.

\* \* \* \* \*